United States Patent [19]

Yamada et al.

[11] Patent Number: 6,117,975
[45] Date of Patent: Sep. 12, 2000

[54] MELANOCORTIN RECEPTOR POLYPEPTIDES MC-3, MC-4, AND MC-5

[75] Inventors: Tadataka Yamada; Ira Gantz, both of Ann Arbor, Mich.

[73] Assignee: The Regents of the University of Michigan, Ann Arbor, Mich.

[21] Appl. No.: 08/629,335

[22] Filed: Jul. 23, 1996

Related U.S. Application Data

[62] Division of application No. 08/200,711, Feb. 17, 1994, Pat. No. 5,622,860.

[51] Int. Cl.$^7$ .......................... C07K 14/72; C07K 14/68; C07K 14/695; C12N 15/12
[52] U.S. Cl. .......................... 530/350; 536/23.5; 530/306
[58] Field of Search .................................. 530/350, 306, 530/399; 536/23.5

[56] References Cited

U.S. PATENT DOCUMENTS

| 5,280,112 | 1/1994 | Cone et al. | 536/23.5 |
| 5,532,347 | 7/1996 | Cone et al. | 536/23.5 |
| 5,554,729 | 9/1996 | Cone et al. | 530/350 |

OTHER PUBLICATIONS

Bao, L. et al., "Mapping of Genes for the Human C5a Receptor (C5AR), Human FMLP Receptor (FPR), and Two FMLP Receptor Homologue Orphan Receptors (FPRH1, FPRH2) to Chromosome 19," *Genomics* 13:437–440 (1992).

Berridge, M.J. et al., "Changes in the Levels of the Inositol Phosphates after Agonist–Dependent Hydrolysis of Membrane Phosphoinositides," *Biochem. J.* 212:473–482 (1983).

Brown, N.A. et al., "Induction of Alkaline Phosphatase in Mouse L Cells by Overexpression of the Catalytic Subunit of cAMP–Dependent Protein Kinase," *J. Biol. Chem.* 265:13181–13189 (1990).

Buffey, J. et al., "α–Melanocyte–Stimulating Hormone Stimulates Protein Kinase C Activity in Murine B16 Melanoma," *J. Endocrinol.* 133:333–340 (1992).

Cannon, J.G. et al., "αMelanocyte Stimulating Hormone Inhibits Immunostimulatory and Inflammatory Actions of Interleukin 1," *J. Immunol.* 137:2232–2236 (1986).

Chabre, O. et al., "A Recombinbant Calcitonin Receptor Independently Stimulates 3', 5'–Cyclic Adenosine Monophosphate and $CA^{2+}$/Inositol Phosphate Signaling Pathways," *Mol. Endocrinol.* 6:551–555 (1992).

Challis, J.R.G. et al., "Is α MSH a a Trophic Hormone to Adrenal Function in the Foetus?" *Nature* 269:818–819 (1977).

Chen, C.A. et al., "Calcium Phosphate–Mediated Gene Transfer: A Highly Efficient Transfectioin System for Stably Transforming Cells with Plasmid DNA," *Biotechniques* 6:632–638 (1988).

Chhajlani, V. et al. "Molecular Cloning and Expression of the Human Melanocyte Stimulating Hormone Receptor cDNA," *FEBS* 309:417–420 (1992).

Chijiwa, T. et al., "Inhibition of Forskolin–Induced Neurite Outgrowth and Protein Phosphorylation by a Newly Synthesized Selective Inhibitor of Cyclic AMP–Dependent Protein Kinase, $^N$–[2–($^P$–Bromocinnamylamino)ethyl]–5–isoquinolinesulfonamide (H–89), of PC12D Pheochromocytoma Cells," *J. Biol. Chem.* 265:5267–5272 (1990).

Chomczynski, P. et al., "Single–Step Method of RNA Isolation by Acid Guanidinium Thiocyanate–Phenol–Chloroform Extraction," *Anal. Biochem.* 162:156–159 (1987).

Clark, D. et al., "Immunoreactive α–MSH in Human Plasma in Pregnancy," *Nature* 273:163–164 (1978).

Cone, R.D. et al., "Molecular Genetics of the ACTH and Melanocyte–Stimulating Hormone Receptors" *TEM* 4:242–247 (1993).

Cossu, G. et al., "Adrenocorticotropin is a Specific Mitogen for Mammalian Myogenic Cells," *Dev. Biol.* 131:331–336 (1989).

Cotecchia, S. et al., "Multiple Second Messenger Pathways of α–Adrenergic Receptor Subtypes Expressed in Eukaryotic Cells," *J. Biol. Chem.* 265:63–69 (1990).

DeBold, C.R. et al., "Proopiomelanocortin Gene is Expressed in Many Normal Human Tissues and in Tumors not Associated with Ectopic Adrenocorticotropin Syndrome," *Mol. Endocrinol.* 2:862–870 (1988).

Degani, H. et al., "Stimulation of cAMP and Phosphomonoester Production by Melanotropin in Melanoma Cells: $^{31}$P NMR Studies," *PNAS (USA)* 88:1506–1510 (1991).

DelValle, J. et al., "Regulation of $[Ca^{2+}]_i$ by Secretagogue Stimulation of Canine Gastric Parietal Cells," *Am. J. Physiol.* 262:G420–426 (1992).

DelValle, J. et al., "Characterization of $H_2$ Histamine Receptor: Linkage to Both Adenylate Cyclase and $[Ca^{2+}]_i$ Signaling Systems," *Am. J. Physiol.* 263:G967–972 (1992).

De Wied, D. et al., "Stress Modulation of Learning and Memory Processes," *Methods Achiev. Exp. Pathol.* 15:167–199 (1991).

De Wied, D. et al., "Neuorpeptides Derived from Pro–Opiocortin: Behavioral, Physiological, and Neurochemical Effects," *Physiol. Rev.* 62:976–1059 (1982).

Ellerkmann, E. et al., "α–Melanocyte–Stimulating Hormone is a Mammotrophic Factor Released by Neurointermediate Lobe Cells after Estrogen Treatment," *Endocrinol.* 130:133–138 (1992).

(List continued on next page.)

*Primary Examiner*—Stephen Walsh
*Assistant Examiner*—Claire M. Kaufman
*Attorney, Agent, or Firm*—Harness, Dickey & Pierce P.L.C.

[57] ABSTRACT

Genes encoding melanocortin receptors have been identified, isolated, cloned and localized to their chromosomal positions. These genes have been used to transfect mammalian cells lacking endogenous melanocortin receptors to induce expression. Additionally, melanocortin receptor binding, secondary signalling, and tissue distribution has been characterized. The genes and their gene products may therefore be used to to provide therapeutic vehicles for the treatment of processes involving the function of melanocortin receptors.

5 Claims, 27 Drawing Sheets

OTHER PUBLICATIONS

Enyeart, J.J. et al., "T–Type $Ca^{2+}$ Channels are Requred for Adenocorticotropin–Stimulated Cortisol Production by Bovine Adrenal Zona Fasciculata Cells," *Mol. Endo.* 7:1031–1040 (1993).

Farese, R.V. et al., "Dual Activation of the Inositol–Triphosphate–Calcium and Cyclic Nucleotide Intracellular Signaling Systems by Adrenocorticotropin in Rat Adrenal Cells," *Biochem. Biophys. Res. Comm.* 135:742–748 (1986).

Felgner, P.L. et al., "Lipofection: A Highly Efficient, Lipid––mediated DNA–Transfection Procedure," *PNAS (USA)* 84:7413–7414 (1987).

Gantz, I. et al., "Molecular Cloning of a Gene Encoding the Histamine H2 Receptor," *PNA (USA)* 88:429–433 (1991).

Gantz, I. et al., "Localization of the Genes Encoding the Melanocortin–2 (Adrenocorticotropic Hormone) and Melanocortin–3 Receptors to Chromosomes 18p11.2 and 20q13.2–q13.3 by Fluorescence in Situ Hybridization," *Genomics* 18:166–167 (1993).

Gantz, I. et al., "Molecular Cloning, Expression, and Characterization of a Fifth Melanocortin Receptor," *Biochem. Biophys. Res. Comm.* 200:1214–1220 (1994).

Gantz, I. et al., "Molecular Cloning, Expression, and Gene Localization of a Fourth Melanocortin Receptor," *J. Biol. Chem.* 268:15174–15179 (1993).

Gantz, I. et al., "Molecular Cloning of a Novel Melanocortin Receptor," *J. Biol. Chem.* 268:8246–8250 (1993).

Gantz, I. et al., "Mapping of the Gene Encoding the Melanocortin–1 (α–Melanocyte Stimulating Hormone) Receptor (MC1R) to Human Chromosome 16q24.3 by Fluorescence In Situ Hybridization," *Genomics* 19:394–395 (1994).

Garren, L.D., "The Mechanism of Action of Adrenocorticotropic Hormone," *Vitam. Horm.* 26:119–141 (1968).

Gebbink, M.F.B.G. et al., "Cloning, Expression and Chromosomal Localization of a New Putative Receptor–Like Protein Tyrosine Phosphatase," *FEBS* 290:123–130 (1991).

Gispen, W.H. et al., "The Behaviorally Active Neuropeptide ACTH as Neurohormone and Neuromodulator: The Role of cyclic Nucleotides and membrane Phosphorproteins," *Adv. Exp. Biol. Med.* 116:199–2249 (1979).

Gispen, W.H., "Therapeutic Potential for Melanocortins in Peripheral Nerve Disease," *Trends Pharm. Sci.* 11:221–222 (1992).

Goverde, H.J.M. et al., "Major Contribution of the Basic Amino Acid Lysine at Position 11 to the Bioactivity of ACTH in Purified Isolated Rat Adrenocortical Cells," *Biochem. Biophys. Res. Comm.* 190:1060–1065 (1993).

Gruber, K.A. et al., "ACTH–(4–10) through γ–MSH: Evidence for a New Class of Central Autonomic Nervous System–Regulating Peptides," *Am. J. Physiol.* 257:R681–R694 (1989).

Gudermann, T. et al., "Evidence for Dual Coupling of the Murine Luteinizing Hormone Receptor to Adenylyl cyclase and Phosphoinositide Breakdown and $Ca^{2+}$ Mobilization," *J. Biol. Chem.* 267:4479–4488 (1992).

Guyer, C.A. et al., "Cloning, Sequencing, and Expression of the Gene Encoding the Porcin $α_2$–Adrenergic Receptor," *J. Biol. Chem.* 265:17307–17317 (1990).

Hausdorff, W.P. et al., "Turning off the Signal: Desensitization of β–Adrenergic Receptor Function," *FASEB J.* 4:2881–2889 (1990).

Hiltz, M.E. et al., "Antiinflammatory Activity of a COOH–Terminal Fragment of the Neuropeptide α–MSH," *FASEB J.* 3:2282–2284 (1989).

Hiltz, M.E. et al., "Anti–Inflammatory Activity of a α–MSH(11–13) Analogs: Influences of Alteration in Stereochemistry," *Peptides* 12:767–771 (1991).

Hughes, S. et al., "α–Melanotropin and β–Endorphin Immunoreactivity in Different Skeletal Muscle Fiber Types," *Annals N. Y. Acad. Sci.* 680:536–538 (1993).

Ilan, A.B. et al., "Alpha Melanocyte Stimulating Hormone(α–MSH) Enhances Eicosanoid Production by Bovine Retinal Pigment Epithelium," *Prostaglandins* 43:31–44 (1992).

Jelinek, L.J. et al., "Expression Cloning and Signaling Properties of the Rat Glucagon Receptor," *Science* 259:1614–1616 (1993).

Kennelly, P.J. et al., "Consensus Sequences as Substrate Specificity Determinants for Protein Kinases and Protein Phosphatases," *J. Biol. Chem.* 266:1555–1558 (1991).

Khorram, O. et al., "Physiological Role of α–Melanocyte–Stimulating Hormone in Modulating the Secretion of Prolactin and Luteinizing Hormone in the Female Rat," *PNAS (USA)* 81:8004–8008 (1984).

Kojima, I. et al., "Role of Calcium and cAMP in the Action of Adrenocorticotropin on Aldosterone Secretion," *J. Biol. Chem.* 260:4248–4254 (1985).

Konda, Y. et al., "Interaction of Dual Intracellular Signaling Pathways Activated by the Melanocortin–3 Receptor," *J. Biol. Chem.* 269:13162–13166 (1994).

Konda, Y. et al., "Activation of Divergent intracellular Signaling Mechanisms by a Novel Brain–Gut Melanocortin Receptor," *Gastroenterol.* 104:A834 (1993) (Abstract).

Krieger, D.T., "Placenta as a Source of 'Brain' and 'Pituitary' Hormones," *Biol. Reprod.* 26:55–71 (1982).

Lefkowitz, R.J. et al., "Adrenergic Receptors" *J. Biol. Chem.* 263:4993–4996 (1988).

Lemieux, N. et al., "A Simple Method for Simultaneous R– or G–Banding and Fluorescence in Situ Hybridization of Small Single–Copy Genes," *Cytogenet. Cell Genet.* 59:311–312 (1992).

Libert, F. et al., "Selective Amplification and Cloning of Four New Members of the G Protein–Coupled Receptor Family," *Science* 244:569–572 (1989).

Lichter, P. et al., "High–Resolution Mapping of Human Chromosome 11 by in Situ Hybridization with Cosmid Clones," *Science* 247:64–69 (1990).

Low, M. et al., "Proposed Preferred Conformation of ACTH," *Acta Biochem. Biophys. Acad. Sci. Hung.* 10:229–231 (1975).

Low, M. et al., "Role of Chain Termini in Selective Steroidogenic Effect of ACTH/MSH (4–10) on Isolated Adrenocortical Cells," *Peptides* 11:29–31 (1989).

Maniatis, T. et al., *Molecular Cloning; A Laboratory Manual*, Cold Springs Harbor Laboratory, Cold Springs, NY, pp. 387–389 (1982).

Meltzer, P.S. et al., "Rapid Generation of Region Specific Probes by Chromosome Microdissection and Their Application," *Nature Genet.* 1:24–28 (1992).

Montmayeur, J.P. et al., "Differential Expression of the Mouse $D_2$ Dopamine Receptor Isoforms," *FEBS Lett.* 278:239–243 (1991).

Mountjoy, K.G. et al., "The Cloning of a Family of Genes that Encode the Melanocortin Receptors," *Science* 257:1248–1251 (1992).

Murphy, M.T. et al., "Antipyretic Potency of Centrally Administered α–Melanocyte Stimulating Hormone," *Science* 221:192–193 (1983).

Nakanishi, S. et al., "Nucleotide Sequence of Cloned cDNA for Bovine Corticotropin–β–Lipotropin Precursor," *Nature* 278:423–427 (1979).

Nakajima, Y. et al., "Direct Linkage of Three Tachykinin Receptors to Stimulation of Both Phosphatidylinositol Hydrolysis and Cyclic AMP Cascades in Transfected Chinese Hamster Ovary Cells," *J. Biol. Chem.* 267:2437–2442 (1992).

Orwoll, E.S. et al., "β–Endorphin and Adrenocorticotropin in Extrapituitary Sites: Gastrointestinal Tract," *Endocrinology* 107:438–442 (1980).

Peralta, E.G. et al., "Differential Regulation of PI Hydrolysis and Adenylyl Cyclase by Muscarinic Receptor Subtypes," *Nature* 334:434–437 (1988).

Pinkel, D. et al., "Cytogenetic Analysis Using Quantitative, High–Sensitivity, Fluorescence Hybridization," *PNAS (USA)* 83:2934–2938 (1986).

Rhee, S.G. et al., "Phospholipase C Isozymes and Modulation by cAMP–Dependent Protein Kinase," *Adv. Sec. Mess. Phosphoprotein Res.* 28:57–64 (1993).

Robbins, L.S. et al., "Pigmentation Phenotypes of Variant Extension Locus Alleles Result from Point Mutations that Alter MSH Receptor Function," *Cell* 72:827–834 (1993).

Roselli–Rehfuss, L., et al., "Identification of a Receptor for γ Melanotropin and Other Proopiomelanocortin Peptides in the Hypothalamus and Limbic System," *PNAS (USA)* 90:8856–8860 (1993).

Rousseau–Merck, M.F. et al., "The Chromosomal Localization of the Human Follicle–Stimulating Hormone Receptor Gene (FSHR) on 2p21–p16 is Similar to that of the Luteinizing Hormone Receptor Gene," *Genomics* 15:222–224 (1993).

Samia, J.A. et al., "Chromosomal Organization and Localization of the Human Urokinase Inhibitor Gene: Perfect Structural Conservation with Ovalbumin," *Genomics* 6:159–167 (1990).

Sanchez–Franco, F. et al., "Immunoreactive Adrenocorticotropin in the Gastrointestinal Tract and Pancreatic Islets of the Rat," *Endocrinol.* 108:2235–2238 (1981).

Schwyzer, R., "ACTH: A Short Introductory Review," *Annal. N.Y. Acad. Sci.* 297:3–26 (1977).

Silman, R.E. et al., "Human Foetal Pituitary Peptides and Parturition," *Nature* 260:716–718 (1976).

Supattapone, S. et al., "Cyclic AMP–Dependent Phosphorylation of a Brain Inositol Triphosphate Receptor Decreases its Release of Calcium," *PNAS (USA)* 85:8747–8750 (1988).

Tatro, J.B. et al., "Specific Receptors for α–Melanocyte–Stimulating Hormone are Widely Distributed in Tissues of Rodents," *Endocrinol.* 121:1900–1907 (1987).

Tatro, J.B., "Melanotropin Receptors of the Brain," *Meth. Neurosci.* 11:87–104 (Academic Press, NY 1993).

Tsonis, P.A. et al., "Rapid Phage DNA Isolation without the Use of Enzymes," *Biotechniques* 6:950–951 (1988).

Tsujimoto, Y. et al., "Analysis of the Structure, Transcripts, and Protein Products of bcl–2, the Gene Involved in Human Follicular Lymphoma," *PNAS (USA)* 83:5214–5218 (1986).

Van Sande, J. et al., "Thyrotropin Activates Both the Cyclic AMP and the $PIP_2$ Cascades in CHO Cells Expressing the Human cDNA of TSH Receptor," *Mol. Cell Endo* 74:R1–R6 (1990).

Verhaagen, J. et al., "Pharmacological Aspects of the Influence of Melanocortins on the Formation of Regenerative Peripheral Nerve Sprouts," *Peptides* 8:581–584 (1987).

Versteeg, D.H.G. et al., "ACTH–(1–24) and α–MSH Antagonize Dopamine Receptor–Mediated Inhibition of Striatal Dopamine and Acetylcholine Release," *Life Sci.* 38:835–840 (1986).

Walker, J.M. et al., "Evidence for Homologous Actions of Pro–Opiocortin Products," *Science* 210:1247–1249 (1980).

Wilson, J.F., "Levels of α–Melanotrophin in the Human Fetal Pituitary Gland Throughout Gestation, in Adult Pituitary Gland and in Human Placenta," *Clin Endocrinol.* 17:233–242 (1982).

Woodchuck, E.A., "Adrenocorticotropic Hormone Inhibits Angiotensin II–Stimulated Inositol Phosphate Accumulation in Rat Adrenal Glomerulosa Cells," *Mol. Cell. Endo.* 63;247–253 (1989).

Wreggett, K.A. et al., "Rapid Separation Method for Inositol Phosphates and Their Isomers," *Biochem. J.* 245:655–660 (1987).

The Fast Track mRNA Isolation Kit Instructions. (1993).

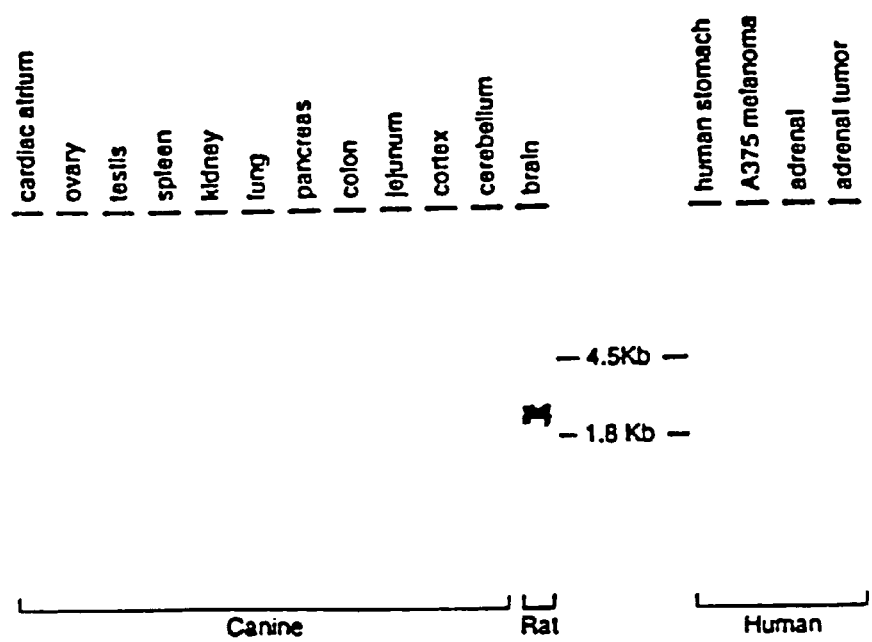

Figure 6

α-MSH　　　　　　　　　　　　　　　　　Ala Ser Tyr Ser | Met Glu His Phe Arg Trp Gly Lys Pro Val

β-MSH　Ala Glu Lys Lys Asp Glu Gly Pro Tyr Arg | Met Glu His Phe Arg Trp Gly Ser Pro Pro Lys Asp

γ-MSH　　　　　　　　　　　　　　　　　Tyr Val Met Gly His Phe Arg Trp Asp Arg Phe Gly

ACTH 1-10　　　　　　　　　　　　　　Ser Tyr Ser | Met Glu His Phe Arg Trp Gly

ACTH 4-10　　　　　　　　　　　　　　　　　　　Met Glu His Phe Arg Trp Gly

ACTH 1-13　　　　　　　　　　　　　　Ser Tyr Ser | Met Glu His Phe Arg Trp Gly Lys Pro Val

ACTH 4-13　　　　　　　　　　　　　　　　　　　| Met Glu His Phe Arg Trp Gly Lys Pro Val

Pro¹¹ γMSH　　　　　　　　　　　　　　Tyr Val Met Gly His Phe Arg Trp Asp Arg Pro Gly

Phe¹ γMSH　　　　　　　　　　　　　　Phe Val Met Gly His Phe Arg Trp Asp Arg Phe Gly

Thr¹ γMSH　　　　　　　　　　　　　　Thr Val Met Gly His Phe Arg Trp Asp Arg Phe Gly

Thr¹,Pro¹¹ γMSH　　　　　　　　　　　Tyr Val Met Gly His Phe Arg Trp Asp Arg Pro Gly

MELANOCORTIN RECEPTOR POLYPEPTIDES MC-3, MC-4, AND MC-5

This is a divisional of U.S. patent application Ser. No. 08/200,711, filed Feb. 17, 1994, now U.S. Pat. No. 5,622,860.

Work on this invention was supported in part by National Institutes of Health Grants RO1DIC34306 and RO1DK33500, and funds from the University of Michigan Gastrointestinal Peptide Research Center (National Institutes of Health Grant P300K34933). The Government has certain rights in this invention.

FIELD OF THE INVENTION

The present invention relates generally to melanocortin receptors and, more specifically, to novel genes encoding melanocortin receptors.

| GENE | ACCESSION NO. |
|---|---|
| Melanocortin-3 Receptor | L06155 |
| Melanocortin-4 Receptor | L08603 |
| Melanocortin-5 Receptor | L22527 |

BACKGROUND OF THE INVENTION

Melanocortins, products of pro-opiomelanocortin (POMC) post-translational processing, are known to have a broad array of physiological actions. Nakanishi, S. et al., *Nature* 278:423427 (1979). Aside from their well known effects on adrenal cortical functions (adrenocorticotropic hormone, ACTH) and on melanocytes (melanocyte stimulating hormone, MSH), melanocortins have been shown to affect behavior, learning, memory, control of the cardiovascular system, analgesia, thermoregulation, and the release of other neurohumoral agents including prolactin, luteinizing hormone, and biogenic amines. De Wied, D. et al., *Methods Achiev. Exp. Pathol.* 15:167–199 (1991); De Wied, D. et al., *Physiol. Rev.* 62:977–1059 (1982); Gruber, K. A. et al., *Am. J. Physiol.* 257:R681–R694 (1989); Murphy, M. T. et al., *Science* 210:1247–1249 (1980); Murphy, M. T. et al., *Science* 221:192–193 (1983); Ellerkmann, E. et al., *Endocrinol.* 130:133–138 (1992) and Versteeg, D. H. G. et al., *Life Sci.* 38:835–840 (1986). Peripherally, melanocortins have been identified to have immunomodulatory and neurotrophic properties, and to be involved in events surrounding parturition. Cannon, J. G. et al., *J. Immunol.* 137:2232–2236 (1986); Gispen, W. H., *Trends Pharm. Sci.* 11:221–222 (1992); Wilson, J. F., *Clin. Endocrinol.* 17:233–242 (1982); Clark, D. et al., *Nature* 273:163–164 (1978) and Silman, R. E. et al., *Nature* 260:716–718 (1976). Furthermore, melanocortins are present in a myriad of normal human tissues including the brain, adrenal, skin, testis, spleen, kidney, ovary, lung, thyroid, liver, colon, small intestine and pancreas. Tatro, J. B. et al., *Endocrinol.* 121:1900–1907 (1987); Mountjoy, K. G. et al., *Science* 257:1248–1251 (1992); Chhajlani, V. et al., *FEBS Lett.* 309:417–420 (1992); Gantz, I. et al. *J. Biol. Chem.* 268:8246–8250 (1993) and Gantz, I. et al., *J. Biol. Chem.* 268:15174–15179 (1993).

Recent studies have described an unexpected diversity of subtypes of receptors for the melanocortin peptides and determined that they all belong to the superfamily of seven transmembrane G-protein linked cell surface receptors. Mountjoy, K. G. et al., *Science* 257:1248–1251 (1992); Chhajlani, V. et al., *FEBS Lett.* 3:417–420 (1992); Gantz, I., *J. Biol. Chem.* 268:8246–8250 (1993) and Gantz, I. et al., *J. Biol. Chem.* (in press 1993). Although no ligand binding experiments were described, Mountjoy, K. G. et al., reported the gene sequences encoding the α-MSH receptor and the ACTH receptor. *Science* 257:1248–1251 (1992). Independently, Chhajlani, V. et al., reported a similar sequence for the α-MSH receptor and demonstrated specific binding of a stable MSH analogue to Cos-7 cells transfected with α-MSH receptor cDNA. *FEBS Lett.* 309:417–420 (1992). The α-MSH receptor has been identified as the melanocortin-1 receptor and the adrenocorticotropic hormone (ACTH) receptor as the melanocortin-2 receptor.

It would thus be desirable to isolate genes encoding melanocortin receptors. It would also be desirable to locate the chromosomal position of the melanocortin receptor genes. It would further be desirable to characterize melanocortin receptor binding and secondary signaling and determine tissue distribution of the melanocortin receptors. It would also be desirable to provide therapeutic vehicles for the treatment of processes involving the function of melanocortin receptors.

SUMMARY OF THE INVENTION

Five genes encoding the melanocortin-1, melanocortin-2, melanocortin-3, melanocortin-4 and melanocortin-5 receptors are set forth herein. The nucleic acid sequence of the gene encoding the human melanocortin-1 (MC1) receptor and its deduced 317 amino acid sequence are set forth in Sequence Listing ID Nos. 1 and 2, respectively. The nucleic acid sequence of the gene encoding human melanocortin-2 (MC2) receptor and its deduced 297 amino acid are set forth in Sequence Listing ID Nos. 3 and 4, respectively. The nucleic acid sequence of the gene encoding the human melanocortin-3 (MC3) receptor and its deduced 360 amino acid sequence, are set forth in Sequence Listing ID Nos. 5 and 6, respectively. The nucleic acid sequence of the gene encoding the human melanocortin-4 (MC4) receptor and its deduced 332 amino acid sequence, are set forth in Sequence Listing ID Nos. 7 and 8, respectively. The nucleic acid sequence of the gene encoding the mouse melanocortin-5 (mMC5) receptor and its deduced 326 amino acid sequence are set forth in Sequence Listing ID Nos. 9 and 10, respectively. The GenBank accession number for the MC3, MC4 and mMC5 receptor genes are LO6155, LO8603 and L22527, respectively.

The MC1 and MC2 receptor genes were previously described by Mountjoy, K. G., et al., in *Science* 257:1248–1251 (1992) and the MCI receptor gene was also described by Chhajlani, V. et al., in *FEBS Lett.* 3:417–420 (1992). However, the nucleic and amino acid sequences set forth herein for the MC1 receptor differ from those previously described. More specifically, the sequences for the MC1 receptor herein differ from the sequences set forth in Chhajlani et al. in five nucleotide and two amino acid positions and differ from the sequences set forth in Mountjoy et al. in two nucleotide and two amino acid positions. The chromosomal localization of the MC1 and MC2 receptor genes is also disclosed herein. The MC1 receptor gene is localized to 16q24.3 and the MC2 receptor gene is localized to 18p11.2.

The receptors encoded by the MC3, MC4 and mMC5 receptor genes have also been characterized and the MC3 and MC4 receptor genes localized. More specifically, the MC3 receptor is activated primarily by the core heptapeptide sequence of the melanocortins with an adjacent carboxyl terminal tyrosine (Tyr$^2$) being required for full activation. It is expressed in brain, placenta and gut tissues and the MC3 receptor gene was localized to chromosome loci 20q13.2–q13.3. The MC4 receptor is activated by amino acids in the carboxyl and amino terminal portions of the peptide, in particular $Tyr^2$ and $Pro^{12}$, with the core heptapeptide sequence being of lesser importance. It is expressed primarily in brain and its expression is notably absent in the adrenal cortex, melanocytes and placenta. The MC4 receptor gene was localized to chromosome 18q21.3. It was also determined that an amino terminal tyrosine and carboxyl terminal proline are determinates in the activation of the mouse mMC5 receptor, whereas the melanocortin core heptapeptide sequence is devoid of pharmological activity. The mMC5 receptor is expressed in lung, spleen and skeletal muscle. As discussed in detail below, the gene sequences, tissue distribution, and the profiles of the responses of the MC3, MC4 and mMC5 receptors to different melanocortins distinguish them from other melanocortin receptors as well as from each other.

Intracellular signalling pathways are also described herein. More specifically, it has been shown that the MC3 receptor is coupled to both cAMP and inositol phospholipid/$Ca^{++}$ mediated post-receptor signaling systems. A chimeric receptor cH2R/hMC3R-3i constructed for these studies is also provided herein. The present invention further provides the means to obtain an isolated protein which is a melanocortin receptor. The invention also provides the means to obtain antibodies directed at the melanocortin receptors described herein. Furthermore, the invention provides a method for detecting the presence of melanocortin receptors on cell surfaces. Likewise, the invention also provides a method for determining whether a ligand which is not known to be capable of binding to the melanocortin receptors described herein can bind to the respective receptor. The invention further provides a method of screening drugs to identify drugs which specifically interact with and bind to or effect the secondary signaling of melanocortin receptors.

It will be appreciated that therapeutic interventions addressing both normal physiological and pathophysiological processes which utilize the melanocortin receptors, the genes encoding these receptors and the distribution and characterization information set forth herein, are also contemplated.

Additional objects, advantages, and features of the present invention will become apparent from the following description and appended claims, taken in conjunction with the accompanying drawings.

BRIEF DESCRIPTION OF THE DRAWINGS

The various advantages of the present invention will become apparent to one skilled in the art by reading the following specification and subjoined claims and by referencing the following drawings in which:

FIGS. 1A and 1B are Northern blots showing tissue distribution of the MC4 receptor;

FIG. 6 (Sequence Listing ID Nos. 13–23) shows the core heptapeptide amino acids of various melanocortins;

FIGS. 18A, 18B, 18C and 18D are a set of graphs showing dose-response curves for histamine stimulated changes in cAMP content and [$^3$H] IP production in Hepa cells wherein FIGS. 18A and 18C depict cells transfected with wild type cH2R and FIGS. 18B and 18D depict cells transfected with the chimeric cH2R/hMC3R-3i.

DESCRIPTION OF SEQUENCE LISTINGS

Figure 2A:
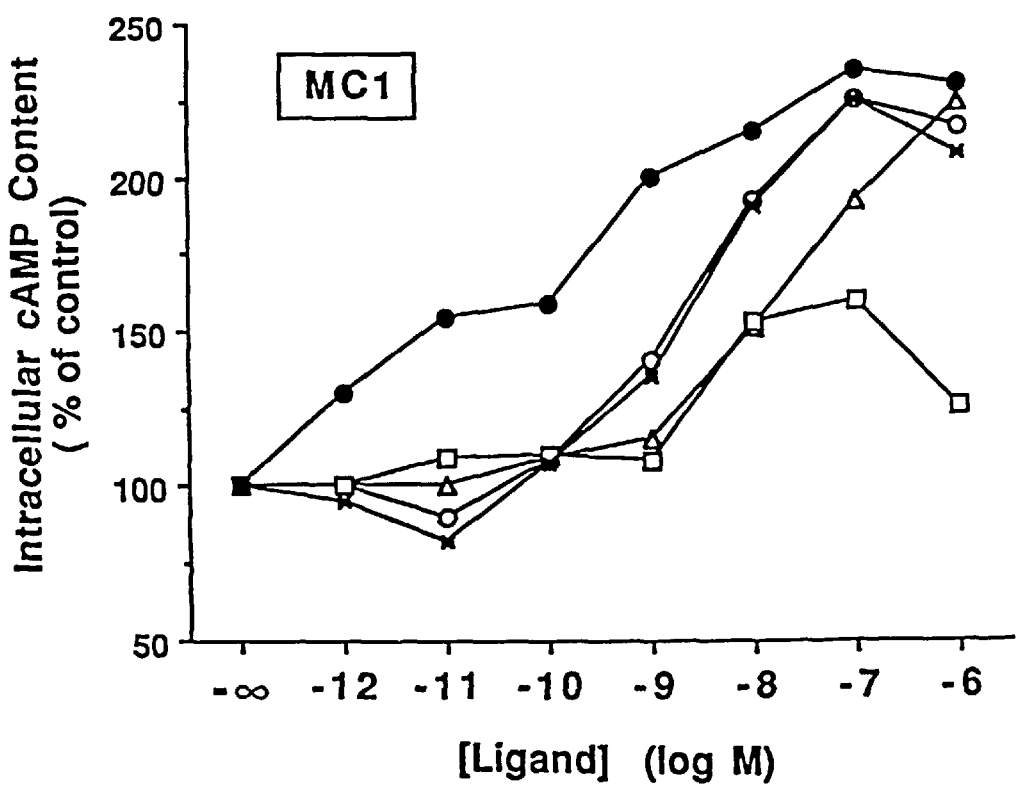
FIGS. 2A and 2B are graphs showing the generation of cAMP in L-cells transfected with the MC1 and MC3 receptor genes, respectively, in response to various melanocortins.

Sequence Listing ID No. 1 is the nucleotide sequence of DNA encoding the melanocortin-1 receptor.

Sequence Listing ID No. 2 is the deduced amino acid sequence of the melanocortin-1 receptor.

Sequence Listing ID No. 3 is the nucleotide sequence of DNA encoding the melanocortin-2 receptor.

Sequence Listing ID No. 4 is the deduced amino acid sequence of the melanocortin-2 receptor.

Sequence Listing ID No. 5 is the nucleotide sequence of DNA encoding the melanocortin-3 receptor.

Sequence Listing ID No. 6 is the deduced amino acid sequence of the melanocortin-3 receptor.

Sequence Listing ID No. 7 is the nucleotide sequence of DNA encoding the melanocortin-4 receptor.

Sequence Listing ID No. 8 is the deduced amino acid sequence of the melanocortin-4 receptor.

Sequence Listing ID No. 9 is the nucleotide sequence of DNA encoding the melanocortin-5 receptor.

Sequence Listing ID No. 10 is the deduced amino acid sequence of the melanocortin-5 receptor.

Sequence Listing ID No. 11 is the nucleotide sequence of an oligonucleotide used as a 5' PCR primer.

Sequence Listing ID No. 12 is the nucleotide sequence of an oligonucleotide used as a 3' PCR Primer.

DETAILED DESCRIPTION OF THE PREFERRED EMBODIMENTS

Five sequences encoding the human melanocortin-1 (MC1), melanocortin-2 (MC2), melanocortin-3 (MC3), melanocortin-4 (MC4) and mouse melanocortin-5 (mMC5) receptors have been cloned and sequenced. Their nucleic acid and corresponding amino acid sequences are set forth in Sequence Listing ID Nos. 1–10. The MC1 and MC2 receptor genes have been localized to chromosome 16q24.3 and 18p11.2, respectively. The MC3 receptor gene was localized to chromosome loci 20q13.2–q13.3. The MC4 receptor gene was localized to chromosome 18q21.3.

The MC3 receptor is primarily activated by the heptopeptide core of melanocortins. It is expressed in brain, placenta and gut tissues. The MC4 receptor is activated by amino acids in the carboxyl and amino terminal portions of the peptide. It is expressed primarily in brain and its expression is notably absent in the adrenal cortex, melanocytes and placenta. The mMC5 receptor is also activated by amino acids in the carboxyl and amino terminal portions of the peptide and is expressed in lung, spleen and skeletal muscle. As discussed in detail below, the gene sequences, tissue distribution and the profiles of the responses of the MC3, MC4 and MC5 receptors to different melanocortins distinguish them from other melanocortin receptors as well as from each other.

The MC1 and MC2 receptor genes have been previously described in Mountjoy, K. G., et al., in *Science* 257:1248–1251 (1992) and the MC1 receptor gene was also described by Chhajlani, V. et al., in *FEBS Lett.* 3:417–420 (1992). The nucleic and amino acid sequences for the MC1 receptor set forth herein differ from the sequences set forth in Mountjoy et al. in two nucleotide and two amino acid positions. Likewise, the MC1 receptor sequences of the present invention differ from the sequences set forth in Chhajlani et al. in five nucleotide and three amino acid positions.

It will be appreciated that the nucleic and amino acid sequences of the present invention can include some variation from the sequences represented by and complementary to the sequences set forth in the Sequence Listing but must be substantially represented by or complementary to those set forth therein. By "substantially represented by" or "substantially complementary to" is meant that any variation therein does not impair the functionality of the sequence to any significant degree. As used herein, the term "nucleic acid" is intended to mean natural and synthetic linear and sequential arrays of nucleotides and nucleosides, e.g. in cDNA, genomic DNA (gDNA), mRNA, and RNA, oligonucleotides, oligonucleosides and derivatives thereof. It will also be appreciated that such nucleic acids can be incorporated into other nucleic acid chains referred to as "vectors" by recombinant-DNA techniques such as cleavage and ligation procedures. The terms "fragment" and "segment" are as used herein with reference to nucleic acids (e.g., cDNA, genomic DNA, i.e., gDNA) are used interchangeably to mean a portion of the subject nucleic acid such as constructed artificially (e.g. through chemical synthesis) or by cleaving a natural product into a multiplicity of pieces (e.g. with a nuclease or endonuclease to obtain restriction fragments). As used herein, "A" represents adenine; "T" represents thymine; "G" represents guanine; and "C" represents cytosine; except where otherwise indicated.

As referred to herein, the term "encoding" is intended to mean that the subject nucleic acid may be transcribed and translated into the subject protein in a cell, e.g. when the subject nucleic acid is linked to appropriate control sequences such as promoter and enhancer elements in a suitable vector (e.g. an expression vector) and when the vector is introduced into a cell. The term "polypeptide" is used to mean three or more amino acids linked in a serial array.

The term "capable of hybridizing under stringent conditions" is used to mean annealing a first nucleic acid to a second nucleic acid under stringent conditions (defined below). For example, the first nucleic acid may be a test sample, and the second nucleic acid may be the sense or antisense strand of a melanocortin receptor gene of the present invention. Hybridization of the first and second nucleic acids is conducted under stringent conditions, e.g. high temperature and/or low salt content, which tend to disfavor hybridization in 6 X SSC, at 42° C. in aqueous solution followed by washing with 1 X SSC, at 55° C. in aqueous solution. (Other experimental conditions for controlling stringency are described in Maniafis, T. et al., *Molecular Cloning; A Laboratory Manual*, Cold Springs Harbor Laboratory, Cold Springs, N.Y., 1982 at pages 387–389 and also Sambrook, Fritsch, and Maniatis, *Molecular Cloning; A Laboratory Manual, Second Edition*, Volume 2, Cold Springs Harbor Laboratory, Cold Springs, N.Y., 1989, pages 8.46–8.47, both of which are herein incorporated by reference).

The Specific Examples set forth below further describe the present invention. In particular, Specific Example I describes the isolation and cloning of the melanocortin receptors. For the initial gene isolation experiments, total RNA obtained from HeLa cells and U937 cells via the acid guanidiniym thiocyanatephenol-chloroform method were reverse transcribed using avian myeloblastoma virus reverse transcriptase. Chomczynski, P. et al., *Anal. Biochem.* 162:1900–1907 (1987). The cDNAs thus obtained functioned as templates for the polymerase chain reaction (PCR) primed with oligonucleotides based on homologous regions of the third and sixth transmembrane domains of G-protein linked receptors as previously described. Libert, R. et al., *Science* 244:569–572 (1989). The DNA obtained by PCR was cut with an appropriate restriction enzyme corresponding to the linker portion of the oligonucleotide and then electrophoresed. DNA bands were excised from the gel and subcloned directly into the M13 sequencing vector. Dideoxynucleotide sequencing was then performed. Initial PCR experiments resulted in the isolation of DNA fragments encoding two novel G-protein linked receptors. These receptors were subsequently identified as the melanocortin-1 (MC1) and melanocortin-3 (MC3) receptors. Oligonucleotides based on highly conserved sequences in the second intracytoplasmic loop and the seventh transmembrane domain of these two receptors were subsequently constructed to search for other members of this receptor gene family. Using both human and murine genomic DNA as substrate for further PCR reactions, three additional gene fragments encoding members of this novel receptor family were isolated using these latter primers. These DNA fragments were subsequently used to isolate the melanocortin-2 (MC2), melanocortin-4 (MC4), and melanocortin-5 (MC5) receptors.

In Specific Example II, expression confirming the identification of the melanocortin receptors is described. For these experiments, the coding regions of the receptors were subcloned into the eukaryotic expression vector CMVneo using the PCR according to methods previously described for receptor expression studies. Brown, N. A. et al., *J. Biol. Chem.* 265:13181–13189 (1990) and Gantz, I. et al., *PNAS (USA)* 88:429–433 (1991). Various cells lines were transfected using a calcium phosphate co-precipitation method or lipofection. Chen, C. A. et al., *Biotechniques* 6:632–638 (1988) and Feigner, P. L. et al., *PNAS (USA)* 84:7413–7414 (1987). The transiently or stably transfected cell lines served as the substrate for the detailed pharmacological studies and investigations of secondary messenger signal transduction.

In Specific Example II, the tissue distribution of the MC3, MC4 and mMC5 receptors is also described. For characterization of the tissue distribution of these receptors, Northern blot analysis, PCR, and in situ hybridization were used. By Northern blot analysis and PCR/Southern it was found that the MC3 receptor is present in brain, placental, and gut tissues and by Northern blot analysis it was found that the MC4 receptor is limited to brain. In situ hybridization of rodent brain sections with probes specific for the MC3 and MC4 receptors revealed that these receptors are present in the cortex, thalamus, hypothalamus, and hippocampus of the brain. Also by Northern blot analysis, it was found that mMC5 receptor is present in mouse lung, spleen and skeletal muscle.

In Specific Example III, pharmacological experiments examining the structure and activity of the receptors are described. It was found that the MC3 receptor is capable of recognizing the core heptapeptide sequence shared by all the melanocortin peptides (Met-Glu-His-Phe-Arg-Tyr-Gly; Sequence Listing ID No. 17), and hence responds to all melanocortins with equal potency and efficacy. It was also found that adjacent amino acids of the melanocortin peptides are of primary importance. Experiments were also performed on the MC3 and MC4 receptors with synthetic melanocortin peptides containing specific amino acid substitutions which confirmed the above pharmacological results. The MC3 receptor is activated primarily by the core heptapeptide sequence of melanocortins with an adjacent carboxyl terminal tyrosine ($Tyr^2$) being required for full activation. The MC4 receptor is activated by amino acids in the carboxyl and amino terminal portions of the peptide (especially $Tyr^2$ and $Pro^{12}$) with the core heptapeptide sequence being of lesser import. It was also determined that an amino terminal tyrosine and carboxyl terminal proline are determinates in the activation of the mMC5 receptor whereas the melanocortin core heptapeptide sequence is devoid of pharmalogical activity. The physiological studies of the cloned receptors have uncovered unique aspects regarding the regulation of the pathways of signal transduction used by these receptors. It will thus be appreciated to those skilled in the art that subtype specific drugs are also contemplated by the present invention.

In Specific Example IV, experiments demonstrating the intracellular signalling mechanisms activated by melanocortin receptors are described. A chimeric receptor cH2R/ hMC3R-3, constructed for these studies is also described herein. These experiments indicate that the MC3 receptor is coupled to both CAMP and inositol phospholipid/$Ca^{++}$ mediated post-receptor signalling systems. Such information is useful to determine normal, abnormal and altered functioning of the receptor.

In Specific Example V, chromosomal localization of the human melanocortin receptor genes is described. It was found that the MC1 receptor gene is localized to 16q24.3, the MC2 receptor gene is localized to 18p.11.2, the MC3 receptor gene is localized to 20q13.2–q13.3 and the MC4 receptor gene is localized to 18q21.3. This information provides the ability to determine abnormalities such as translocations in the genes which encode the receptors by using well known hybridization techniques.

It will be appreciated that the genes of the present invention encode for proteins which, by using methods well known in the art, can be isolated. Examples of such proteins are those having substantially the same amino acid sequences as the amino acid sequences set forth in the Sequence Listing. A method for obtaining an isolated melanocortin receptor is by expressing DNA encoding the receptor in a suitable host, such as a bacterial, yeast, or mammalian cell, and recovering the melanocortin receptor after it has been expressed in such a host.

This invention also provides an antibody directed to a melanocortin receptor of the present invention. Such an antibody may be serum-derived or monoclonal and may be prepared using methods well known in the art. For example, cells may be used as immunogens to raise such an antibody. Alternatively, synthetic peptides may be prepared using commercially available machines and the amino acid sequences shown in the Sequence Listing. As a still further alternative, DNA, such as a cDNA or a fragment thereof, may be cloned and expressed and the resulting polypeptide recovered and used as an immunogen. One example of such an antibody is a monoclonal antibody directed to an epitope of the melanocortin receptor present on the surface of a cell and having an amino acid sequence substantially the same as any part of one amino acid sequence set forth in the Sequence Listing.

Still further, this invention provides a method of detecting the presence of a melanocortin receptor on the surface of a cell. This method comprises contacting the cell with a monoclonal or serum-based antibody directed to an exposed epitope on the melanocortin receptor under conditions permitting binding of the antibody to the melanocortin receptor, and detecting the presence of the antibody bound to the cell, and thereby the presence of the melanocortin receptor on the surface of the cell. Such a method is useful in determining whether a given cell is defective relative to the expression of melanocortin receptors on the surface of the cell.

It will also be appreciated that the present invention provides vectors capable or adapted for expression in a bacterial, yeast, or mammalian cell which comprise DNA encoding one of the melanocortin receptors of the present invention or DNA or cDNA having a coding sequence substantially the same as any one of the coding sequences set forth in the Sequence Listing and the regulatory elements necessary to express such DNA in the bacterial, yeast, or mammalian cell. With respect to the latter, those skilled in the art will readily appreciate that numerous vectors may be constructed utilizing existing plasmids, viruses, bacteriophages and the like and adapted as appropriate by methods known to those skilled in the art to contain regulatory elements necessary to express the DNA in the mammalian cell. Numerous mammalian cells may be used including, for example, the mouse fibroblast cell NIH3T3, L-cells, CHO cells, HeLa cells, Hepa cells and COS-1 cells. DNA encoding a melanocortin receptor may be otherwise introduced into mammalian cells, e.g. by calcium phosphate coprecipitation, to obtain mammalian cells which comprise DNA, e.g., cDNA or a vector encoding the receptor.

It will further be appreciated that the invention also provides a method of detecting the presence of mRNA coding for the melanocortin receptors of the present invention in a cell. This method comprises obtaining total mRNA from the cell by using methods well known in the art, and contacting the mRNA so obtained with cDNA having a coding sequence substantially the same as one of the coding sequences of the genes of the present invention under hybridizing conditions, detecting the presence of mRNA hybridized to the cDNA, and thereby detecting the presence of mRNA coding for the melanocortin receptor in the cell.

This invention additionally provides a DNA probe useful for detecting, in a sample, a nucleic acid encoding the melanocortin receptor. Such a probe comprises a nucleic acid molecule of at least about 17–21 nucleotides having a sequence complementary to a sequence included within the nucleic acid sequences set forth in the Sequence Listing. Such nucleic acid probe technology is well known to those skilled in the art who will readily appreciate that such probes may vary greatly in length and may comprise a detectable label, such as a radioisotope or fluorescent dye, to facilitate detection of the probe.

The present invention also provides a method for determining whether a ligand, such as a known or putative drug, which is not known to be capable of binding to melanocortin receptors of the present invention, can bind to the receptors. This method comprises contacting a mammalian cell with the ligand under conditions permitting binding of ligands previously known to bind to the melanocortin receptors and detecting the presence of any of the ligand bound to the receptors. An example of a mammalian cell is a mammalian cell comprising a vector which comprises a DNA molecule encoding a melanocortin receptor of the present invention, or DNA or cDNA molecules having coding sequences substantially the same as one of the coding sequences shown in the Sequence Listing. Also, the present invention provides a method of screening drugs to identify drugs which specifically interact with, and bind to, a melanocortin receptor on the surface of a cell. This method comprises contacting a mammalian cell which is expressing a melanocortin receptor with a plurality of drugs, known or putative, determining those drugs which bind to the mammalian cells, and thereby identifying those drugs which bind to the mammalian cell, and thereby identifying drugs which specifically interact with, and bind to, the melanocortin receptor.

The following Specific Examples further describe the present invention.

SPECIFIC EXAMPLE 1

ISOLATION

Materials and Methods

Polymerase Chain Reaction (PCR). Total RNA obtained from HeLa cells (a human cervical cancer cell line) and U937 cells (a human histiocytic lymphoma cell line) via the acid guanidinium thiocyanate-phenol-chloroform method of Chomczynski, P. et al., *Anal. Biochem.* 162:156–159 (1987) was reverse transcribed using avian myeloblastoma virus reverse transcriptase. The cDNAs thus obtained functioned as templates for polymerase chain reactions primed with oligonucleotides based on homologous regions of the third and sixth transmembrane domains of G protein-linked receptors as described by Libert, R. et al., *Science* 244:569–572 (1989) and Gantz, I. et al. *PNAS (USA)* 88:429–433 (1991). Initially two partial length DNA clones for G protein-linked receptors were isolated, and these were utilized to obtain full-length genomic clones by screening a genomic library as described below. Highly conserved sequences in the second intracytoplasmic loop and the seventh transmembrane domain of these receptors served as the basis for constructing oligonucleotides to be used to search for other members of this receptor gene family (5' PCR primer TACGCA/GCTG/CCGCTACCACAGCATC) (Sequence Listing ID No. 11) and 3' PCR primer GAAG/AGCA/GTAT/GATGAA/GG/TGGGTCA/GAT) (Sequence Listing ID No. 12). Oligonucleotides were synthesized by the Molecular Biology Core of the University of Michigan Gastrointestinal Peptide Research Center using an Applied Biosystems model 380B DNA synthesizer. The conditions for the PCR were as follows: denaturation for 1.5 min at 94° C., annealing for 2 min at 45° C., and extension for 4 min at 72° C. The reaction was carried out for 30 cycles, and then 20% of the product was added to fresh buffer and enzyme and subjected to an additional 30 cycles. The final reaction products were phenol-extracted and ethanol-precipitated. The DNA was cut with an appropriate restriction enzyme corresponding to the linker portion of the oligonucleotide and then electrophoresed on a 1% NuSieve, 1% Seaplaque gel (FMC, Rockland, Md.). DNA bands were cut out of the gel and subcloned directly into the M13 sequencing vector. Dideoxynucleotide sequencing was then performed using Sequenase version 2 (United States Biochemical Corp.).

Genomic Cloning. Partial length PCR-derived clones obtained as described above were random-primed with $^{32}$P and used as probes to screen a human and a mouse EMBL3 phage library (Clontech, Palo Alto, Calif.). Under hybridization [6×SSC (0.9 M NaCl, 90 mM sodium citrate, pH 7.0), 5×Denhardt's solution (0.1% Ficoll, 0.1% polyvinylpyrrolidone, 0.1% bovine serum albumin), 0.1 M Hepes, pH 7.0 100 μg/ml salmon sperm, 10 mg/ml dextran sulfate at 55° C.] and wash conditions (successive washes with 6×SSC, 4×SSC, and 2×SSC at 50° C.) single clones were isolated. Phage DNA preparations were made by the plate lysate method as described in Taonis, P. A. et al., *Bio/Techniques* 6:950–951 (1988), and the inserts were restriction-mapped and examined by Southern blot analysis. Dideoxynucleotide sequencing of fragments containing the receptor coding regions subcloned into M13 was then performed.

Results

Melanocortin-1 Receptor. The melanocortin-1 (MC1) receptorgene encodes for a protein 317 amino acids in length. The nucleotide and deduced amino acid sequences of the MC1 receptor are set forth in Sequence Listing ID Nos. 1 and 2, respectively. Receptors having the greatest degree of homology with the melanocortin receptor family are those of the adenosine and catecholamine receptor families. The nucleotide sequence obtained for MC1 receptor differed from that reported by Mountjoy, K. G. et al., in *Science* 257:1248–1251 (1992), in two nucleotide and two amino acid positions, and from that reported by Chhajlani, V. et al., in *FEBS Lett.* 309:417–420 (1992), in five nucleotide and three amino acid positions. Specifically, at nucleotide positions 485 and 488 of the MC1 receptor gene, Mountjoy et al.

disclose guanine and adenine, respectively, rather than cytocine and guanine as disclosed herein. Mountjoy et al., therefore, disclose proline and arginine at amino acid positions 162 and 163, respectively, rather than arginine and glutamine as disclosed herein. At nucleotide positions 269, 270, 488, 490 and 491 Chhailani et al. disclose guanine, cytosine, guanine, cytosine and guanine respectively, rather than cytosine, guanine, adenine, guanine and cytosine as described herein. Chhajlani et al., therefore, disclose serine, arginine and arginine at amino acid positions 90, 163 and 164, respectively, rather than threonine, glutamine and alanine as disclosed herein. Comparison of several amino acid sequences of melanocortin receptors are shown in Gantz I. et al., *J. Biol. Chem.* 268:8246–8250 (1993).

Melanocortin-2 Receptor. The melanocortin-2 (MC2) receptor gene encodes for a protein 297 amino acids in length. The nucleotide and deduced amino acid sequence of MC2 receptor are set forth in Sequence Listing ID Nos. 3 and 4, respectively.

Melanocortin-3 Receptor. The melanocortin-3 (MC3) receptor gene is an intronless gene encoding an apparent seven-transmembrane-spanning protein of 360 amino acids in length. Sequencing Listing ID Nos. 5 and 6 represent the nucleotide and deduced amino acid sequences, respectively, of the MC3 receptor gene. As shown in Gantz et al., *J. Biol. Chem.* 268:8246–8250 (1993), the MC3 receptor shares approximately 60% nucleotide sequence homology and 45% amino acid homology with the MC1 receptor and MC2 receptor.

Melanocortin-4 Receptor. The melanocortin-4 (MC4) receptor gene is an intronless gene encoding a protein of 332 amino acids in length and with apparent seven transmembrane topography. As shown in Gantz, I., et al., *J. Biol. Chem.* 268:15174–15179 (1993), the MC4 receptor is structurally most similar to the MC3 receptor with which it shares 58% and 76% overall amino acid identity and similarity, respectively. Sequence Listing ID Nos. 7 and 8 represent the nucleotide and deduced amino acid sequences of the MC4 receptor, respectively.

Melanocortin-5 Receptor. The mouse melanocortin-5 (mMC5) receptor gene encodes a protein of 325 amino acids in length. Sequence Listing ID Nos. 9 and 10 represent the nucleotide and deduced amino acid sequences of the mMC5 receptor, respectively. The highest overall homology of this receptor is to the human MC4 receptor with which it shares 63.7% amino acid identity and 77.6% amino acid similarity. Deduced amino acid sequences of rodent melanocortin receptors have been published only for the mouse melanocortin-1 receptor (mMC1 receptor or murine α-MSH receptor), Mountjoy, K. G., et al., *Science* 257:1248–1251 (1992), and the rat melanocortin-3 (rMC3) receptor, Roselli-Rehfuss, L., et al., *PNAS* 90:8856–8860 (1993). By comparison to their human melanocortin receptor counterparts, these mouse receptors share considerably greater sequence homology within a single receptor subtype than they do to each other.

SPECIFIC EXAMPLE 2

EXPRESSION AND DISTRIBUTION

Materials and Methods

Receptor Expression. The coding regions of the receptors were subcloned into the eukaryotic expression vector CMV-neo as described in Brown, N. A. et al., *J. Biol. Chem.* 265:13181–13189 (1990) using the PCR according to methods previously described in Gantz, I., et al., *PNAS (USA)* 88:429–433 (1991). The sequences were subsequently checked by nucleotide sequencing to insure that no sequence errors were induced by PCR. L-cells (a mouse fibroblast-like cell line) were transfected using a calcium phosphate co-precipitation method as described in Chen, C. A. et al. *Bio/Techniques* 6:632–638 (1988). Permanently transfected L-cells were selected by resistance to the neomysin analogue G418, and receptor mRNA expression was checked by Northern blot analysis. A rat hepatoma cell line (Hepa) which lacks endogenous melanocortin receptors was also transfected with the CMVneo/MC3R and CMVneo/MC4R constructs. COS-1 cells which were transiently transfected with the CMVneo/MC4R gene construct by lipofection as described in Feigner, P. L. et al., *PNAS (USA)* 84:7413–7417 using the Lipofectin Reagent (Life Technologies Inc.) were split into 12-well plates after 24 hr and assayed 36 hr post-transfection.

Northern Blotting. Total RNA was extracted from cell lines and tissues using the acid guanidinium thiocyanate-phenol-chloroform method as described in Chomczynski, P. et al., *Anal. Biochem.* 162:156–159 (1987). Poly(A)$^+$ RNA was obtained using oligo(dT)-cellulose chromatography with the Poly(A) Quik mRNA isolation kit (Stratagene, La Jolla, Calif.). Alternatively some poly(A)$^+$ was obtained directly from tissue using the Fast Track kit (Invitrogen, San Diego, Calif.). A commercially available human multiple tissue Northern blot (Clontech, Palo Alto, Calif.) was also used. RNA was transferred to nitrocellulose and hybridized in 50% formamide, 5×SSPE (0.75M NaCl, 0.05 M $NaH_2PO_4$, 0.005 M $Na_2EDTA$, pH 7.4), 10×Denhardt's solution, 100 μg/ml salmon sperm DNA, and 2% sodium dioctyl sulfate for 18 hr according to standard methods. Sambrook, J. et al., *Molecular Cloning: A Laboratory Manual*, 2nd Ed., Cold Spring Harbor Laboratory, Cold Spring Harbor, N.Y. (1989). Human and rat tissues were hybridized at 42° C. using a random-primed $^{32}$P-labeled human or mouse probe, respectively. Canine tissue was hybridized with a rat probe at a lower temperature (40° C.) to compensate for cross-species sequencing mismatch. Blots were exposed to XAR-5 film for 24–72 hr.

PCR/Southern Blotting. RNA extracted by the acid guanidinium thiocyanate-phenol-chloroform method was treated with 50 units of RNase-free DNase I (Boehringer Mannheim) for 1 hr at 25° C., then reverse transcribed with avian myeloblastosis reverse transcriptase using oligo(dT)$_{12-18}$ as primer. Human stomach and duodenal mucosa cDNA thus generated was used as template for PCR using primer oligonucleotides specific for the 5'- and 3'- untranslated portions of the melanocortin receptor sequence. The primers used for the PCR reaction with rat pancreatic cDNA were the nonspecific second intracytoplasmic loop and seventh transmembrane oligonucleotides described above. Aside from the DNase treatment, the PCR reactions were controlled for possible genomic DNA contamination by conducting parallel reactions using RNA samples prior to reverse transcription as template. Similarly, PCR reactions were conducted with laboratory water as template to verify that there was no contamination of reagents from any source. Each PCR reaction was conducted over 30 or 60 cycles as described above. The products were electrophoresed on a 1% Nusieve, 1% Seaplaque gel, stained with ethidium bromide, and photographed under ultraviolet illumination. To verify that the bands obtained by PCR were generated from melanocortin receptor cDNA, they were transferred to nitrocellulose using standard Southern blotting techniques as described in Sambrook, J. et al., *Molecular Cloning: A*

*Laboratory Manual,* 2nd Ed., Cold Spring Harbor Laboratory, Cold Spring Harbor, N.Y. (1989). The coding region of the gene labeled with $^{32}P$ by random priming was then used to probe the blots under stringent hybridization (65° C.) and wash conditions (final wash 0.1×SSC at 65° C.). Blots were exposed to XAR-5 film for 3–6 hr at −80° C.

In Situ Hybridization. Adult male mice were sacrificed by cervical dislocation and their brains removed and frozen in liquid isopentane (−30° C.) for 30 seconds. Frozen tissue was sectioned on a Slee cryostat (15 μm), thaw-melted onto polylysine-coated slides, and stored at −80° C. For further investigations, slides were transferred directly to 4% buffered formaldehyde for 60 min at room temperature. Following 3 rinses in 2×SSC, the sections were treated with proteinase K (1 μg/ml in 100 mM Tris, pH 8.0, 50 mM EDTA) for 10 min at 37° C., then rinsed in water and treated with a mixture of 0.1 M triethanolamine, pH 8.0, and acetic anhydride (400:1, v/v) with stirring for 10 min. The sections were again rinsed in water, dehydrated through graded alcohols, and air-dried. As a control, prior to treatment with proteinase K, some sections were incubated with RNase A (200 μg/ml in 100 mM Trix, pH 8.0 and 0.5 M naCl) for 30 min at 37° C. All sections were hybridized with a $^{36}S$-UTP/$^{35}S$-CTP-labeled riboprobe generated from a 461-base fragment of the melanocortin receptor clone. cRNA probes were diluted in hybridization buffer (75% formamide, 10% dextran sulfate, 3×SSC, 50 mM $Na_2PO_4$, pH 7.4, 1×Denhardt's, 0.1 mg/ml yeast tRNA, 10 mM dithiothrietol) to a final concentration of $2\times10^6$ dpm/30 μl. After a 55° C. overnight hybridization, sections were rinsed in 2×SSC and treated with RNase A (200 μg/ml for 60 min at 37° C.). The slides were rinsed in 1×SSC, washed in 0.1×SSC at 68° C. for 90 min, rinsed in water, dehydrated in graded alcohols, and air-dried. Sections were then exposed to Kodak XAR-5 film for 10 days and developed.

Results

Melanocortin-3 Receptor. Tissue distribution further differentiates the MC3 receptor from the previously described α-MSH (melanocortin-1) and ACTH (melanocortin-2) receptors. As reported in Mountjoy, K. G. et al., *Science* 257:1248–1251 (1992) the MC1 receptor was expressed in melanoma cells but not in other tissues, whereas the MC2 receptor was expressed only in the adrenal gland. In contrast, demonstrated by Northern blot hybridization, the MC3 receptor is expressed in brain and placenta but not expressed in either melanoma cells or in adrenal tissue. Gantz et al., *J. Biol. Chem.* 268:8246–8250 (1993). Additionally, in situ hybridization demonstrated that the MC3 receptor is expressed in the cortex, thalamus, hippocampus, and hypothalamus. Gantz et al. supra. Thus the MC3 receptor may partake in mediating some of the putative actions of melanocortin peptides in higher cortical functions such as behavior. The magnitude of melanocortin-3 receptor expression in the placenta was remarkable. There have been conflicting reports concerning the presence of melanocortin peptides in the placenta as described by Krieger, D. T., *Biol. Reprod.* 26:55–71 (1982) and Clark, D. et al., *Nature* 273:163–164 (1978). However, α-MSH levels are known to rise markedly in the maternal circulation in late pregnancy as described by Clark, D. et al., supra, and a switch in sensitivity of the fetal adrenal gland from α-MSH to ACTH has been observed prior to parturition as described by Silman, R. E. et al., *Nature* 260:716–718 (1976) and Challis, J. R. G. et al., *Nature* 269:818–819 (1977). Whether the MC3 receptor plays a role in these changes may now be further examined. As the technique of Northern blotting is relatively insensitive in demonstrating low abundance mRNAs, a combination of PCR followed by Southern blotting of the reaction products was used to investigate MC3 receptor expression in several gut tissues and obtained positive signals from the stomach, duodenum, and pancreas. Gantz et al. supra. Although several bands were obtained from the PCR reactions only a single band hybridized on Southern blotting with the MC3 receptor probe.

Melanocortin-4 Receptor. As discussed above, the members of the melanocortin receptor family can be differentiated on the basis of their tissue distribution. While the MC1 receptor is localized to melanocytes and the MC2 receptor to adrenal cortical cells, the MC4 receptor is found primarily in the brain as shown in FIGS. 1A and 1B. Gantz et al., *J. Biol. Chem.* 268:15174–15179 (1993). FIGS. 1A and 1B depicts tissue distributions of the MC4 receptor as evidenced by Northern blotting with RNA extracted from various tissues. Furthermore, the blot in FIG. 1A represents 5 μg of canine poly($A^+$) RNA and in FIG. 1B, 35 μg of human total RNA from the tissues listed. In the brain, receptors can be demonstrated by in situ hybridization in regions of the thalamus, hypothalamus, and hippocampus; however, there are distinct differences in the patterns of their expression. The extensive labeling of the MC4 receptor in the CA1 and CA2 regions of the hippocampus is of particular interest in view of the purported central nervous system functions of melanocortins in learning and memory. Notably, the MC4 receptor is not expressed in the placenta (data not shown), a tissue that expresses the MC3 receptor in large amounts.

Melanocortin-5 Receptor. The tissue distribution of mMC5 receptor is unique among the melanocortin receptors. Using a random primed the mMC5 receptor probe and a mouse/rat multiple tissue Northern (MTN) blot (Clontech, Palo Alto, Calif.), extraordinarily high levels of expression in skeletal muscle and substantial expression in spleen and lung were detected. Gantz, I. et al., "Molecular Cloning Expression and Characteristic of a Fifth Melanocortin Receptor," (unpublished). Of note was the absence of mMC5 receptor in brain tissue, a tissue known to express MC3 receptor and MC4 receptor, and placenta, a tissue which expresses MC3 receptor. Gantz, I. et al., *J. Biol. Chem.* 268:8246–8250 (1993) and Gantz, I. et al., *J. Biol. Chem.* 268:15174–15179 (1993). In addition, utilizing the same mMC5 receptor probe under conditions of reduced stringency to accommodate cross-species differences, no expression was observed in the human A375 melanoma cell line, which expresses MC1 receptor, or in either normal or malignant human adrenal cortical tissues, both of which express MC2 receptor. Gantz, I. et al., *J. Biol. Chem.* 268:8246–8250 (1993) and Gantz, I. et al., *J. Biol. Chem.* 268:15174–15179 (1993). It is notable, however, that experiments were unable to demonstrate mMC5 receptor expression in any human tissue, (human MTN blot or human MTN blot II, Clontech), including tissues shown to express this receptor in the mouse. Furthermore, so far isolation of an homologous human receptor has been unsuccessful despite three attempts at screening two different human genomic libraries and one human muscle cDNA library using a mMC5 receptor probe. While inconclusive, these data suggest the possibility that there is no counterpart to the mMC5 receptor in man.

SPECIFIC EXAMPLE 3

PHARMACOLOGICAL STUDIES

Materials and Methods

Peptide Synthesis. The following peptides were obtained from Peninsula Laboratories, Inc. (Belmont, Calif.): human and rat ACTH, ACTH(1-10), ACTH(4-10), ACTH (1-13), α-MSH, [Nle$^4$,D-Phe$^7$]α-MSH, β-MSH, γMSH, [des-acetyl] α-MSH, β-endorphin, porcine β-lipotropin, and [Met]enkephalin. Substituted melanocortin peptides (Pro$^{11}$γ-MSH, Phe$^1$γ-MSH, Thr$^1$γMSH, Thr$^1$, Pro$^{11}$γ-MSH) and ACTH (4-13) were synthesized by the University of Michigan Protein and Carbohydrate Structure Facility on an Applied Biosystems Model 431 peptide synthesizer using standard FMOC chemistry.

cAMP Assays. For these assays a cAMP assay kit (TRK 432, Amersham Corp.) was employed. Cells transfected with the receptors were grown to confluence in 12-well (2.4×1.7 cm) tissue culture plates. The cells were maintained in Dulbecco's modified Eagle's medium (GIBCO) containing 4.5 g/100 ml glucose, 10% fetal calf serum, 100 units/ml penicillin and streptomycin, 1 mM sodium pyruvate, and 1 mg/ml Geneticin. For assays, this medium was removed and cells were washed twice with Earle's balanced salt solution containing 10 mM Hepes (pH 7.4), 1 mM glutamine, 26.5 mM sodium bicarbonate, and 100 mg/ml bovine serum albumin. An aliquot (0.5 ml) of Earle's balanced salt solution was placed into each well along with 5 μl of 2×10$^{-2}$ M isobutylmethylxanthine. Varying concentrations of agonist were added, and the cells were incubated to 30 min at 37° C. Ice-cold 30% trichloracetic acid (500 μl/well) was added to stop the reaction and precipitate cellular protein. The cells were scraped and transferred to 16×150-mm glass tubes, then placed on ice for 30 min. The precipitate was then centrifuged for 10 min at 1,900×g, and the supernatant was ether extracted, lyophilized, and resuspended in 50 mM Tris, 2 mM EDTA (pH 7.5). cAMP content was then measured by a competitive binding assay according to the assay instructions. Percent change in intracellular cAMP was calculated using the response of 10$^{-6}$M αMSH as 100% response.

Binding Assays. Transfected cells were grown to confluence in 2.4×1.7 cm multiwell plates. After removal of media the cells were washed twice with Earle's balanced salt solution (EBSS, Gibco, Grand Island, N.Y.) and incubated for 1 h with 36nCi (1Ci=37GBq) of the $^{125}$I-labeled [Nle$^4$, D-Phe$^7$]α-MSH ([$^{125}$I]NDP-MSH) which was prepared according to the protocol of Tatro and Reichlin. Tatro, J. B. et al., *Endocrinology* 121:1900–1907 (1987). Binding reactions were terminated by removing the media and washing the cells twice with 0.2 M sodium phosphate/0.15 M NaCl (pH 7.4). The cells were lysed with 1% Triton X-100 and the radioactivity in the lysate was quantified in a liquid scintillation counter. Nonspecific binding was determined by measuring the amount of [$^{125}$I]NDP-MSH remaining bound in the presence of 10$^{-5}$M unlabeled NDP-MSH and specific binding was calculated by subtracting nonspecifically bound radioactivity from total bound radioactivity.

Results

Figure 2B:
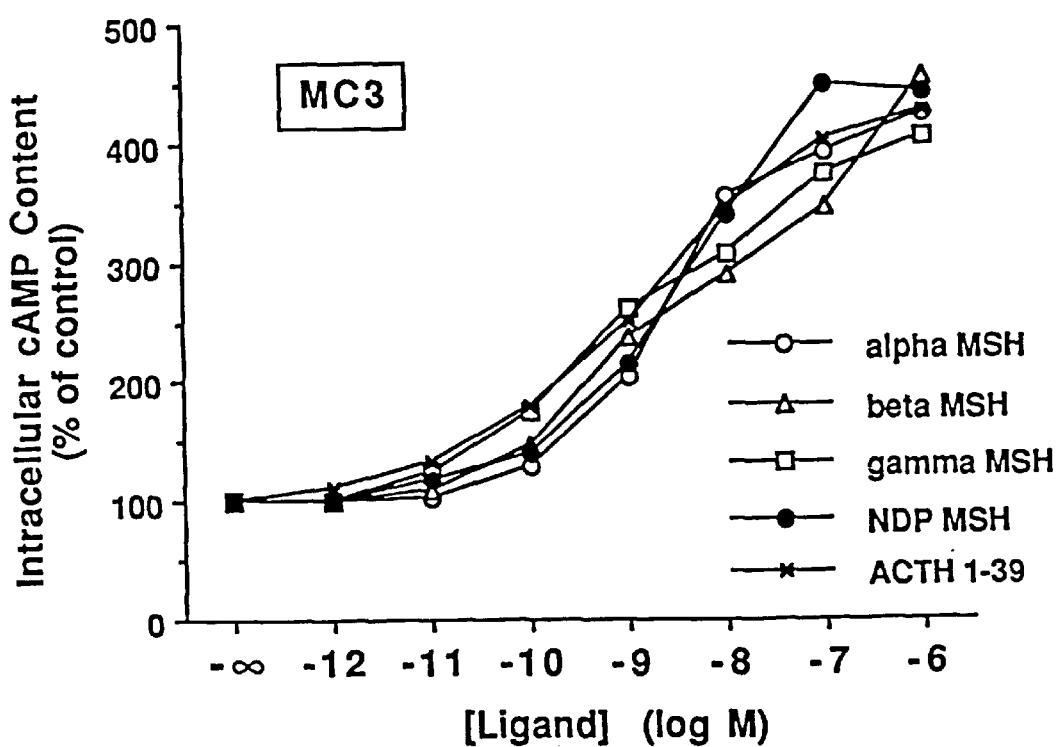

Melanocortin-3 Receptor. The pharmacological characteristics of the MC3 receptor demonstrated subtle but significant differences with those of the α-MSH (melanocortin-1) receptor. Both receptors responded to α-MSH and ACTH with equal potency and efficacy as depicted in FIGS. 2A and 2B. In this regard the present investigations are at variance with those of Mountjoy, K. G. et al., *Science* 257:1248–1251 (1992), who observed that ACTH was less potent and less efficacious than α-MSH in inducing cAMP production via the MC1 receptor. However, the present investigations are consistent with those of Chhajlani, V. et al., *FEBS Lett.* 309:417–420 (1992), who noted that ACTH and α-MSH had equal affinities in displacing $^{125}$I-labeled [Nle$^4$,D-Phe$^7$]α-MSH from the MC1 receptor. The results of the present studies are shown in FIGS. 2A and 2B. FIGS. 2A and 2B shows the generation of cAMP in L-cells transfected with the MC1 receptor (FIG. 2A) and the MC3 receptor (FIG. 2B) in response to α-MSH, β-MSH, γ-MSH, ACTH(1-39), and [Nle$^4$, D-Phe$^7$]α-MSH. Each point represents the average of duplicate samples from three different experiments. Standard errors were less than 10% for each point on this figure.

In view of previous structure-function studies indicating that the free NH$_2$-terminal serine in the ACTH molecule is an essential requirement for the hormone's full biological activity as described in Garren, L. D., *Vitam. Horm.* 26:119–141 (1968), the fact that α-MSH (which has an acetylated NH$_2$-terminal serine) is as potent and efficacious as ACTH in acting at both the MC1 and MC3 receptors clearly categorizes these two receptors as MSH receptors. The ED$_{50}$ of ACTH and α-MSH with both receptors, approximately 10$^{-9}$ M, is consistent with that observed for MSH receptors in previous pharmacological studies. Responses of the MC1 receptor and the MC3 receptor to [des-acetyl] α-MSH, which lacks the acetylated serine at the amino terminus of the peptide were identical to those observed for ACTH and α-MSH (data not shown). In addition, neither the MC1 receptor nor the MC3 receptor responded to the other POMC-derived peptides [Met] enkephalin or β-endorphin (data not shown).

Figure 3A:
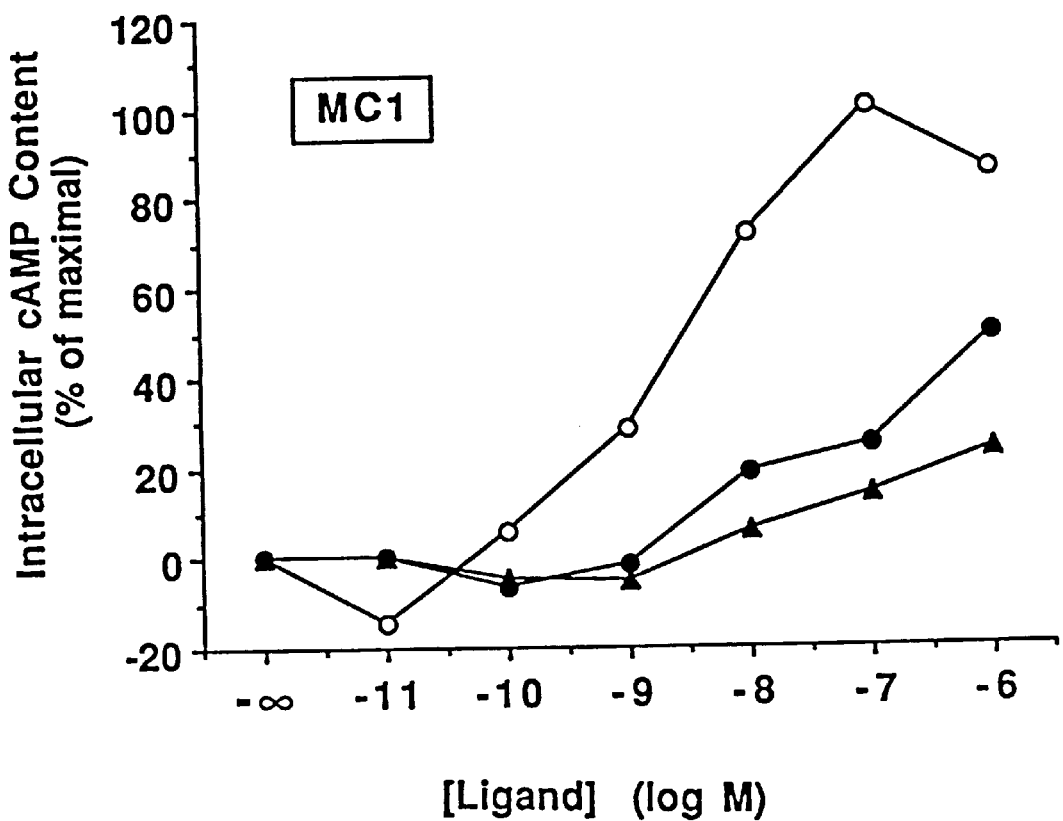
FIGS. 3A and 3B are graphs showing the generation of cAMP in L-cells transfected with the MC1 and MC3 receptor genes, respectively, in response to various truncated ACTH peptides.
Figure 3B:
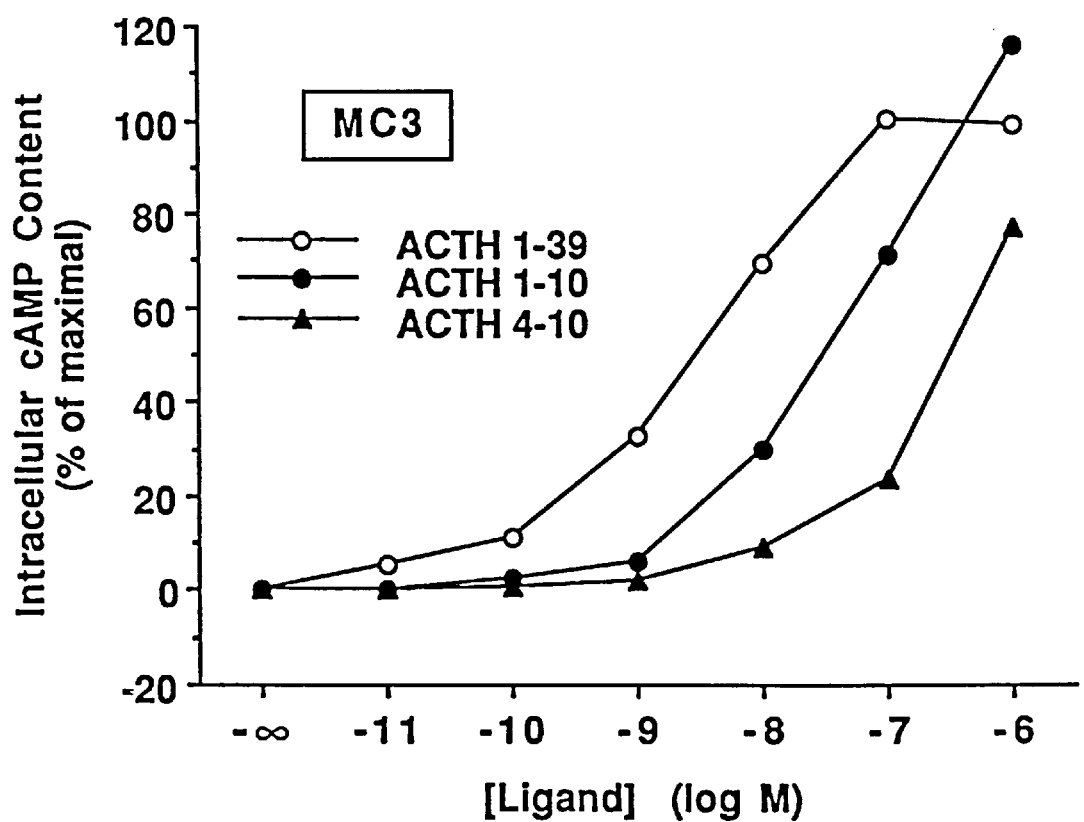

A major difference in the pharmacological characteristics of the MC1 and MC3 receptors is in their responses to β- and γ-MSH. Although the MC3 receptor responds to these two peptides as well as it does to ACTH and α-MSH, the MC1 receptor does not, as shown in FIGS. 2A and 2B. β-MSH is fully efficacious in stimulating cAMP production via the MC1 receptor, but its potency is 10-fold lower than that of ACTH and α-MSH. γ-MSH is unable to induce a full cAMP response through the MC1 receptor, even at maximal concentrations. The differences between the MC1 and MC3 receptors in ligand specificity are corroborated in studies with the truncated peptides ACTH(1-10) and ACTH(4-10) as shown in FIGS. 3A and 3B. FIGS. 3A and 3B shows the generation of cAMP in L-cells transfected with the α-MSH (MC1, FIG. 3A) and the novel melanocortin receptor MC3 (FIG. 3B) in response to ACTH(1-10) and ACTH(4-10). For ease of comparison, the data are presented as percentage of the maximal response to ACTH(1-39). Each point represents the average of duplicate samples from three different experiments. Standard errors were less than 10% for each point in this figure. Because these studies show MC3 receptor appears to recognize ACTH and α-, β-, and γ-MSH equally well, the core heptapeptide is the specific site of the melanocortins that is recognized by the receptor. The observation that ACTH(4-10) and ACTH(1-10) both demonstrated full efficacy in stimulating cAMP production via the MC3 receptor supports this assertion. The lower order potency noted with the truncated peptides reflects that their smaller size gives them somewhat lower affinity for the receptor. In contrast, neither ACTH(1-10) nor ACTH(4-10) were able to induce a full response with the MC1 receptor. Since α-MSH is equivalent to ACTH(1-13), the marked reduction in activity noted with ACTH(1-10) and ACTH(4-10) indicates that both the structures of the amino- and carboxyl-terminal ends of α-MSH are important for full biological activity of the MC1 receptor.

Figure 4:
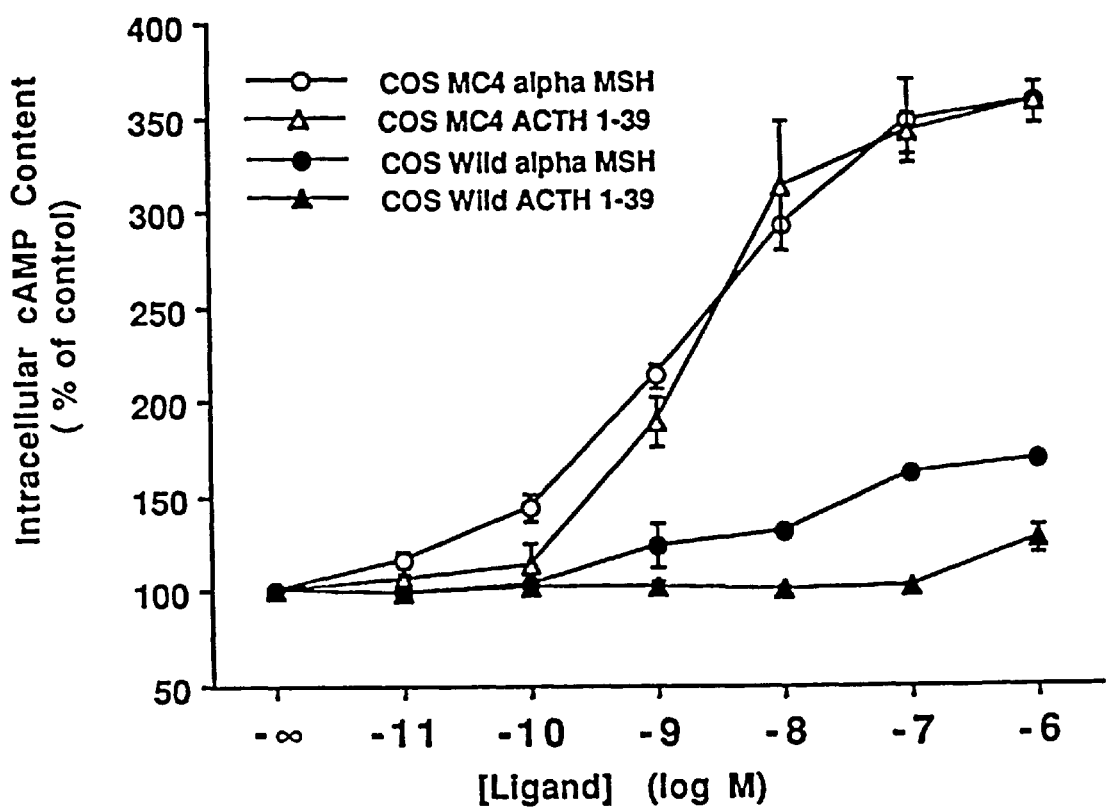
FIG. 4 is a graph showing the generation of cAMP in response to ACTH and α-MSH in wild type COS-1 cells and COS-1 cells transiently transfected with the MC4 receptor gene.

Melanocortin-4 Receptor. The pharmacological characteristics of this receptor confirm that it is a member of the melanocortin receptor family. As shown in FIG. 4, COS-1 cells transiently transfected with the MC4 receptor gene demonstrated a marked increase in intracellular cAMP content in response to stimulation with both α-MSH and ACTH.

It is of note, however, that wild-type COS-1 cells appear to have a small endogenous response to melanocortins. COS-1 cells transfected with the CMV vector containing no insert had a response indistinguishable from that obtained with the wild-type cells. The data in FIG. 4 represents an average of duplicate samples from two different experiments. FIG. 4 shows the generation of cAMP in response to ACTH and α-MSH in wild type COS-1 cells and COS-1 cells transiently transfected with the MC4 receptor gene. Wild type cells have a small endogenous response to the peptides. COS-1 cells transfected with the CMV vector without a receptor insert had a response comparable to the wild type cells. The data in FIG. 4 represents an average of duplicate samples from two different experiments.

Figure 5:
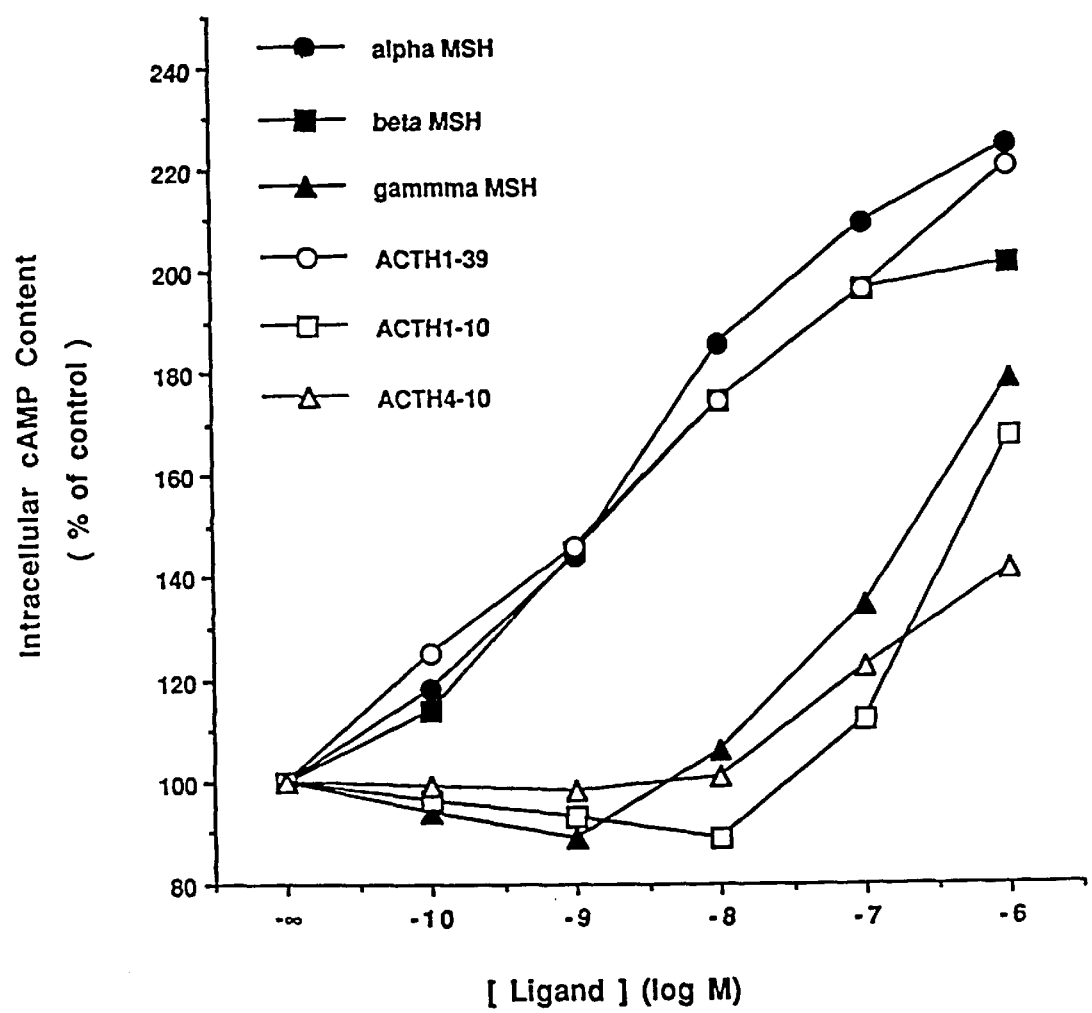
FIG. 5 is a graph showing the generation of cAMP in L-cells transfected with the MC4 receptor gene in response to various whole and truncated melanocortins.

For further examination of the pharmacological characteristics of the MC4 receptor, its gene was permanently transfected into L-cells, a murine fibroblast cell line, which demonstrate no endogenous response to melanocortins. FIG. 5 shows generation of cAMP in L-cells transfected with the MC4 receptor gene. Responses to α-, β-, and y-MSH, ACTH(1-10) and ACTH(4-10) (n=3 separate experiments) were measured. Each point represents the average of the total number of experiments obtained with each agonist. Standard errors were less than 12% for each point. As shown in FIG. 5, in the transfected cells, ACTH and α-MSH elicited a dose-dependent increase in intracellular cAMP content with equal potency and efficacy. The equipotence of α-MSH and ACTH in stimulating MC4 receptors is identical with the responses observed in L-cells transfected with the genes encoding the MC1 and MC3 receptors. The observed half-maximal effect of the two ligands ($EC_{50}=10^{-9}$ M) is consistent with previously published pharmacological studies of melanocortin receptors. Like the MC1 and MC3 receptors, the MC4 receptor did not respond to the other pro-opiomelanocortin-derived peptides Met-enkephalin or β-endorphin although a small increase in cAMP was observed after stimulation with β-lipotropic.

Despite these similarities, the MC4 receptor demonstrates subtle but important pharmacological differences from the other melanocortin receptors which could be elicited with the various ligands depicted in FIG. 6. In FIG. 6 the core heptapeptide amino acids are boxed. As discussed above, the MC3 receptor recognizes the ACTH(4-10) core of the melanocortins, thus it responds with equal potency and efficacy to α-, ,β-, and y-MSH and ACTH. In contrast, y-MSH is unable to stimulate a full cAMP response via the MC1 receptor, and the potency of β-MSH at this receptor is 10-fold lower than that for a α-MSH and ACTH. Accordingly, the specificity of the MC1 receptor appears to depend on amino acid residues that extend in the carboxyl- and amino-terminal directions from the ACTH(4-10) core. This conclusion was supported by the observation that the truncated peptides ACTH(1-10) and ACTH(4-10) were fully efficacious agonists on MC3 receptors but not on MC1 receptors. In this respect, the MC4 receptor more closely resembles the MC1 receptor as shown in FIG. 5. One key difference between MC4 and MC1 receptors, however, is that p-MSH is equipotent with ACTH and α-MSH in acting on the former but not the latter. This observation implies that a portion of the β-MSH molecule at the carboxy-terminal extension beyond the ACTH(4-10) core can determine the selectivity between MC1 and MC4 receptors. Structural analysis of FIG. 6 shows $Pro^{12}$ of ACTH, which is shared by α-MSH and ACTH but not by y-MSH, is critical for binding as a full agonist to the MC4 receptor. Because y-MSH has a Phe substitution in the position corresponding to $Pro^{12}$ of ACTH, it is a less potent agonist than ACTH or α-MSH. The tyrosine ($Tyr^2$) residue of ACTH is also important in defining activity at the MC4 receptor inasmuch as y-MSH and ACTH(1-10) appear to have slightly greater efficacy than ACTH(4-10) which is lacking this amino acid residue. These findings may have implication for the design of specific agonists or antagonists for the MC4 receptor.

Figure 7A:
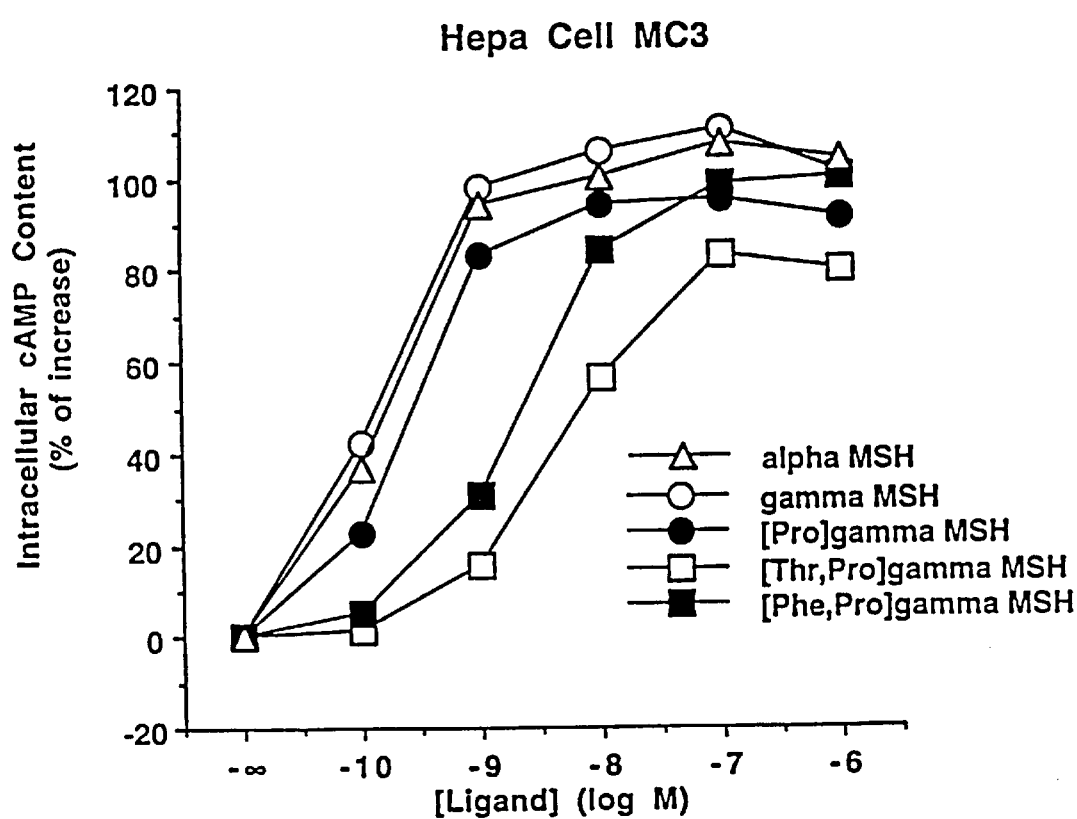
FIGS. 7A and 7B are graphs showing the measurement of intracellular cAMP content after stimulation of the MC3 receptor and the MC4 receptor, respectively, with natural melanocortins and synthetic peptides in Hepa cells.
Figure 7B:
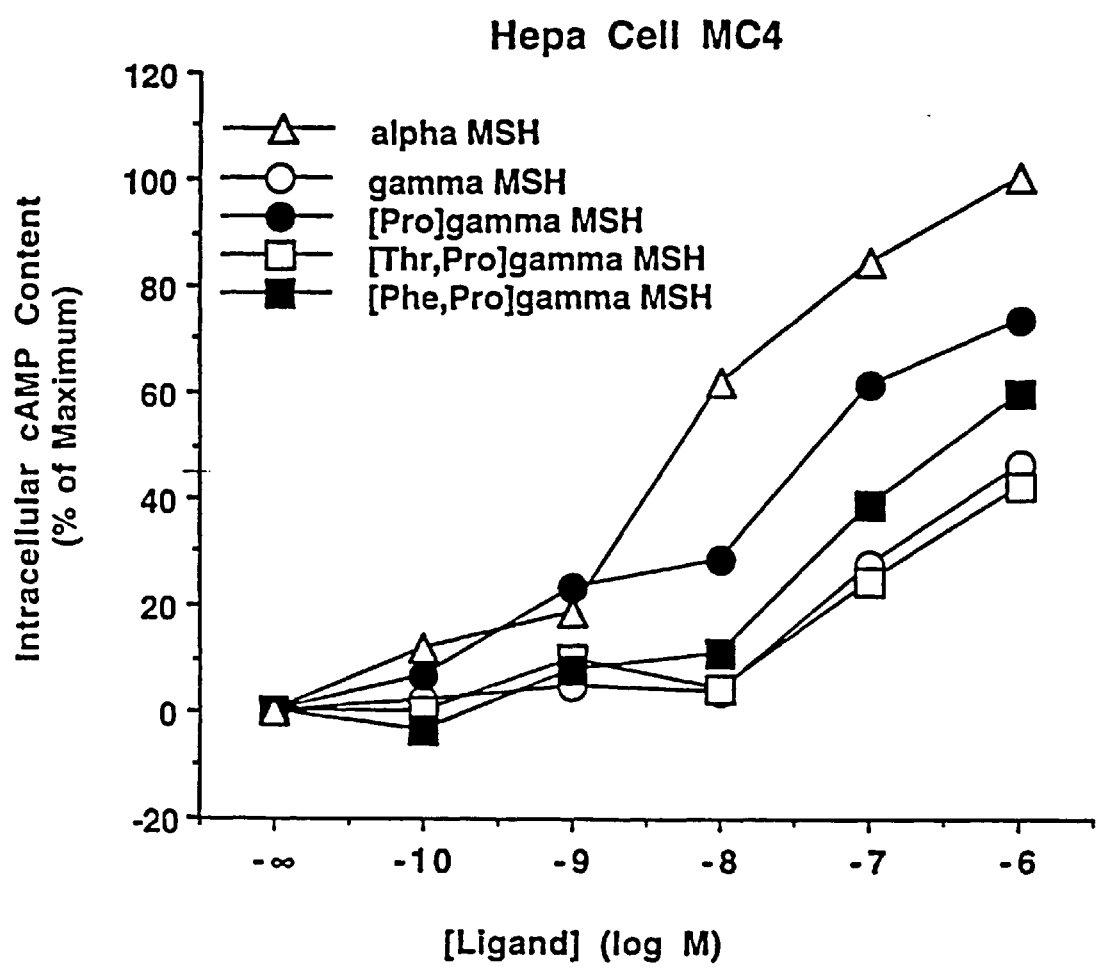

Further Studies on the Melanocortin-3 and Melanocortin-4 Receptors. To test the hypothesis that the proline ($Pro^{12}$) in the C-terminal portion of ACTH/α-MSH was a key determinant of melanocortin activation of the MC4 receptor, a y-MSH-like peptide was synthesized that substituted the phenylalanine ($Phe^{11}$) present in the C-terminal portion of y-MSH with a proline ($Pro^{11}$). As represented in FIG. 6 (see also Sequence Listing ID Nos. 13–23), $Pro^{11}$ of y-MSH is equivalent to the $Pro^{12}$ of ACTH/α-MSH. If the $Pro^{12}$ of ACTH/α-MSH was of key importance for the activation of the MC4 receptor by substituting the $Phe^{11}$ of that molecule with proline should increase the activity of y-MSH at this receptor. y-MSH was chosen as the melanocortin to be altered because it has full agonist activity at the MC3 receptor, but is only a weak agonist at the MC4 receptor. In addition, as already noted, y-MSH contains two substitutions of the common melanocortin heptapeptide sequence which may render it more informative for investigating the hypothesis that the core sequence is of lesser importance to the activation of the MC4 receptor. Conversely, if the MC3 receptor is activated predominantly by amino acids present in the melanocortin core heptapeptide sequence, then the substitution of this $Phe^{11}$ (which is outside the core heptapeptide sequence) with $Pro^{11}$ should not result in any significant diminution of the activity of the substituted $Pro^{11}$ y-MSH when compared to y-MSH at that receptor. Consistent with this reasoning, as shown in FIG. 7A, wherein each point represents the average of 3–6 separate experiments, substitution of $Phe^{11}$ of y-MSH with proline had no significant effect on the activation of MC3 receptor. As shown in FIG. 7B, substitution of $Phe^{11}$ of y-MSH with proline profoundly increased the activity of y-MSH at the MC4 receptor. Using the dose response curve of α-MSH as a reference for maximum response, the potency of the $Pro^{11}$ y-MSH in comparison to y-MSH was increased nearly a log (from an $EC_{50}$ of $2 \times 10^{-8}$ M to $1 \times 10^{-7}$ M) and the efficacy of $Pro^{11}$ y-MSH in comparison to y-MSH was increased from 45% (y-MSH) to 75% ($Pro^{11}$ y-MSH-like peptide). This was consistent with the hypothesis that the proline moiety present in the carboxyl terminal portion of melanocortins is a structural component specifically important to the activation of the MC4 receptor as opposed to the MC3R.

To investigate the contribution of amino acids in the N-terminal portion of the melanocortin peptides to the activation of the MC3 and MC4 receptors, a tyrosine residue ($Tyr^2$) in the N-terminal portion of ACTH/α-MSH was focused on. As already stated, the greater activity of ACTH (1-10) than ACTH (4-10) at the MC4 receptor suggested a contribution of this amino acid, which is conserved in all the melanocortins, to the activation of this receptor. If the hypothesis regarding the contribution of this tyrosine to the activation of the MC4 receptor was correct, then any alteration of this amino acid should diminish the activity of a peptide containing a tyrosine substitution at this receptor. Since it was already demonstrated that the $Pro^{11}$ y-MSH compound had increased activity as compared to y-MSH at the MC4 receptor (but not the MC3 receptor) two tyrosine substitutions in the $Pro^{11}$ y-MSH peptide were designed. These two substitutions consisted of an exchange of the $Tyr^1$ of $Pro^{11}$ y-MSH (which is analogous to the $Try^2$ of ACTH/

α-MSH, see FIG. 6) with a phenylalanine (Phe$^1$) or a threonine (Thr$^1$). These substitutions were an attempt to examine the major component groups of the amino acid tyrosine, a phenol ring and an hydroxyl group. As shown in FIG. 7B, substitution of Tyr$^2$ by either phenylalanine or threonine diminished both the potency and efficacy of these substituted compounds at the MC4 receptor as compared to the Pro$^{11}$ y-MSH. This was consistent with the hypothesis that Try$^2$ of ACTH/α-MSH is important for the activation of the MC4 receptor. However, since the Phe$^1$, Pro$^{11}$ y-MSH had greater activity than y-MSH or Thr$^1$, Pro$^{11}$ y-MSH, even though its activity was only intermediate between these compounds, it was concluded that the phenylalanine ring of the tyrosine residue has a more significant role than the hydroxyl group. Conceivably, the activity of the phenylalanine moiety could be attributed to its bulky and/or hydrophobic properties.

As shown in FIG. 7A, the diminished activity of the tyrosine substituted Pro$^{11}$ y-MSH peptides at the MC3 receptor suggests that this tyrosine moiety is also important to the activation of the MC3 receptor. Therefore, the equipotence of the various melanocortin peptides at the MC3 receptor is due to this conserved tyrosine residue in addition to the amino acids of the shared heptapeptide core as was originally hypothesized.

Figure 8A:
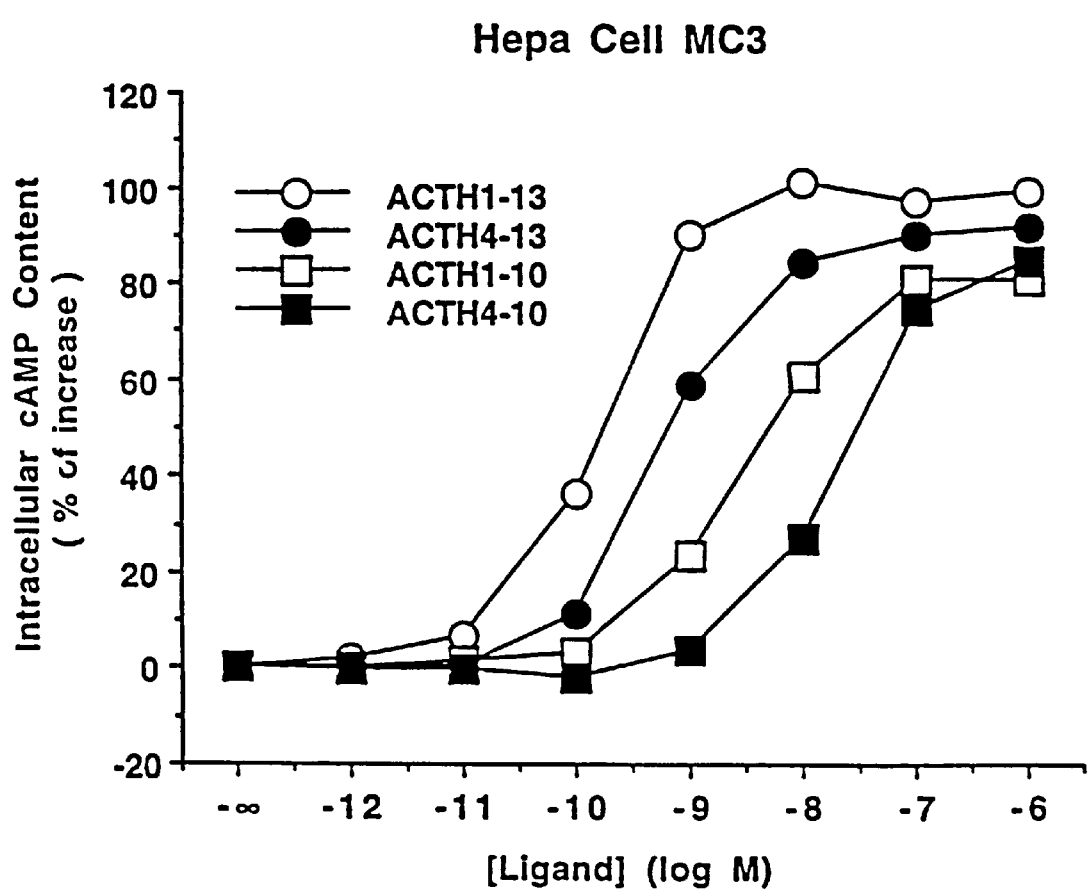
FIGS. 8A and 8B are graphs showing the measurement of intracellular cAMP content after stimulation of the MC3 receptor and the MC4 receptor, respectively, with truncated melanocortin peptides in Hepa cells.
Figure 8B:
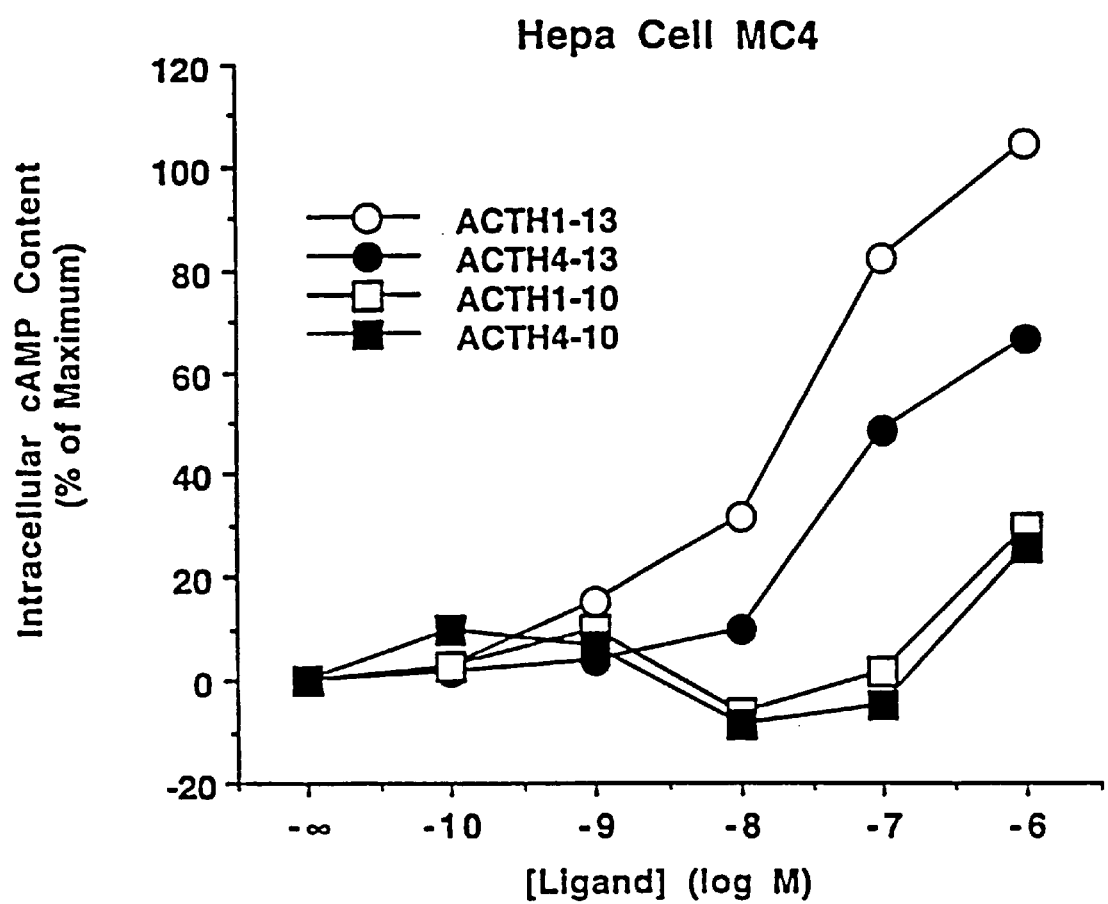

The contribution of both the proline in the C-terminal and the tyrosine in the N-terminal portions of the melanocortins to the activation of the MC3 and MC4 receptors using several truncated peptides was further examined. The truncated peptide ACTH (4-13) which contains the C-terminal proline shown to be important for the activation of the MC4 receptor but which lacks the biologically active N-terminal tyrosine necessary for the full activation of both receptors was synthesized and the activity of this synthetic peptide with ACTH (1-10), ACTH (4-10), and ACTH (1-13) was compared. As expected, ACTH (1-13) had maximal efficacy at both the MC3 and MC4 receptors. These results are depicted in FIGS. 8A and 8B wherein each point represents the average of 3–6 experiments. However, as shown in FIG. 8B, the efficacy of ACTH (1-10) or ACTH (4-10) which lack the C-terminal proline was only 30% of that of ACTH (1-12) at the MC4 receptor. In contrast, the efficacy of ACTH (4-13) which contains the critical proline moiety was increased to 60% of the maximal response of ACTH (1-13). Thus, ACTH (4-13) is twice as efficacious as of either ACTH (1-10) or ACTH (4-10) at the MC4 receptor. At the same time, the efficacy of ACTH (1-13), ACTH (1-10), ACTH (4-10), and ACTH (4-13) are nearly the same at the MC3 receptor as shown in FIG. 8A. These data support the contention that the melanocortin core heptapeptide sequence is a key element responsible for conferring full efficacy to these peptides at the MC3 receptor. Since, as shown in FIG. 7A, α-MSH, y-MSH (which lacks a C-terminal Pro), and Pro$^{11}$ y-MSH are equipotent at the MC3 receptor, the increased order of potency of the truncated peptides (ACTH (1-13)>>ACTH (1-10) which is roughly equivalent to ACTH (4-13)>ACTH (4-10)) is interpreted to be due to the increasing size (in terms 15 of increasing length) of these truncated peptides rather than to the presence or absence of the C-terminal proline or N-terminal tyrosine. This increase in length may confer greater affinity for the peptides at the MC3 receptor. In contrast, the equal and lesser potency of both ACTH (1-10) and the smaller peptide ACTH (4-10) when compared to the greater potency of ACTH (4-13) (which is the same number of amino acids as ACTH (1-10)) suggests that it is the C-terminal proline of ACTH/αMSH rather than peptide size alone that is the dominant factor in determining the activity of the truncated peptides at the MC4 receptor.

Figure 9A:
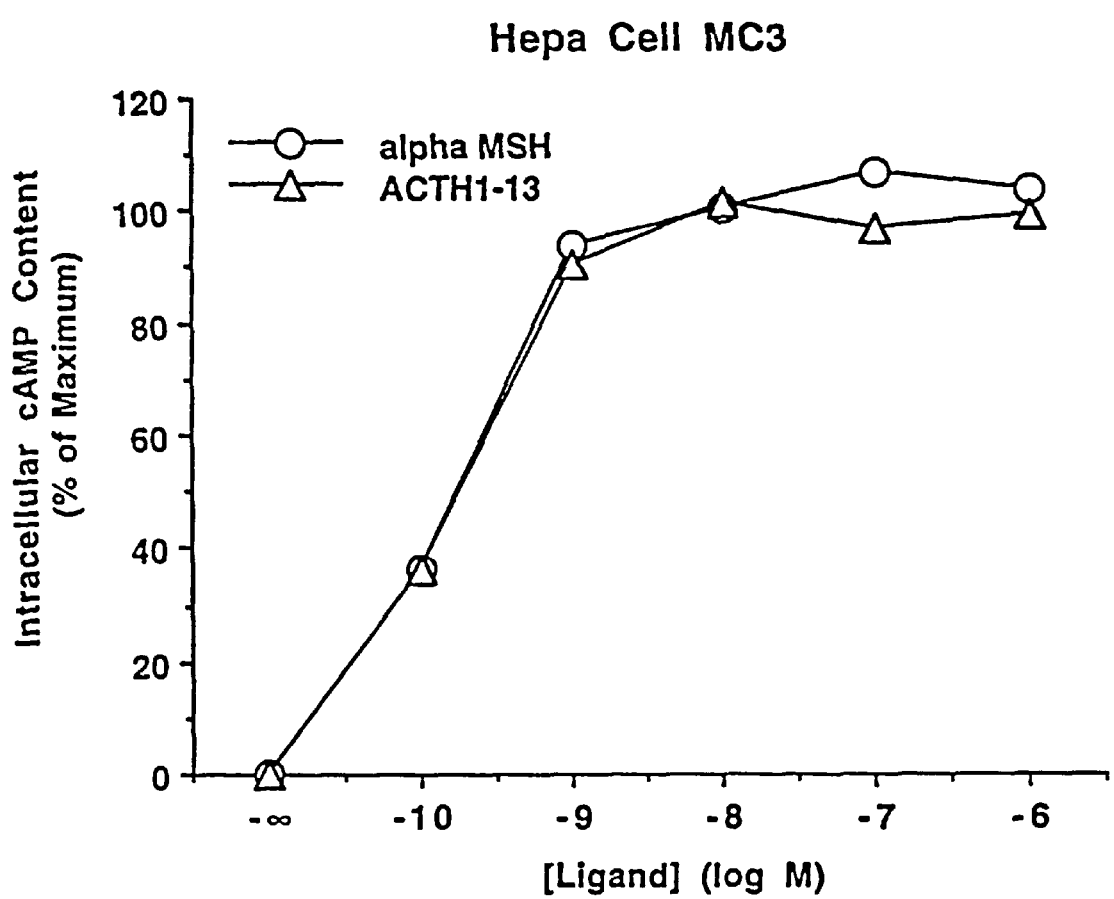
FIGS. 9A and 9B are graphs showing a comparison of the contribution of an acetylated N-terminal serine on the generation of intracellular cAMP at the MC3 receptor and MC4 receptor, respectively.
Figure 9B:
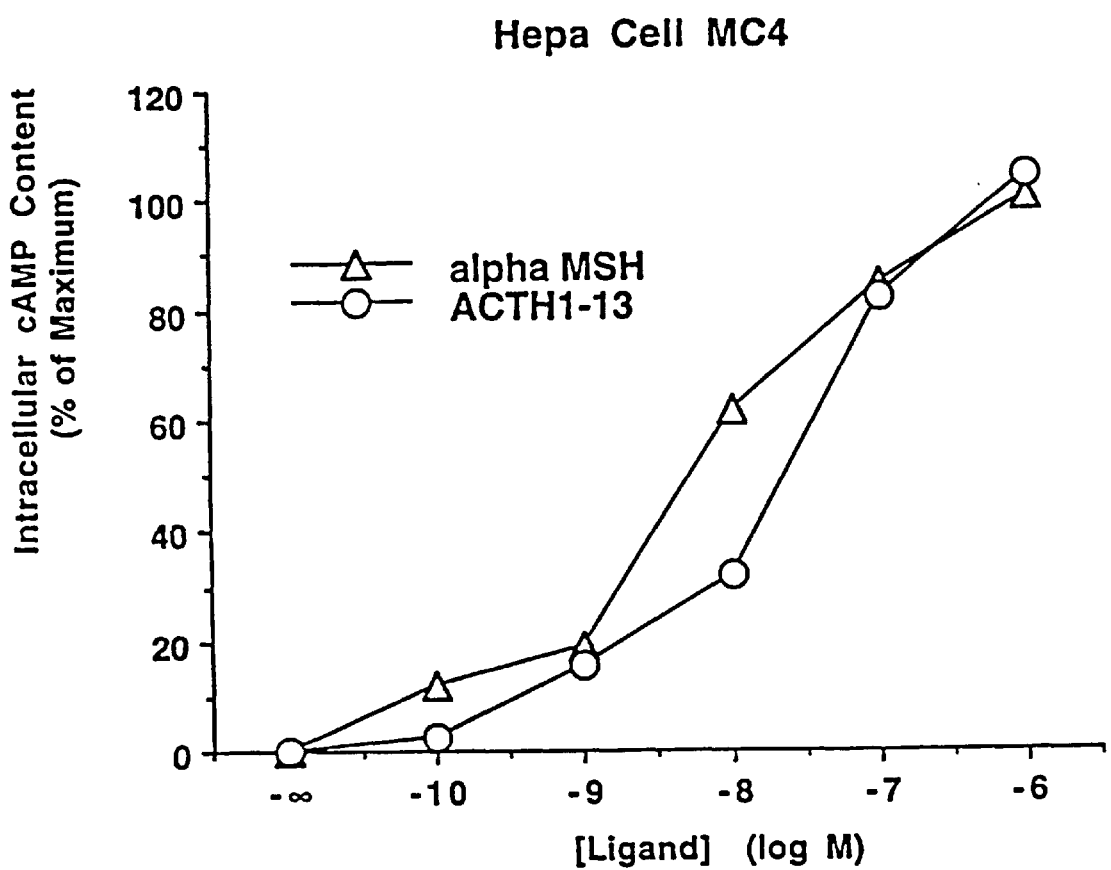

Finally, whether the presence of an acetylated N-terminal serine affects the activity of the melanocortins at either the MC3 or MC4 receptor was examined. Previous literature has suggested an acetylated serine is critical for the activity of ACTH at the MC2 receptor (adrenal ACTH receptor). Garren, L. D., *Vitam. Horm.* 26:119–141 (1968). As shown in FIGS. 9A and 9B, wherein each point represents the average of 3–6 experiments, no difference was observed between the activity of α-MSH which has an acetylated amino terminal serine and des-acetyl α-MSH (ACTH (1-10)) which lacks this acetyl group at both the MC3 and MC4 receptors.

In summary, the studies indicate that the proline residue present in the C-terminal portion of the melanocortin peptide sequence constitutes a crucial element underlying the selective pattern of response of the MC3 and MC4 receptors for the melanocortins. A tyrosine present in the N-terminal portion of the melanocortin peptides is necessary for the full activation of both the MC3 and MC4 receptors. Finally, the core heptapeptide sequence is essential to the activation of the MC3 receptor but is of lesser importance to the activation of the MC4 receptor. These results indicate a model of activation of the MC3 and the MC4 receptors by the melanocortins which could metaphorically liken these peptides to a "donut and its hole." The "donut" portion of melanocortins containing the N-terminal tyrosine and C-terminal proline residues is required for activation of the MC4 receptor whereas the "hole" the amino acids present in the core heptapeptide sequence of the melanocortins, is of much greater importance in the activation of the MC3 receptor. Information derived from these studies using substituted peptides provides a basis for the development of subtype specific melanocortin agonists and antagonists.

Figure 10:
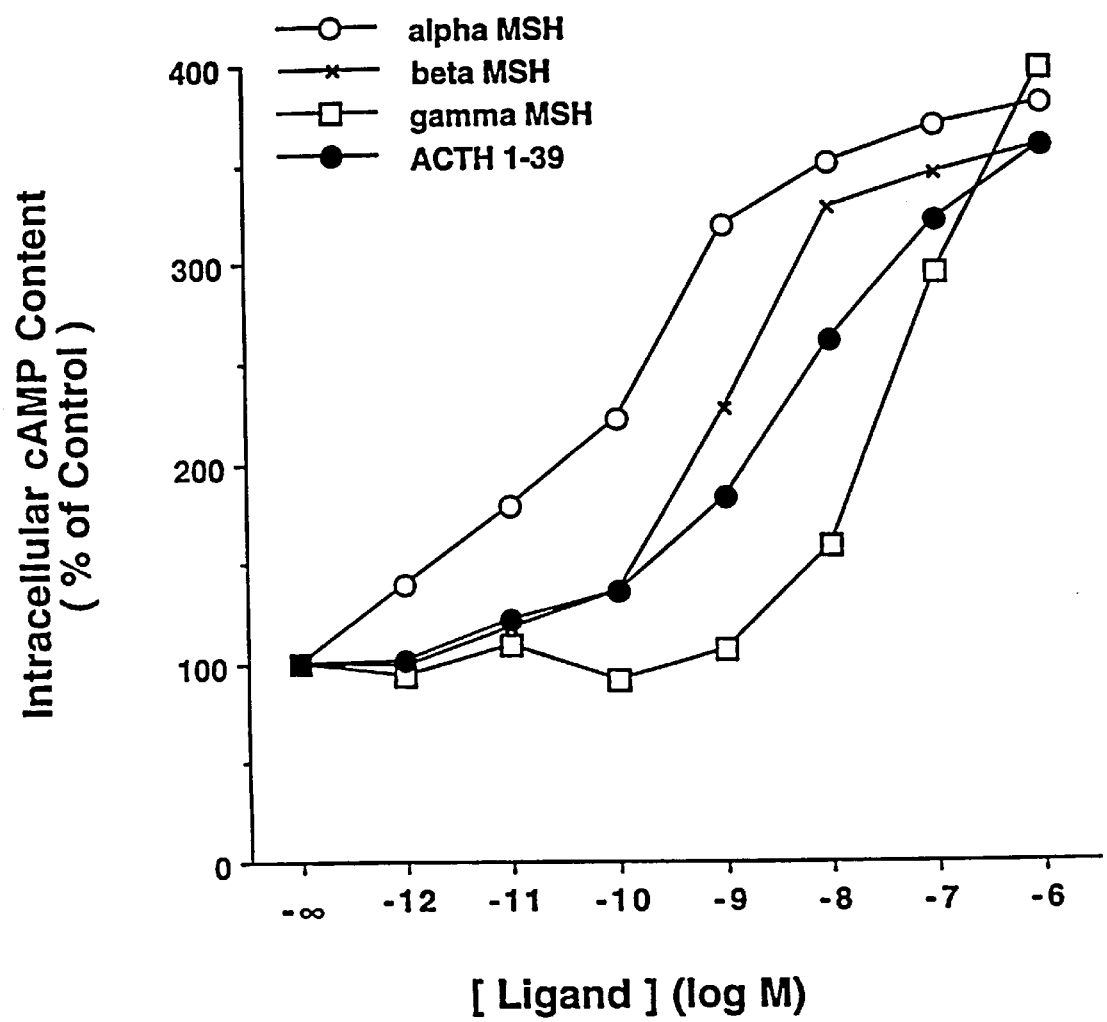
FIG. 10 is a graph showing the generation of cAMP in L-cells transfected with the mMC5 receptor in response to various melanocortins.
Figure 11:
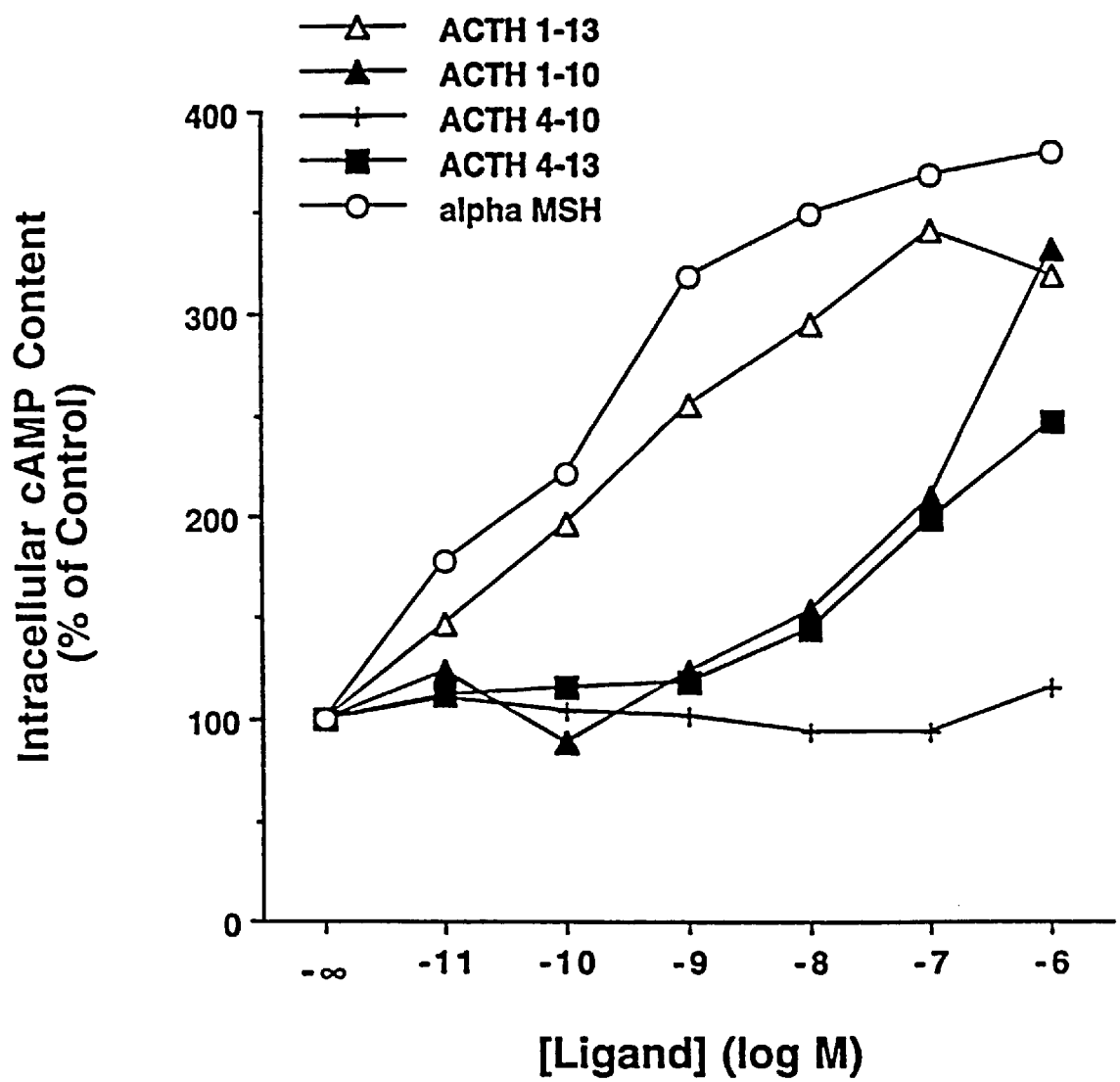
FIG. 11 is a graph showing the generation of cAMP in L-cells transfected with the mMC5 receptor in response to various truncated peptides.

Melanocortin-5 Receptor. The pharmacological profile of the mMC5 receptor is unique in that α-MSH is clearly more potent than ACTH in stimulating the production of intracellular cAMP in L-cells expressing the receptor. These results are represented in FIG. 10 where each point represents the average of 3 separate experiments and standard errors were less than 10% for each point. Rat ACTH, which differs from human ACTH in two amino acids produced the same results. Those data contrast with previous studies demonstrating that α-MSH and ACTH are equipotent in stimulating cAMP production by other human melanocortin receptors (MC1, MC3, and MC4 receptors) expressed in the same cell line. Gantz, I. et al., *J. Biol. Chem.* 268:8246–8250 (1993) and Gantz, I. et al., *J. Biol. Chem.* 268:15174–15179 (1993). Mountjoy, et al. have reported, however, that α-MSH is more potent than ACTH in stimulating cAMP production via the mMC1 receptor. Mountjoy, K. G. et al., *Science* 257:1248–1251 (1992). It is possible that the ability to differentiate between α-MSH and ACTH is a property unique to murine melanocortin receptors. In this regard, it is important to note the structural differences between α-MSH and ACTH (1-39). Although the amino acid sequence for the first 13 amino acids of ACTH is identical to that of α-MSH, ACTH (1-39) is not acetylated at its amino terminal end in the manner of α-MSH. Thus, the possibility that the ability of mMC5 receptor to distinguish between α-MSH and ACTH (1-39) might be dependent on the presence or absence of the amino terminal acetyl moiety, was examined. However, no difference between non-acetylated α-MSH ((ACTH (1-13)) and α-MSH in stimulating cAMP production in transfected cells was observed. Other studies examined whether the ability of the mMC5 receptor to distinguish between α-MSH and ACTH (1-13) on the one hand and ACTH (1-39) on the other occurs at the level of the receptor or reflects a post-receptor signaling phenomenon. These results are depicted in FIG. 11 wherein each point represents the average of 3 experiments and standard errors were less than 10% for each point. The former mechanism is supported by the results which indicated that the binding affinity of the mMC5 receptor for α-MSH and ACTH (1-13) appeared to be ten-fold greater than that for ACTH (1-39). These data imply that the mMC5 receptor does not distinguish between amino terminally acetylated or non-acetylated ACTH/α-MSH compounds and, thus, that the carboxyl terminal extension of ACTH (1-39) (ACTH (14-39)) must be the determinant of its diminished potency relative to α-MSH or ACTH (1-13). In addition, since a free non-acetylated amino terminus is an essential requirement for the ability of ACTH to induce steroidogenesis in the adrenal cortex (Garren, L. D., Vitam. Horm. 26:119–141 (1968)), the mMC5 receptor appears primarily not to be an ACTH receptor.

Figure 12:
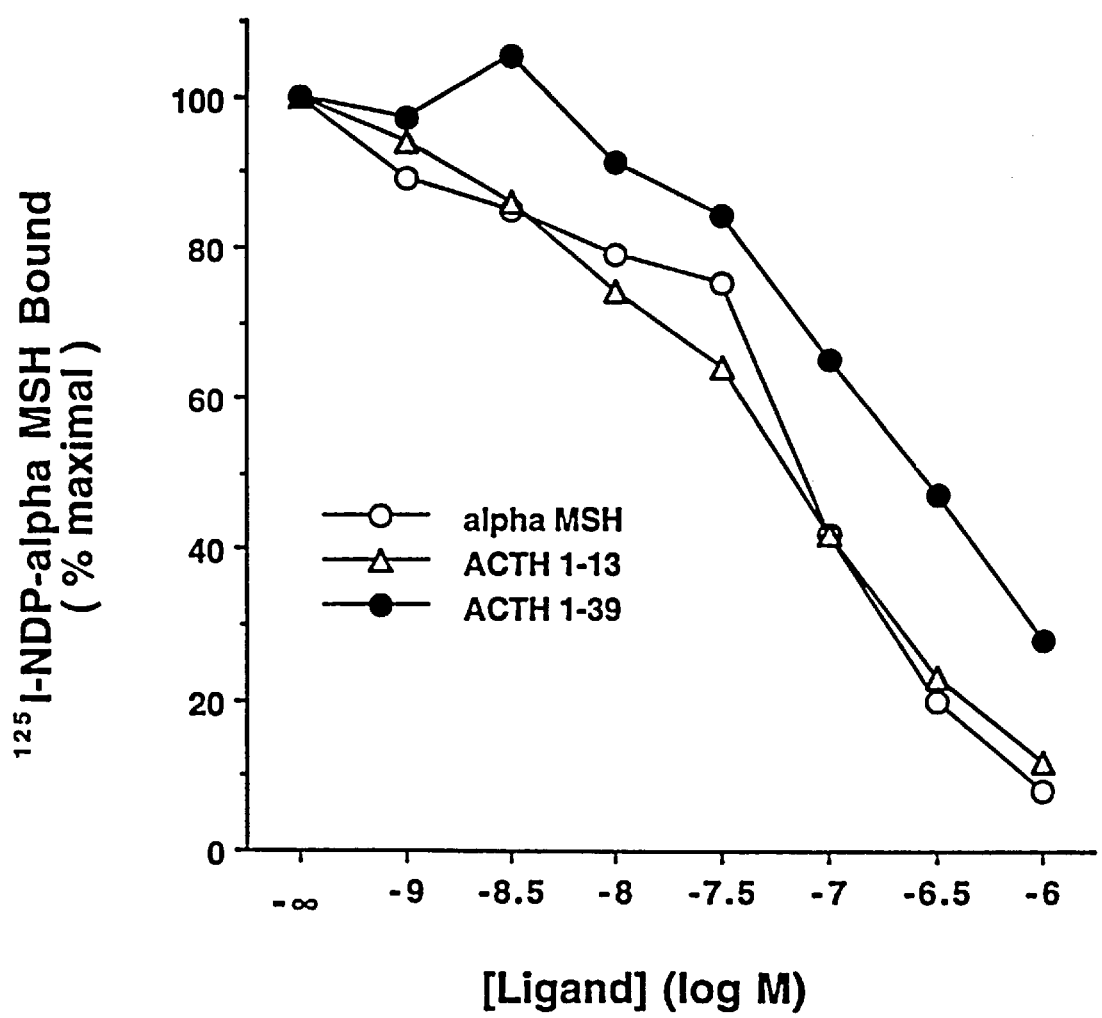
FIG. 12 is a graph showing the inhibition by α-MSH, ACTH (1-13) and ACTH (1-39) of [$^{125}$I] NDP-MSH binding to L-cells transfected with the mMC5 receptor.

Further studies were performed to characterize the ligand specificity of the mMC5 receptor. As shown in FIG. 10, both β- and α-MSH were full agonists, but were one and three orders of magnitude lower in potency, respectively, than α-MSH. The central core heptapeptide ((ACTH (4-10)) common to all melanocortins had essentially no biological activity as shown in FIG. 11. Neither were the other products of pro-opiomelanocortin processing, β-endorphin, met-enkephlin, or porcine β-lipotropin active on the mMC5 receptor (data not shown). However, α-MSH peptides which contain an amino (ACTH (1-10)) or carboxyl (ACTH (4-13)) terminal extension had full efficacy albeit with greatly diminished potency relative to α-MSH in inducing cAMP production in L-cells transfected with the mMC5 receptor, as shown in FIG. 12. The structure-function studies indicate that amino acids in both the carboxyl and amino terminal extension regions (relative to the heptapeptide core) of α-MSH are critical determinants of agonist activity at the mMC5 receptor. A comparison of the various ligands tested, the non-substituted peptides shown in FIG. 6 and ACTH (1-39), in conjunction with data herein suggests the possibility that $Tyr^2$ and $Pro^{12}$ of α-MSH are particularly important in this regard. The lack of activity of ACTH (4-10) and the full efficacy of α-MSH imply that the core heptapeptide may be important as a spacer between amino and carboxyl terminal extensions, but the specific sequences may be a less important factor in the binding of melanocortins to the mMC5 receptor. In this regard the mMC5 receptor resembles the MC4 receptor more closely than the other members of the melanocortin receptor family. Gantz, I. et al., *J. Biol. Chem.* 268:15174–15179 (1993).

SPECIFIC EXAMPLE 4

INTRACELLULAR SIGNALING PATHWAYS

Materials and Methods

Receptor Gene Expression. The coding region of the MC3 receptor gene was subcloned into the eukaryotic expression vector CMVneo using a polymerase chain reaction (PCR) strategy as previously described. Brown, N. A. et al., et al., *J. Biol. Chem.* 265:13181–13189 (1990) and Gantz, I. et al., *PNAS (USA)* 88:429–433 (1991). The insert was subsequently checked by dideoxynucleotide sequencing to insure that no errors were induced by the PCR. A rat hepatoma cell line (Hepa) which lacks endogenous melanocortin receptors was transfected with the CMVneo/MC3 receptor construct using the calcium phosphate co-precipitation method. Chen, C. A. et al., *Biotechniques* 6:632–638 (1988). Cells were selected for resistance to the neomycin analogue Geneticin (Life Sciences) and clones were subsequently chosen for high levels of receptor mRNA expression by Northern blot analysis.

Chimeric Receptor. For these studies a chimeric canine H2-histamine receptor (cH2R) in which the third intracytoplasmic loop (3i) of the MC3 receptor was substituted for the comparable segment of cH2R was expressed. The chimeric receptor (cH2R/MC3R-3i) was constructed by cassette mutation at the junction of the fifth and sixth transmembrane domains of cH2R. Six PCR primers were used to generate three DNA fragments which were subsequently ligated together. The three PCR-generated fragments consisted of 1) the 5' coding region of the cH2R receptor beginning just prior to the ATG codon and ending with the 3' end of the fifth transmembrane domain; 2) the portion of the MC3 receptor gene encoding its third intracytoplasmic loop; and 3) the 3' coding region of the cH2R beginning with that segment encoding the 5' end of the sixth transmembrane domain and ending slightly past the termination codon. The DNA fragments were cut with appropriate restriction enzymes at pre-engineered restriction sites designed so that the three fragments could be assembled together in only the correct alignment. Restriction sites were also designed to facilitate subcloning the chimeric receptor DNA into CMVneo and the sequencing vector M13. The nucleotide sequence of the CMVneo cH2R/MC3R-3i construct was confirmed prior to expression in Hepa cells.

cAMP Assays. A cAMP assay kit purchased from Amersham (TRK 432, Arlington Heights, Ill.) was employed. Transfected cells were grown to confluence in 12-well (2.4×1.7 cm) tissue culture plates. The cells were maintained in Dulbecco's modified Eagle's medium (DMEM, Gibco) containing 4.5 g/100 ml glucose, 10% fetal calf serum, 100 units/ml penicillin and streptomycin, 1 mM sodium pyruvate and 1 mg/ml of Geneticin. For assays, the media was removed and cells were washed twice with Earle's balanced salt solution (EBSS) containing 10 mM Hepes (pH 7.4), 1 mM glutamine, 26.5 mM sodium bicarbonate, and 100 mg/ml bovine serum albumin. An aliquot (0.5 ml) of EBSS was placed into each well along with 5 µl of $1 \times 10^{-2}$ M isobutylmethylxanthine. Varying concentrations of agonists (human ACTH (1-39) and α-MSH, Peninsula Laboratories, Belmont, Calif.) were added and the cells were incubated for 30 min at 37° C. Ice cold 100% ethanol (1 ml/well) was added to stop the incubation and the mixture including scraped cells was transferred to 16×150 mm glass tubes, placed on ice for 30 min, then centrifuged for 10 min at 1,900 X g. The supernatant was dried under a nitrogen stream, and resuspended in 50 mM Tris, 2.0 mM EDTA (pH 7.5). cAMP content was then measured by competitive binding assay according to the assay instructions. In some experiments cells were pre-treated for 30 min prior to agonist stimulation with the cAMP-dependent protein kinase (protein kinase A) inhibitor N-[2-(p-bromocinnamylamino) ethyl]-5-isoquinolinesulfonamide (H-89, Calbiochem, La Jolla, Calif.) or with H-85 (Seikagaku America, Rockville, Md.), an isoquinolone derivative with no inhibitory activity on protein kinase A. Forskolin and dibutryl cAMP were added simultaneously with the agonists in these experiments.

Inositol Phosphate (IP) Assays. Measurement of inositol phospholipid turnover in Hepa cells was performed according to a modification of previously published methods as follows. Berridge, M. J. et al., *Biochem J.* 212:473–482 (1983) and Wreggett, K. A. et al., *Biochem. J.* 245:655–660 (1987). Cells grown to semi-confluence in multiwell plates were prelabeled with [2-$^3$H] myo-inositol in DMEM for 24 hr, incubated in EBSS for 30 min, then incubated for another 15 min in EBSS with 10 mM LiCl. The final incubation was in media with experimental ligand added for up to three min after which ice cold 100% methanol was added and the cells were scraped and extracted with 2 ml chloroform, 10 μl HCl (13 N), and 200 μl of 100 mM EDTA in a 50 ml polypropylene tube. The mixture was then vortexed and centrifuged at 1,900 X g. The supernatant was removed and its pH was adjusted to 7.0 by adding 1 N NaOH. Waters Accel plus QMA SEP-PAK anion exchange cartridges (Waters Chromatography, Millipore Corporation, Milford, Mass.) were used to separate inositol phosphates under differing concentrations of formate\formic acid. The cartridges were pretreated by washing with 10 ml of a solution of 1 M ammonium formate in 0.1 M formic acid followed by 20 ml of distilled water. The samples were applied with a flow rate of approximately 10 ml/min using a 10 ml syringe. IPs were then eluted using 10 mM increments of ammonium formate in a stepwise fashion. Inositol monophosphate was eluted with 10 mM formic acid/100 mM ammonium formate/5 mM disodium tetraborate, inositol bisphosphate was eluted with 20 mM formic acid/200 mM ammonium formate/5 mM disodium tetraborate, and IP3 was eluted with 30 mM formic acid/300 mM ammonium formate/5 mM disodium tetraborate. This assay does not distinguish between 1,3,4 and 1,4,5 isomers of IP3. Eluted radioactivity from the pooled fractions (total inositol phosphates) were measured by liquid-scintillation spectrometry (Beckman model LS7800 instrument).

Measurement of Intracellular Ca++ Concentration ([Ca++]i). For these experiments, Hepa cells were detached by incubation in $Ca^{++}$-free EBSS with 2.0 mM EDTA, loaded with 1 μM fura-2/AM (Molecular Probes, Eugene, Oreg.) for 20 min at 37° C. in EBSS containing 0.1% BSA and 25 mM HEPES, washed by centrifugation at 50 X g, and resuspended and maintained in EBSS buffer at room temperature until the time of experimentation. [$Ca^{++}$]i measurements of cells suspended in a quartz cuvette were obtained using a dual-wavelength modular fluorometer (Spex-Fluorolog 2, Spex Industries, Edison, N.J.) according to previously described methods. DelValle, J. et al., *Am. J. Physiol.* 262:G420–426 (1992).

Results

Figure 13A:
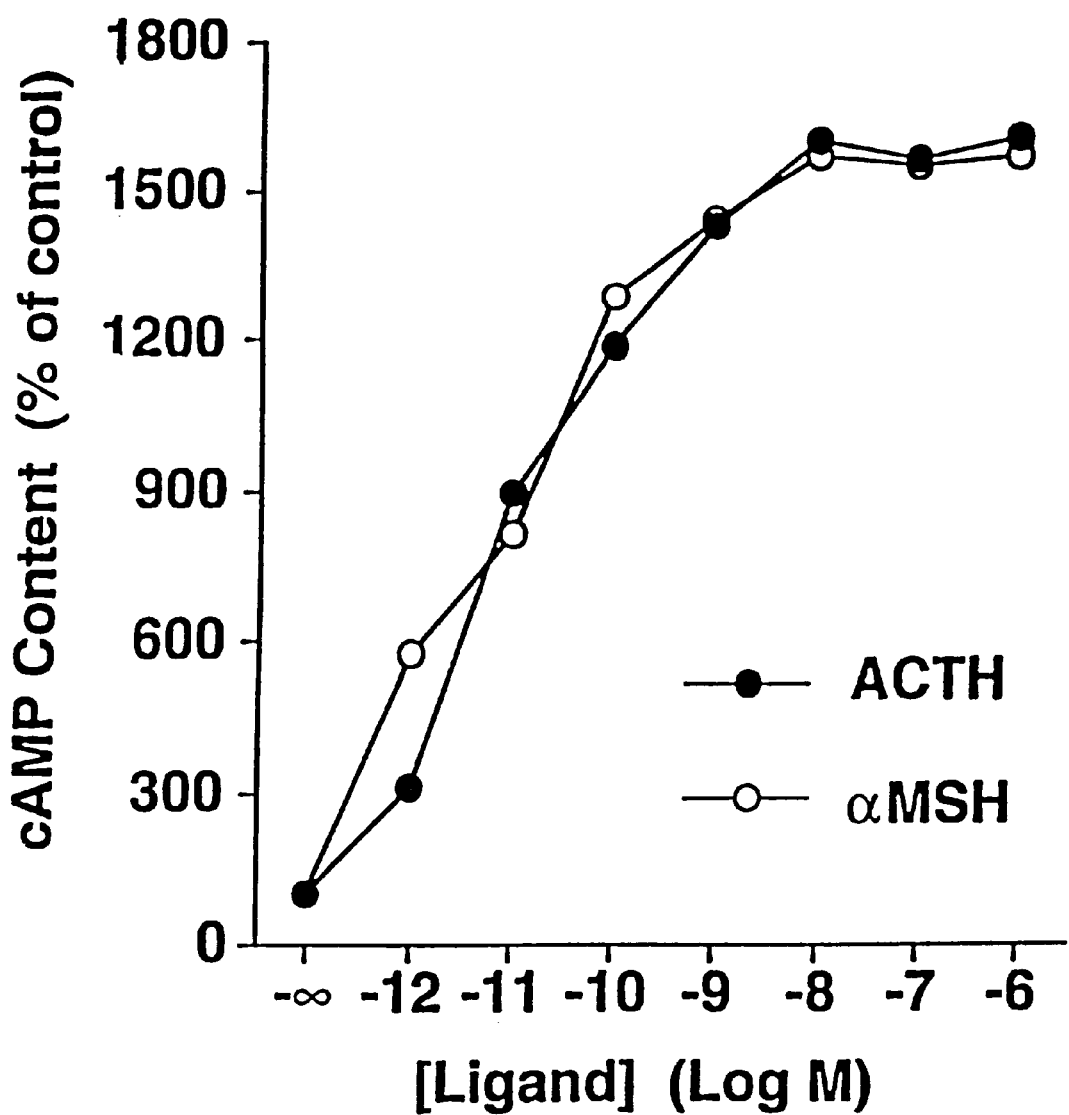
FIGS. 13A and 13B are graphs showing an increase in intracellular cAMP content and total [$^3$H] IP production, respectively, in Hepa cells transfected with the MC3 receptor.
Figure 13B:
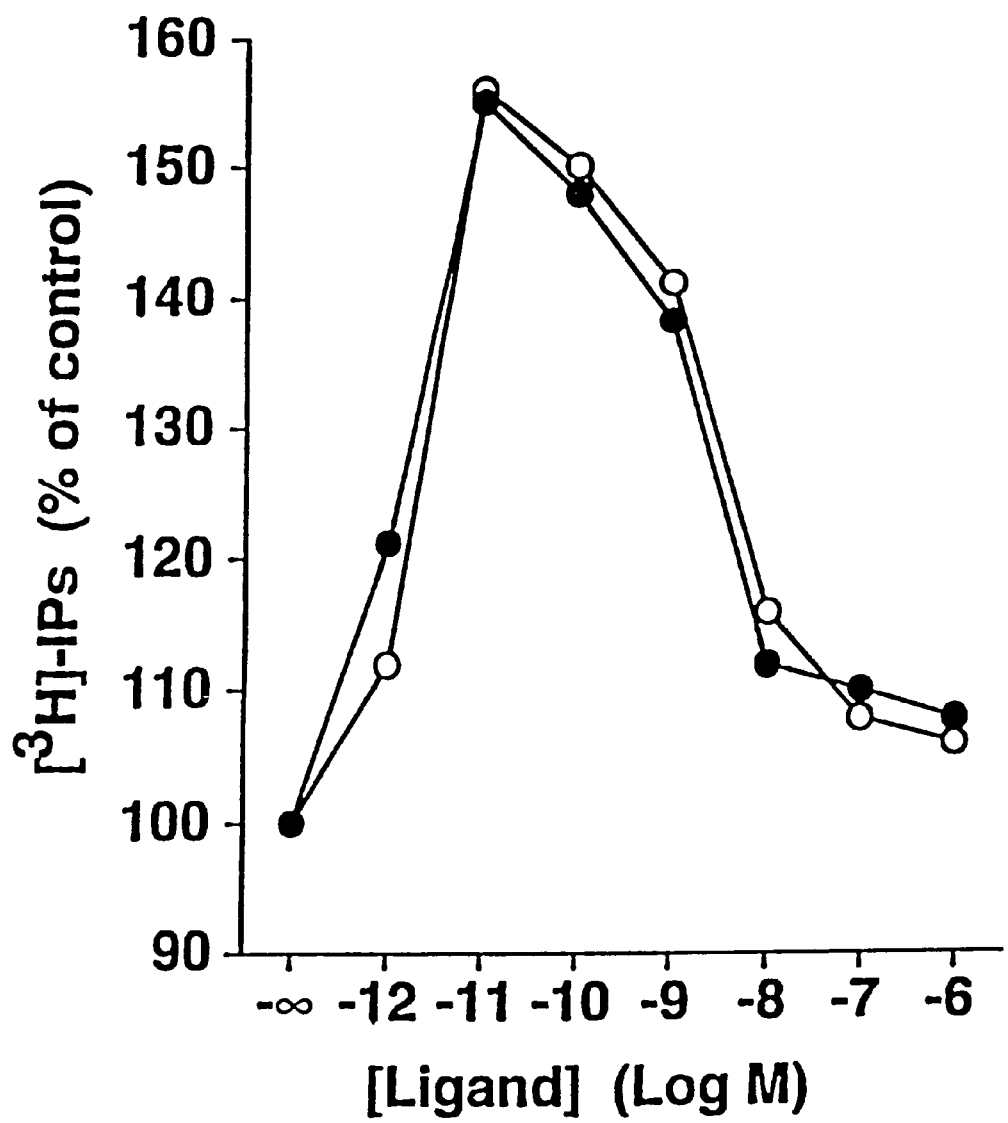
Figure 14:
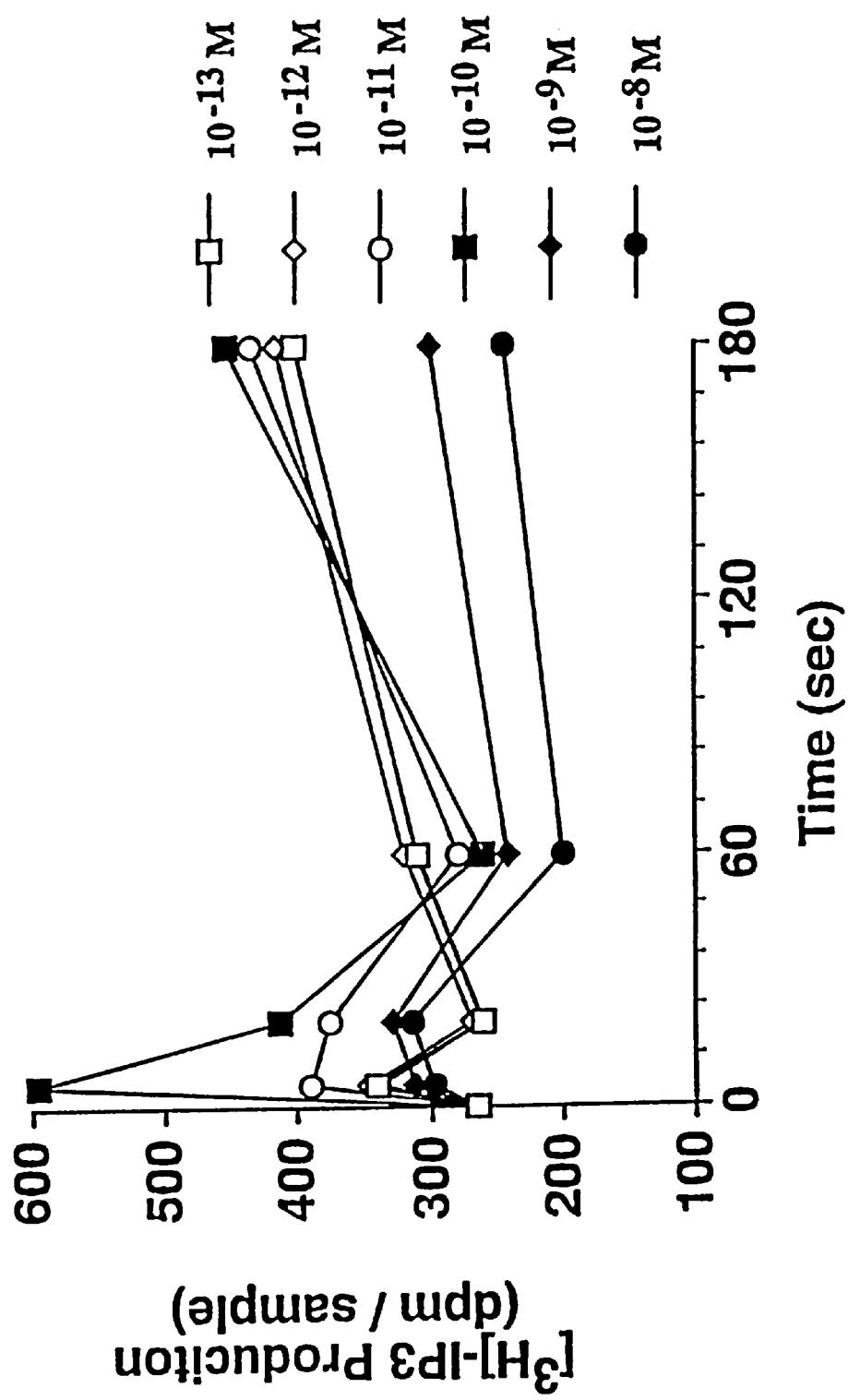
FIG. 14 is a graph showing time dependent generation of [$^3$H] IP3 in Hepa cells in response to varying doses of α-MSH.

Both ACTH and α-MSH stimulated cAMP production in Hepa cells transfected to express the MC3 receptor. These results are depicted in FIGS. 13A and 13B wherein the cells were pre-labeled with [2-$^3$H] myo-inositol and wherein each point represents the average of three experiments with standard error (SE), <10%. Neither peptide had any effect on non-transfected Hepa cells. The stimulatory effect was dose-dependent and monophasic, and cAMP production ultimately exceeded 15 times the control unstimulated levels at maximal doses of hormone. When the effects of ACTH and α-MSH on inositol phospholipid turnover were examined, a remarkably different pattern was observed. At low doses (below $10^{-11}$ M) there was a clear stimulatory effect, however, at higher doses, there was a dose dependent inhibitory effect. Maximal stimulation of [$^3$H]-IP production reached only 155% of basal unstimulated value. To confirm these observations, the time dependent production of [$^3$H]-IP3 was examined in cells pre-labeled with [2-$^3$H] myo-inositol. As shown in FIG. 14, wherein each point represents the average of three experiments with standard error (SE) <10%, there was a rapid initial phase of IP3 production achieved within 5 seconds of exposure to ligand followed by a rapid decrease then a secondary gradual increase. The initial peak is attributable to the production of inositol 1,4,5 trisphosphate while the secondary rise may reflect other events such as the production of inositol 1,3,4 trisphosphate from inositol tetrakisphosphate. The initial phase of the IP3 response was dose-dependent, reaching maximum levels at α-MSH concentrations of $10^{-10}$ M but decreasing in magnitude beyond that dose.

Figure 15:
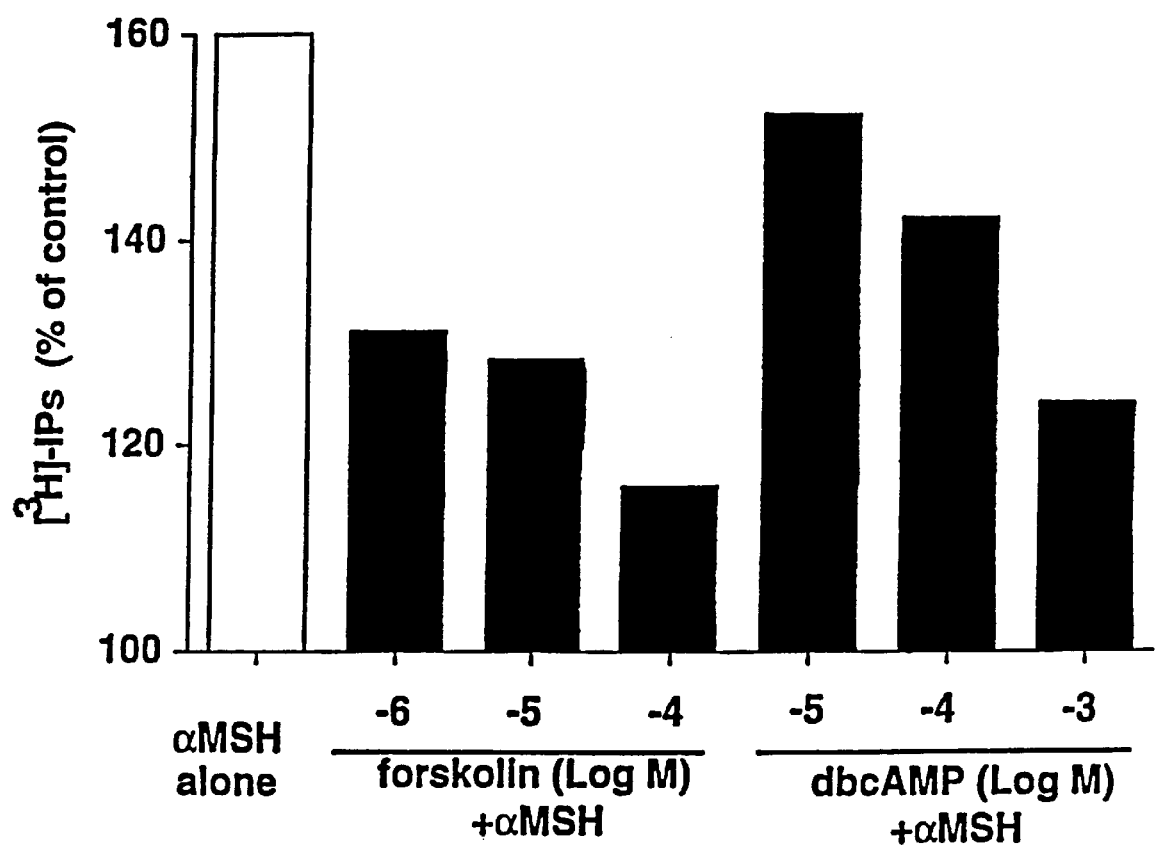
FIG. 15 is a bar graph showing the effect of forskolin and dibutryl cAMP on α-MSH stimulated [$^3$H] IP production in transfected Hepa cells.
Figure 16A:
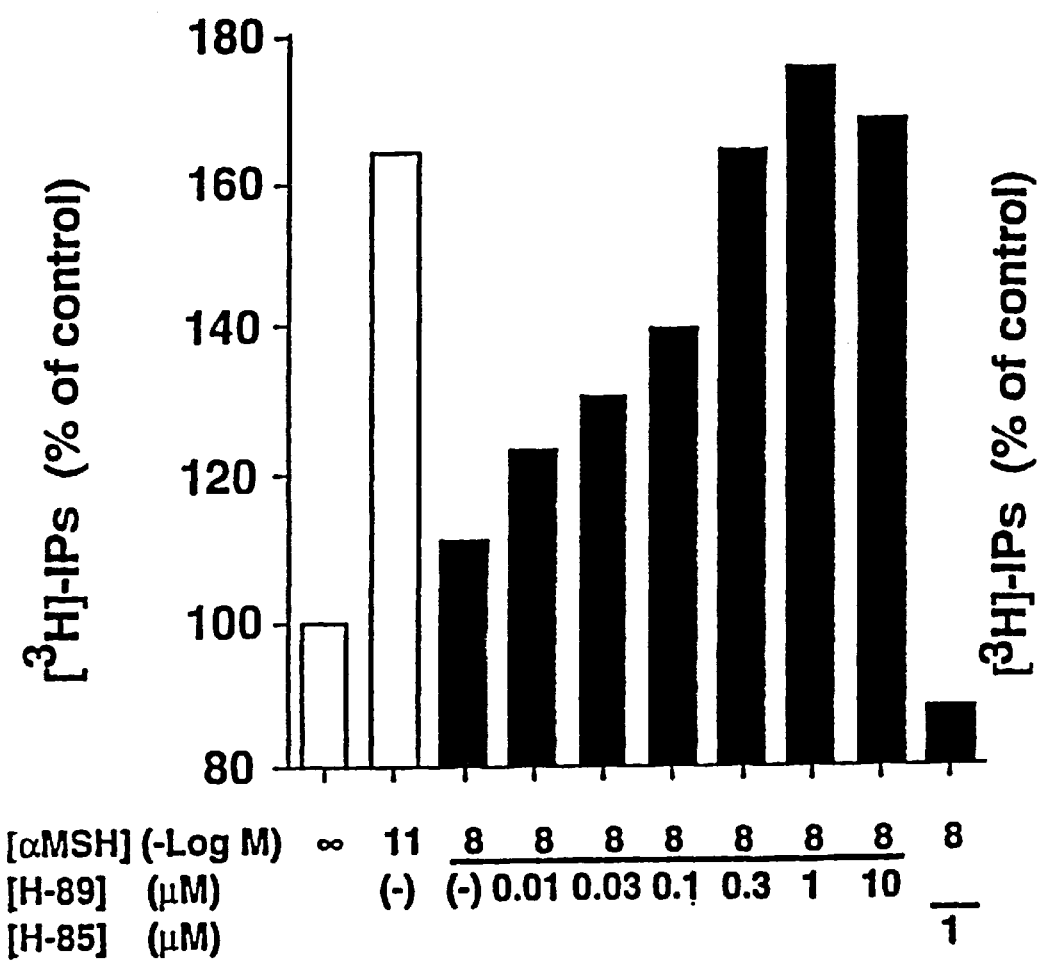
FIGS. 16A and 16B are graphs showing the effect of pretreatment of transfected Hepa cells with the protein kinase A inhibitor H-89 or its inactive analogue H-85 on α-MSH stimulated total [$^3$H] inositol phosphate (IP) production.
Figure 16B:
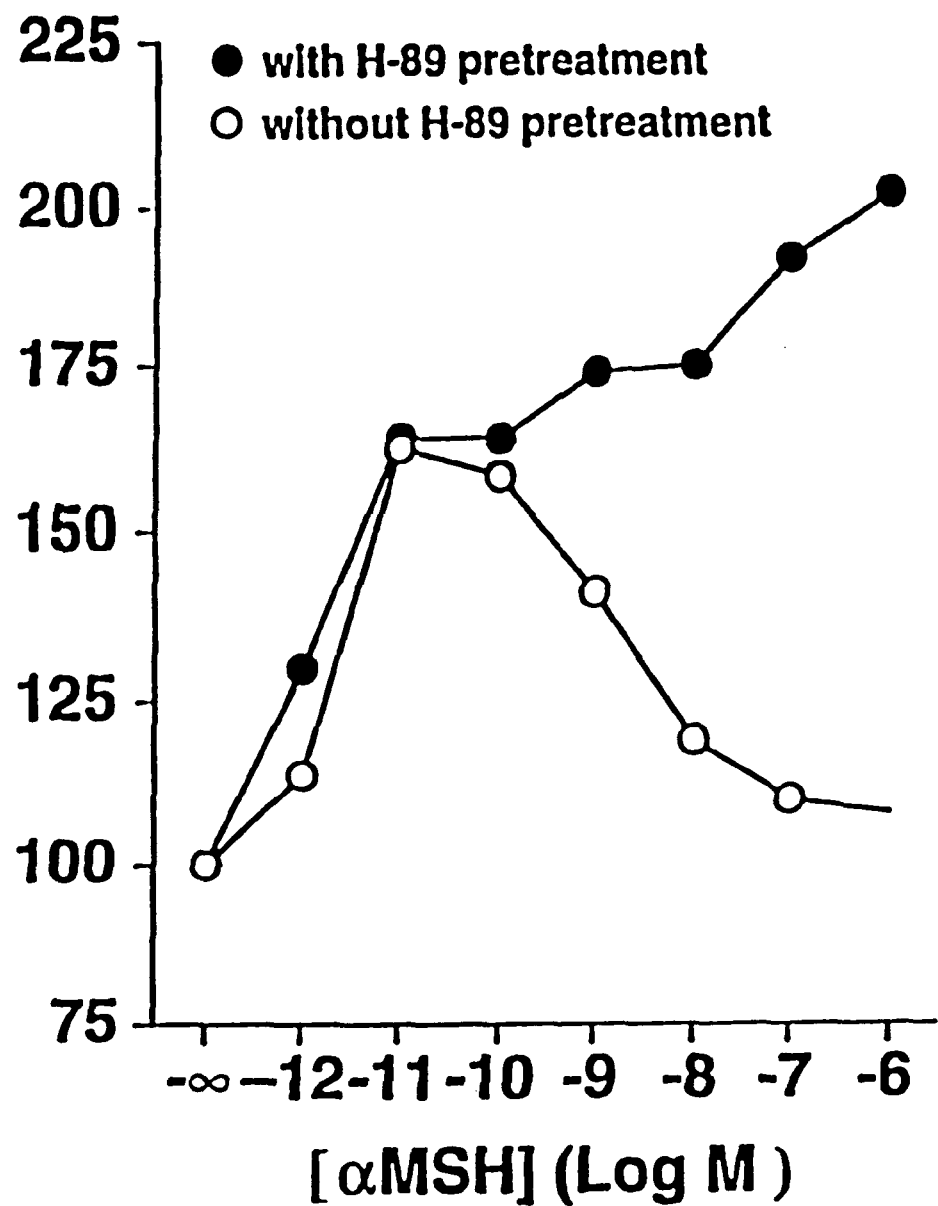

In pursuing the mechanism for the unique differences between the dose-response curves for agonist induced increases in cAMP content and inositol phospholipid turnover in cells transfected with MC3 receptor, the possibility that the two post-receptor events might be linked in some way was examined. Toward this end, the effect of exogenously administered forskolin, a direct stimulant of adenylate cyclase, and the cell-permeable cAMP analogue, dibutryl cAMP (dbcAMP), on peak [$^3$H]-IP generation achieved at a dose of $10^{-11}$ M α-MSH was examined. As shown in FIG. 15, wherein each point represents the average of three experiments with standard error (SE)<10%, both forskolin and dbcAMP dose dependently inhibited the level of [$^3$H]-IP turnover in response to α-MSH. These data suggested that activation of the adenylate cyclase/cAMP post-receptor signaling cascade, which ultimately results in protein kinase A activation, has an inhibitory effect on inositol phospholipid turnover activated via MC3 receptor. To test this hypothesis further, the effect of the selective protein kinase A inhibitor H-89 (Chhajlani, T. et al., *J. Biol. Chem.* 265:5267–5272 (1990)) on [$^3$H]-IP production by α-MSH at doses of $10^{-8}$ M was examined. This dose of α-MSH resulted in [$^3$H]-IP production which is significantly lower than that observed with $10^{-11}$ M α-MSH. As shown in FIG. 16A, wherein each point represents the average of three experiments with standard error (SE)<10%, H-89 pretreatment in conjunction with $10^{-8}$ M α-MSH resulted in the restoration of the higher levels of [$^3$H]-IP products observed with $10^{-11}$ M α-MSH. This effect of H-89 was dose-dependent reaching a maximum effect at 1 μM and its specificity is indicated by the observation that it was not reproduced by H-85, another isoquinoline compound known to have no effect on protein kinase A. Pretreatment with H-89 converted the biphasic dose response curve for [$^3$H]-IP eneration by α-MSH into a more conventional monophasic dose-response curve as observed for cAMP generation as shown in FIG. 16B, wherein each point represents the average of three experiments with standard error (SE)<10%. This data suggests that protein kinase A activation induced by α-MSH acting on MC3 receptor results in inhibition of membrane inositol phospholipid turnover induced by the same ligand acting at the identical receptor.

Figure 17A:
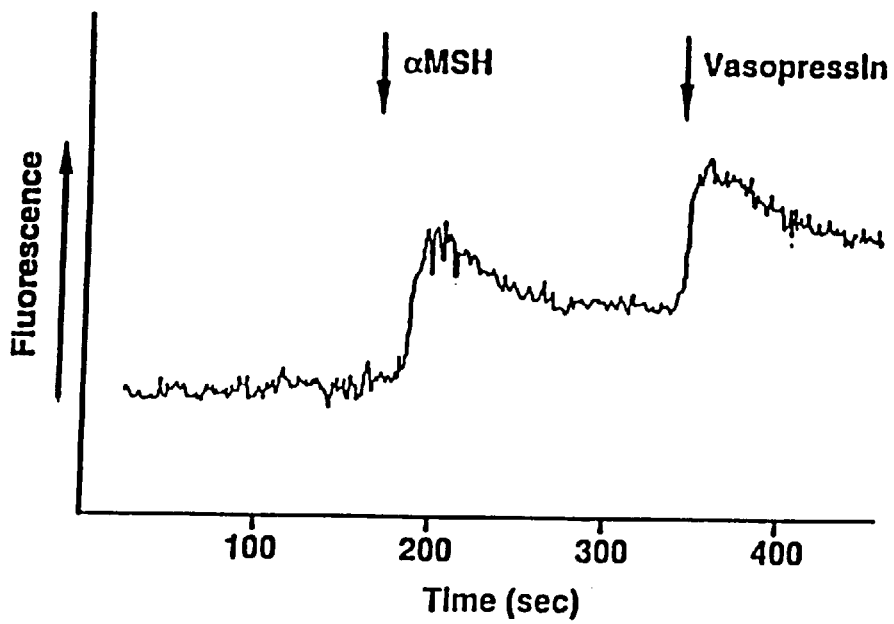
FIGS. 17A, 17B and 17C are a set of graphs showing the effect of α-MSH, vasopressin and EDTA, respectively, on [$Ca^{++}$]i of transfected Hepa cells in the presence or absence of H-89 pretreatment.
Figure 17B:
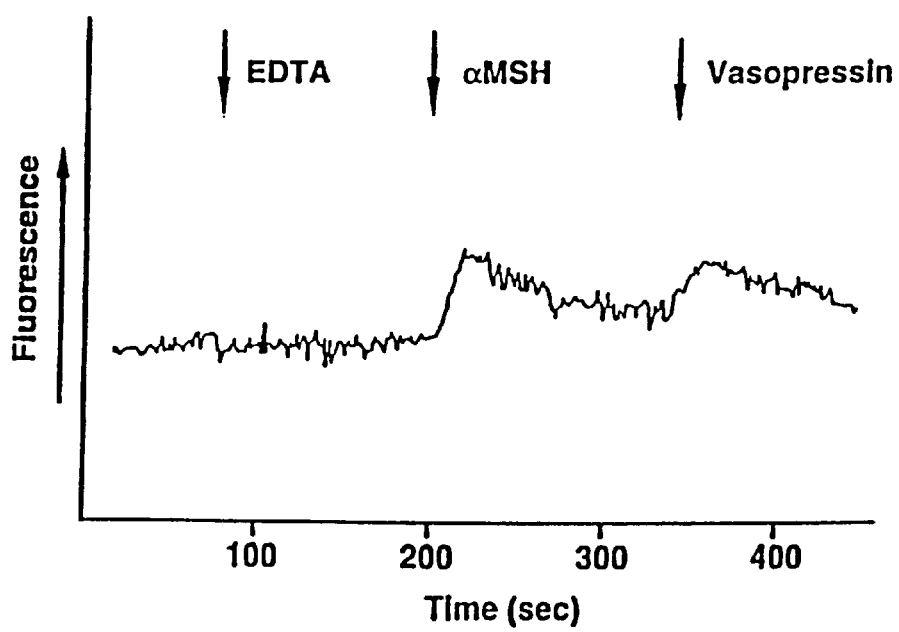
Figure 17C:
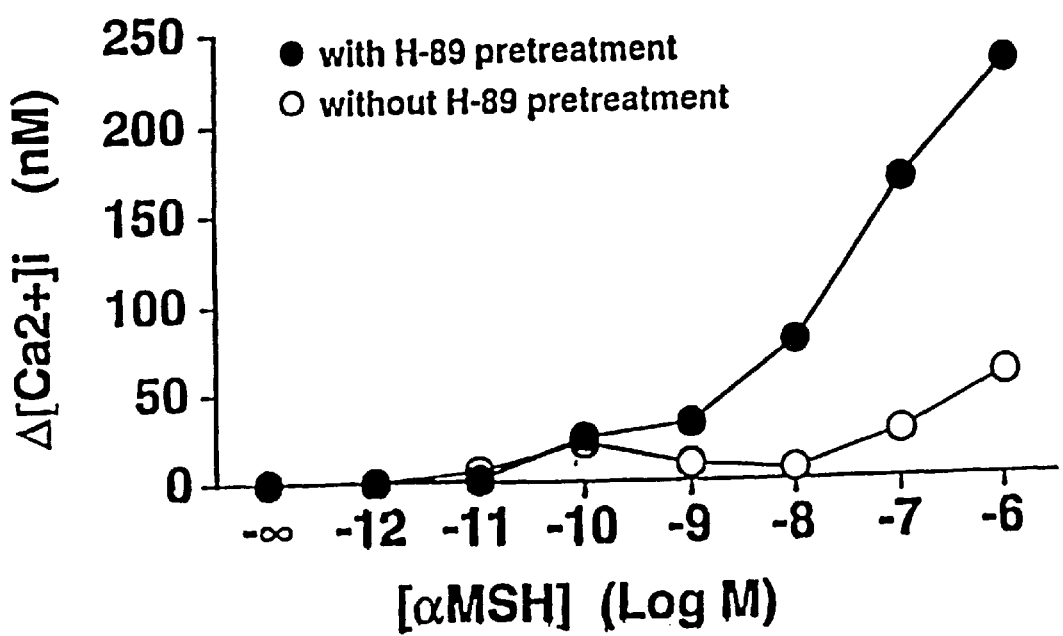
Figure 18A:
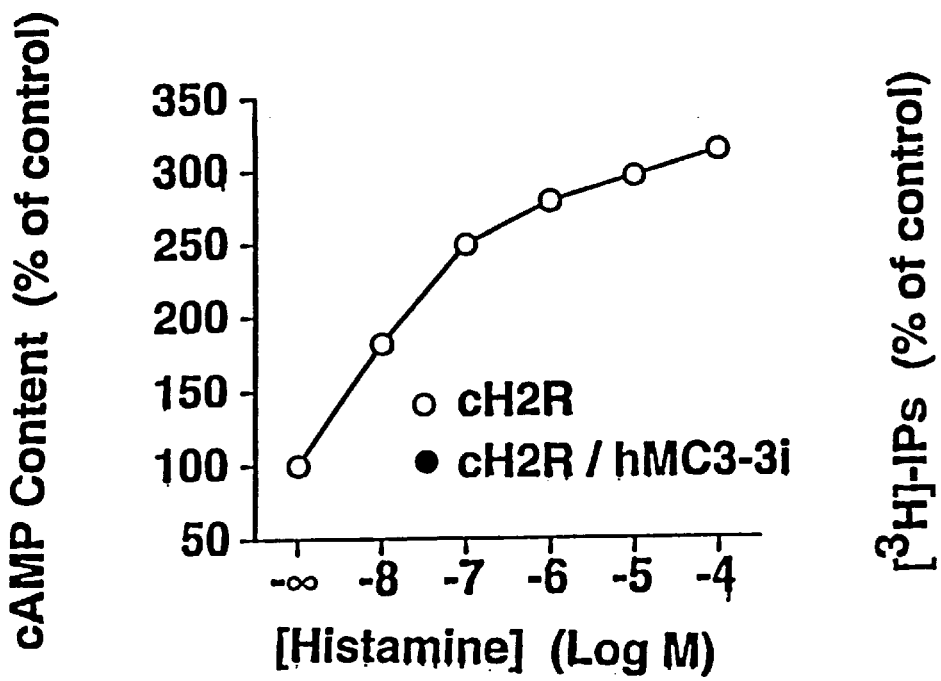
Figure 18B:
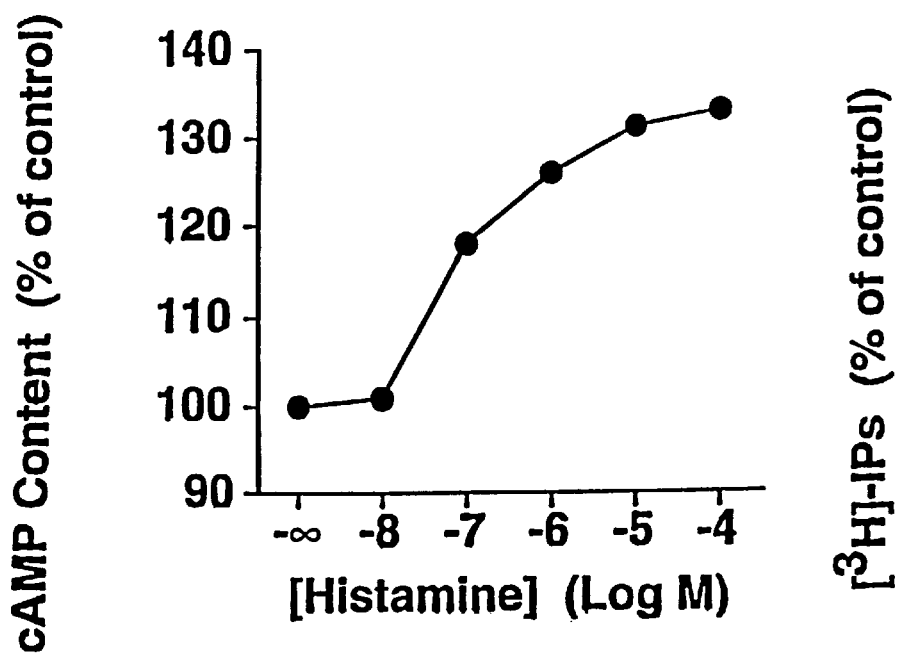
Figure 18C:
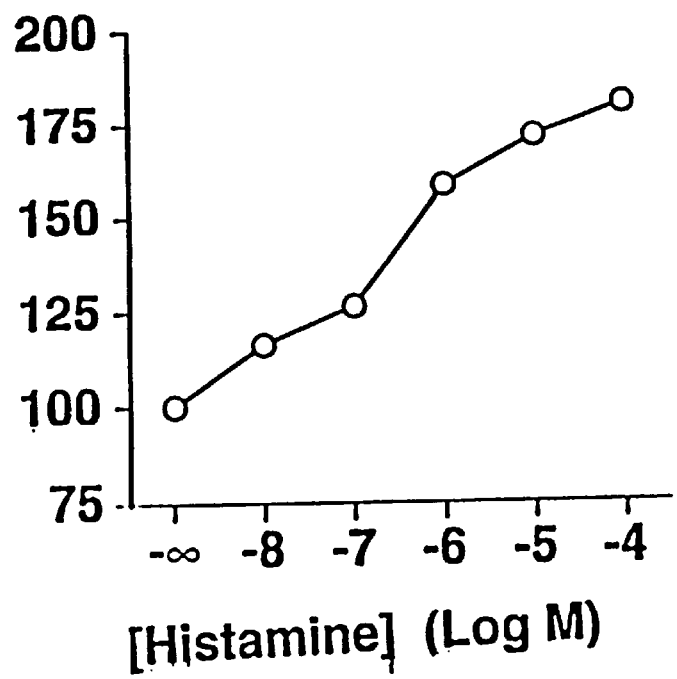
Figure 18D:
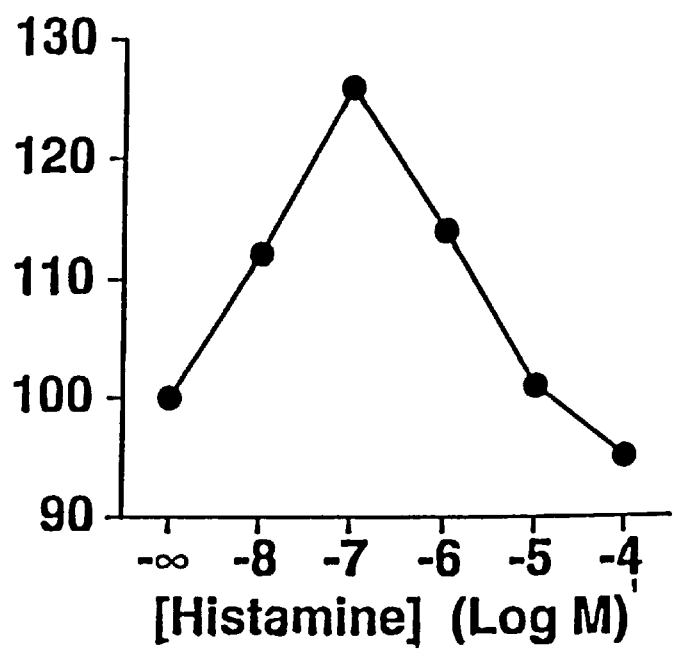

As IP3 is known to induce the mobilization of $Ca^{++}$ from intracellular stores the ability of α-MSH to increase [$Ca^{++}$]i in the transfected cells was examined. The low doses of α-MSH below $10^{-10}$ M which produced the greatest increase in IP3 generation was anticipated to produce the largest increases in [$Ca^{++}$]i. Nevertheless, no effect of α-MSH on [$Ca^{++}$]i was observed even though the Hepa cells demonstrated an increase in [$Ca^{++}$]i upon stimulation of their endogenous vasopressin receptors. However, pretreating the cells with H-89 demonstrated a clear increase in [$Ca^{++}$]i. These results are depicted in FIGS. 17A, 17B and 17C, wherein the initial [$Ca^{++}$]i peaks, rather than the plateau phase of the stimulated [$Ca^{++}$]i responses, were used for this analysis. More specifically, FIG. 17A depicts the effect of αMSH ($10^{-6}$M) and vasopressin ($10^{-7}$) on H-89 pretreated cells in medium containing 1.8 mM$ca^{++}$, FIG. 17B depicts the same in $Ca^{++}$ free medium and EDTA, and FIG. 17C depicts the dose dependency of αMSH induced increases in [$Ca^{++}$]i in the presence or absence of H-89 pre-treatment. These figures further demonstrate that there was an initial peak in [$Ca^{++}$]i followed by a lower but sustained elevation. Although the plateau phase was abolished in $Ca^{++}$-free incubation conditions, the initial phase was not, indicating that it was dependent on mobilization of $Ca^{++}$ from intracellular stores. These data imply that in addition to inhibition of IP3 generation, protein kinase A activation may also inhibit IP3 mediated increases in [$Ca^{++}$]i.

The unique nature of the interaction between the dual signaling pathways activated by ligand action at the MC3 receptor suggests that it may be mediated by a novel interaction between the receptor protein and the various G-proteins involved in post-receptor events. In studies with other G-protein linked receptors the third intracytoplasmic loop (3i) has been shown to be important in the signaling mechanism. Caron, M. G. et al., *J. Biol. Chem.* 263:4993–4996 (1988). Accordingly, the possibility that MC3R-3i is a determinant in the observed biphasic pattern of the inositol phospholipid turnover induced by α-MSH was examined. For these studies, a chimeric H2-histamine receptor with the 3i portion of the MC3 receptor inserted in place of cH2R-3i was used. As previously noted and as shown in FIG. 18, the wild-type H2-histamine receptor demonstrated monophasic dose-dependent increases in both cAMP and [$^3$H]-IP production in response to histamine stimulation. In contrast, the chimeric H2-histamine receptor demonstrated signaling properties more characteristic of the MC3 receptor with a monophasic cAMP dose-response curve, but a biphasic dose-response curve for [$^3$H]-IP production. As in the case of the MC3 receptor the inhibitory phase of the latter dose response curve was abolished by pretreatment with H-89. Thus, the 3i portion of the MC3 receptor appears to be responsible for conferring the unusual biphasic property to the effect of α-MSH on inositol phospholipid turnover in transfected Hepa cells.

The capacity of a cloned receptor to couple to both cAMP and inositol phospholipid/$Ca^{++}$ mediated signal transduction cascades has been observed previously with numerous members of the superfamily of seven transmembrane G-protein linked receptors including H2-histamine (DelValle, J. et al, *Am. J. Physiol* 263:420–426 (1992)), muscarinic (m1–m4) (Peralta, E. G. et al., *Nature* 334:434–437 (1988)), adrenergic (Cotecchia, S. et al., *J. Biol. Chem.* 265:63–69 (1990)), luteinizing hormone (Gudermann, T. et al., *J. Biol. Chem.* 267:4479–4488 (1992)), thyroid stimulating hormone (Van Sande, J. et al., *Mol. Cell Endocrinol.* 74:R1–R6 (1990)), calcitonin (Chabre, O. et al., *Mol. Endocrinol.* 6:551–555 (1992)), tachykinin (Nakaima, Y. et al., *J. Biol. Chem.* 267:2437–2442 (1992)), and glucagon (Jelinek, L. J. et al., *Science* 259:1614–1616 (1993)) receptors. Indeed, while these receptors all demonstrate one predominant signal transduction pathway, the ability to couple to multiple pathways via a single receptor appears to be a relatively common feature of this class of membrane receptors even though the physiological significance of this property is unclear. One concern with the observation of dual signaling by cloned receptors expressed in heterologous cells is that it might represent an artifact of transfection, perhaps resulting from an unusual interaction of the foreign receptor with the endogenous signal transduction machinery of the host cell or to over-expression of the cloned receptor in the presence of limited machinery for linkage to any single signaling system. In the case of MC3 receptor, the physiological nature of the dual signaling linkage is supported by similar observation made on the effects of ACTH on cultured adrenal cortical cells (Woodcock, E. A., *Mol. Cell Endo.* 63:247–253 (1989) and Buffey, J. et al., *J. Endocrinol.* 133:333–340 (1992)) presumably via the ACTH receptor (MC2 receptor). Others have noted the same biphasic IP3 and calcium responses at identical agonist doses. Farese, R. V. et al., *Biochem. Biophys. Res. Comm.* 135:742–748 (1986). Although experiments were performed using primary cultured cells, thus making it impossible to implicate a single receptor class unequivocally, expression of only MC2 receptor in adrenal cortical cells has been identified. The biphasic nature of the inositol phospholipid response noted by MC2 receptor in these studies and by MC3 receptor in the studies herein, coupled with preliminary evidence that the same property is shared by the MC4 receptor (Konda, Gantz, and Yamada unpublished) indicates that it may be an unique characteristic of the melanocortin receptor family of seven transmembrane G-protein linked receptors.

These experiments resulted in a highly unusual divergence in the dose-response curves for MC3 receptor-mediated cAMP generation and membrane inositol phospholipid turnover. The data are consistent with the notion that the production of IP3 induced by MC3 receptor activation is regulated by a protein kinase A mediated phosphorylation event. The exact target for phosphorylation has not been determined from these experiments. One possibility is that phosphorylation of the receptor itself occurs resulting in selective "desensitization" of the inositol phosphate response. Hausdorff, W. P. et al., *FASEB J.* 4:2881–2889 (1990) However, a consensus phosphorylation site (Kennelly, P. J. et al., *J. Biol. Chem.* 266:1555–1558 (1991)) in the 3i of the MC3 receptor which appears to be capable of conferring the biphasic dose-response curve for IP3 production to the chimeric cH2R/MC3R-3i has not been identified. Nevertheless, this observation does not exclude the possibility that a consensus protein kinase A phosphorylation site elsewhere on the MC3 receptor (or cH2R) might influence the structural conformation of the 3i and thus alter its linkage to the specific G-protein responsible for inducing inositol phospholipid turnover. Equally plausible from these results is that phosphorylation of a protein quite remote from the receptor such as the G-protein complex or phospholipase involved in IP3 generation (Rhee, S. G. et al., "Advances in Second Messenger and Phosphoprotein Research," (Brown, B. L. and Dobson, R. M. eds) Vol. 28, pp. 57–64 (Raven Press, NY 1993)) accounts for the biphasic dose-response curve. The observation that even in the presence of increased IP3 production, such as seen at the $10^{-11}$ M dose of α-MSH, no increase in [$Ca^{++}$]i was induced unless the transfected cells were pre-treated with H-89 suggest that the IP3 receptor may also be a target for protein kinase A phosphorylation. Rhee, S. G. et al., "Advances in Second Messenger and Phosphoprotein Research," (Brown, B. L. and Dobson, R. M. eds) Vol. 28, pp. 57–64 (Raven Press, NY 1993). The physiologic significance of the divergent effects of the MC3 receptor on CAMP generation and IP3 production has yet to be determined. However, the observation that ACTH has an inhibitory effect on angiotensin II stimulated inositol phospholipid turnover in adrenal glomerulosa cells (Woodcock, E. A., *Mol. Cell Endo.* 63:247–253 (1989)) suggests that the effect of protein kinase A activation by melanocortin receptors on IP3 generation may extend beyond the boundary between separate receptors on the same cell.

SPECIFIC EXAMPLE 5

CHROMOSOME LOCALIZATION

Materials and Methods

Chromosome Localization. Chromosome localization was performed with assistance of the University of Michigan Genome Center using the fluorescent in situ hybridization (FISH) technique according to a modification of the protocols of Pinkel, D. et al., *PNAS (USA)* 83:2934–2938 (1986), Lichter, P. et al., *Science* 247:64–69 (1990), and Lemieux, N. et al., *Cytogenet. Cell Genet.* 59:311–312 (1992). Metaphase chromosomes from a normal female were prepared from peripheral blood lymphocytes following overnight synchronization with 5-bromodeoxyuridine and thymidine release. Cells were harvested and slides were prepared using standard cytogenetic techniques. EMBL3 phage containing genomic inserts of between 10 and 20 kilobases of DNA surrounding and including the melanocortin receptor sequences were biotinylated using a Bionick kit (Life Technologies Inc.). Unincorporated nucleotides were removed using a Sephadex G-50 column. An aliquot (330 ng) of biotinylated DNA was precipitated with 3 µg of Cot-1 DNA and 7 µg of herring testes DNA and resuspended in 10 µl of hybridization mixture (50% formamide/2×SSC/10% dextran sulfate). The probe was denatured for 5 min at 70° C. and preannealed for 15 min at 37° C. Slides were pretreated with RNase and proteinase K and fixed with 4% paraformaldehyde. They were then denatured in 70% formamide, 2×SSC (pH 7.0) for 5 min, followed by dehydration in an ice-cold ethanol series. The preannealed probe mixture was applied to the denatured slide under a sealed 22-mm square coverslip, placed in a moist chamber, and incubated overnight at 37° C. Post-hybridization washed were at 37° C. in 50% formamide, 2×SSC (pH 7.0), followed by washes in 0.1×SSC at 42° C., and a final wash of 4×SSC at room temperature. Slides were preblocked with 4×SSC, 3% bovine serum albumin for 60 min at 37° C. Signal detection was achieved by incubations of 30 min at 37° C. with fluorescein goat antibiotin and fluorescein-labeled antigoat 1 gG (Vector, Burlingame, Calif.) in 4×SSC/0.1% Tween/1% bovine serum albumin. Each incubation was followed by washes in 4×SSC/0.1% Tween at 37° C. Slides were counterstained with propidium iodide, rinsed in phosphate-buffered saline (2.68 mM potassium chloride, 1.76 mM anhydrous monobasic potassium phosphate, 137 mM sodium chloride, 10 mM anhydrous dibasic sodium phosphate) and coverslipped with PPD11 anti-fade solution (100 mg of p-phenylenediamine free base diluted in 100 ml of 9 parts glycerol to 1 part phosphate-buffered saline, adjusted to pH 11.0 with 1 M NaOH, and stored at –20° C.). Photographs were taken on Kodak ASA 400 Gold film using a Zeiss Axioskop epifluorescence microscope equipped with a Zeiss filter set allowing simultaneous visualization of fluorescein isothiocyanate and propidium iodide.

Results

The gene encoding the MC4 receptor was localized by fluorescent in situ hybridization to chromosome 18(q21.3). Gantz et al., *J. Biol. Chem.* 268:15174–15179 (1993). Other genes localized to this site include those encoding the proto-oncogene bcl-2 (Tsujimoto, Y. et al., *PNAS (USA)* 83:5214–5218 (1986)) and plasminogen activator inhibitor type 11 (Samia, J. A. et al., *Genomics* 6:159–167 (1990)), neither of which has any relationship to G-protein-linked receptors. The gene encoding the MC2 receptor gene is found on the opposite arm of the same chromosome, 18 (p11.2). By contrast, the MC3 receptor gene is found on a completely different chromosome 20(q13.2–q13.3). The chromosomal localization of the MC1 receptor gene is localized to 16q24.3.

The foregoing discussion discloses and describes merely exemplary embodiments of the present invention. One skilled in the art will readily recognize from such discussion, and from the accompanying drawings and claims, that various changes, modifications and variations can be made therein without departing from the spirit and scope of the invention as defined in the following claims.

All publications cited herein are incorporated by reference.

What is claimed is:

1. A substantially pure polypeptide encoded by the nucleic acid of Sequence Listing ID No. 5.

2. A substantially pure polypeptide encoded by the nucleic acid of Sequence Listing ID No. 7.

3. Substantially pure melanocortin-4 receptor protein which is encoded by a nucleic acid molecule comprising a nucleotide sequence which hybridizes to the nucleic acid comprising the nucleotide sequence of Sequence Listing ID No. 7 in 6XSSC at 42° C. followed by washing with 1XSSC at 55° C.

4. A substantially pure polypeptide comprising the amino acid sequence of Sequence Listing ID No. 6.

5. A substantially pure polypeptide comprising the amino acid sequence of Sequence Listing ID No. 8.

* * * * *

SEQUENCE LISTING (1) GENERAL INFORMATION:

(iii) NUMBER OF SEQUENCES: 23

(2) INFORMATION FOR SEQ ID NO:1:

(i) SEQUENCE CHARACTERISTICS:
      (A) LENGTH: 951 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Homo sapiens (ix) FEATURE:
      (A) NAME/KEY: CDS
      (B) LOCATION: 1..951

(ix) FEATURE:
      (A) NAME/KEY: conflict
      (B) LOCATION: order(269..270, 488, 490..491)

(D) OTHER INFORMATION: /note= "Differs from sequence
    published by Chhajlani and Wikberg in
    five nucleotide and three amino acid
    positions."

(ix) FEATURE:
    (A) NAME/KEY: conflict
    (B) LOCATION: order(485, 488)
    (D) OTHER INFORMATION: /note= "Differs from sequence
        published by Mountjoy, Robbins,
        Mortrud and Cone in 2 nucleotide and 2
        amino acid positions."

(xi) SEQUENCE DESCRIPTION: SEQ ID NO:1:

| | | | | | | | | | | | | | | | | |
|---|---|---|---|---|---|---|---|---|---|---|---|---|---|---|---|---|
| ATG | GCT | GTG | CAG | GGA | TCC | CAG | AGA | AGA | CTT | CTG | GGC | TCC | CTC | AAC | TCC | 48 |
| Met | Ala | Val | Gln | Gly | Ser | Gln | Arg | Arg | Leu | Leu | Gly | Ser | Leu | Asn | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ACC | CCC | ACA | GCC | ATC | CCC | CAG | CTG | GGG | CTG | GCT | GCC | AAC | CAG | ACA | GGA | 96 |
| Thr | Pro | Thr | Ala | Ile | Pro | Gln | Leu | Gly | Leu | Ala | Ala | Asn | Gln | Thr | Gly | |
| | | | 20 | | | | | 25 | | | | | 30 | | | |

| | | | | | | | | | | | | | | | | |
|---|---|---|---|---|---|---|---|---|---|---|---|---|---|---|---|---|
| GCC | CGG | TGC | CTG | GAG | GTG | TCC | ATC | TCT | GAC | GGG | CTC | TTC | CTC | AGC | CTG | 144 |
| Ala | Arg | Cys | Leu | Glu | Val | Ser | Ile | Ser | Asp | Gly | Leu | Phe | Leu | Ser | Leu | |
| | | 35 | | | | | 40 | | | | | 45 | | | | |

| | | | | | | | | | | | | | | | | |
|---|---|---|---|---|---|---|---|---|---|---|---|---|---|---|---|---|
| GGG | CTG | GTG | AGC | TTG | GTG | GAG | AAC | GCG | CTG | GTG | GTG | GCC | ACC | ATC | GCC | 192 |
| Gly | Leu | Val | Ser | Leu | Val | Glu | Asn | Ala | Leu | Val | Val | Ala | Thr | Ile | Ala | |
| | 50 | | | | | 55 | | | | | 60 | | | | | |

| | | | | | | | | | | | | | | | | |
|---|---|---|---|---|---|---|---|---|---|---|---|---|---|---|---|---|
| AAG | AAC | CGG | AAC | CTG | CAC | TCA | CCC | ATG | TAC | TGC | TTC | ATC | TGC | TGC | CTG | 240 |
| Lys | Asn | Arg | Asn | Leu | His | Ser | Pro | Met | Tyr | Cys | Phe | Ile | Cys | Cys | Leu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| GCC | TTG | TCG | GAC | CTG | CTG | GTG | AGC | GGG | ACG | AAC | GTG | CTG | GAG | ACG | GCC | 288 |
| Ala | Leu | Ser | Asp | Leu | Leu | Val | Ser | Gly | Thr | Asn | Val | Leu | Glu | Thr | Ala | |
| | | | | 85 | | | | | 90 | | | | | 95 | | |

| | | | | | | | | | | | | | | | | |
|---|---|---|---|---|---|---|---|---|---|---|---|---|---|---|---|---|
| GTC | ATC | CTC | CTG | CTG | GAG | GCC | GGT | GCA | CTG | GTG | GCC | CGG | GCT | GCG | GTG | 336 |
| Val | Ile | Leu | Leu | Leu | Glu | Ala | Gly | Ala | Leu | Val | Ala | Arg | Ala | Ala | Val | |
| | | | | 100 | | | | | 105 | | | | | 110 | | |

| | | | | | | | | | | | | | | | | |
|---|---|---|---|---|---|---|---|---|---|---|---|---|---|---|---|---|
| CTG | CAG | CAG | CTG | GAC | AAT | GTC | ATT | GAC | GTG | ATC | ACC | TGC | AGC | TCC | ATG | 384 |
| Leu | Gln | Gln | Leu | Asp | Asn | Val | Ile | Asp | Val | Ile | Thr | Cys | Ser | Ser | Met | |
| | | 115 | | | | | 120 | | | | | 125 | | | | |

| | | | | | | | | | | | | | | | | |
|---|---|---|---|---|---|---|---|---|---|---|---|---|---|---|---|---|
| CTG | TCC | AGC | CTC | TGC | TTC | CTG | GGC | GCC | ATC | GCC | GTG | GAC | CGC | TAC | ATC | 432 |
| Leu | Ser | Ser | Leu | Cys | Phe | Leu | Gly | Ala | Ile | Ala | Val | Asp | Arg | Tyr | Ile | |
| | | 130 | | | | | 135 | | | | | 140 | | | | |

| | | | | | | | | | | | | | | | | |
|---|---|---|---|---|---|---|---|---|---|---|---|---|---|---|---|---|
| TCC | ATC | TTC | TAC | GCA | CTG | CGC | TAC | CAC | AGC | ATC | GTG | ACC | CTG | CCG | CGG | 480 |
| Ser | Ile | Phe | Tyr | Ala | Leu | Arg | Tyr | His | Ser | Ile | Val | Thr | Leu | Pro | Arg | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| GCG | CGG | CAA | GCC | GTT | GCG | GCC | ATC | TGG | GTG | GCC | AGT | GTC | GTC | TTC | AGC | 528 |
| Ala | Arg | Gln | Ala | Val | Ala | Ala | Ile | Trp | Val | Ala | Ser | Val | Val | Phe | Ser | |
| | | | | 165 | | | | | 170 | | | | | 175 | | |

| | | | | | | | | | | | | | | | | |
|---|---|---|---|---|---|---|---|---|---|---|---|---|---|---|---|---|
| ACG | CTC | TTC | ATC | GCC | TAC | TAC | GAC | CAC | GTG | GCC | GTC | CTG | CTG | TGC | CTC | 576 |
| Thr | Leu | Phe | Ile | Ala | Tyr | Tyr | Asp | His | Val | Ala | Val | Leu | Leu | Cys | Leu | |
| | | | | 180 | | | | | 185 | | | | | 190 | | |

| | | | | | | | | | | | | | | | | |
|---|---|---|---|---|---|---|---|---|---|---|---|---|---|---|---|---|
| GTG | GTC | TTC | TTC | CTG | GCT | ATG | CTG | GTG | CTC | ATG | GCC | GTG | CTG | TAC | GTC | 624 |
| Val | Val | Phe | Phe | Leu | Ala | Met | Leu | Val | Leu | Met | Ala | Val | Leu | Tyr | Val | |
| | | | 195 | | | | | 200 | | | | | 205 | | | |

| | | | | | | | | | | | | | | | | |
|---|---|---|---|---|---|---|---|---|---|---|---|---|---|---|---|---|
| CAC | ATG | CTG | GCC | CGG | GCC | TGC | CAG | CAC | GCC | CAG | GGC | ATC | GCC | CGG | CTC | 672 |
| His | Met | Leu | Ala | Arg | Ala | Cys | Gln | His | Ala | Gln | Gly | Ile | Ala | Arg | Leu | |
| | | 210 | | | | | 215 | | | | | 220 | | | | |

| | | | | | | | | | | | | | | | | |
|---|---|---|---|---|---|---|---|---|---|---|---|---|---|---|---|---|
| CAC | AAG | AGG | CAG | CGC | CCG | GTC | CAC | CAG | GGC | TTT | GGC | CTT | AAA | GGC | GCT | 720 |
| His | Lys | Arg | Gln | Arg | Pro | Val | His | Gln | Gly | Phe | Gly | Leu | Lys | Gly | Ala | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| GTC | ACC | CTC | ACC | ATC | CTG | CTG | GGC | ATT | TTC | TTC | CTC | TGC | TGG | GGC | CCC | 768 |
| Val | Thr | Leu | Thr | Ile | Leu | Leu | Gly | Ile | Phe | Phe | Leu | Cys | Trp | Gly | Pro | |
| | | | | 245 | | | | | 250 | | | | | 255 | | |

```
TTC TTC CTG CAT CTC ACA CTC ATC GTC CTC TGC CCC GAG CAC CCC ACG          816
Phe Phe Leu His Leu Thr Leu Ile Val Leu Cys Pro Glu His Pro Thr
            260                 265                 270

TGC GGC TGC ATC TTC AAG AAC TTC AAC CTC TTT CTC GCC CTC ATC ATC          864
Cys Gly Cys Ile Phe Lys Asn Phe Asn Leu Phe Leu Ala Leu Ile Ile
        275                 280                 285

TGC AAT GCC ATC ATC GAC CCC CTC ATC TAC GCC TTC CAC AGC CAG GAG          912
Cys Asn Ala Ile Ile Asp Pro Leu Ile Tyr Ala Phe His Ser Gln Glu
    290                 295                 300

CTC CGC AGG ACG CTC AAG GAG GTG CTG ACA TGC TCC TGG                      951
Leu Arg Arg Thr Leu Lys Glu Val Leu Thr Cys Ser Trp
305                 310                 315
```

(2) INFORMATION FOR SEQ ID NO:2:

(i) SEQUENCE CHARACTERISTICS:
        (A) LENGTH: 317 amino acids
        (B) TYPE: amino acid
        (D) TOPOLOGY: linear (ii) MOLECULE TYPE: protein (xi) SEQUENCE DESCRIPTION: SEQ ID NO:2:

```
Met Ala Val Gln Gly Ser Gln Arg Arg Leu Leu Gly Ser Leu Asn Ser
1               5                   10                  15

Thr Pro Thr Ala Ile Pro Gln Leu Gly Leu Ala Ala Asn Gln Thr Gly
            20                  25                  30

Ala Arg Cys Leu Glu Val Ser Ile Ser Asp Gly Leu Phe Leu Ser Leu
        35                  40                  45

Gly Leu Val Ser Leu Val Glu Asn Ala Leu Val Val Ala Thr Ile Ala
    50                  55                  60

Lys Asn Arg Asn Leu His Ser Pro Met Tyr Cys Phe Ile Cys Cys Leu
65                  70                  75                  80

Ala Leu Ser Asp Leu Leu Val Ser Gly Thr Asn Val Leu Glu Thr Ala
                85                  90                  95

Val Ile Leu Leu Leu Glu Ala Gly Ala Leu Val Ala Arg Ala Ala Val
            100                 105                 110

Leu Gln Gln Leu Asp Asn Val Ile Asp Val Ile Thr Cys Ser Ser Met
        115                 120                 125

Leu Ser Ser Leu Cys Phe Leu Gly Ala Ile Ala Val Asp Arg Tyr Ile
    130                 135                 140

Ser Ile Phe Tyr Ala Leu Arg Tyr His Ser Ile Val Thr Leu Pro Arg
145                 150                 155                 160

Ala Arg Gln Ala Val Ala Ala Ile Trp Val Ala Ser Val Val Phe Ser
                165                 170                 175

Thr Leu Phe Ile Ala Tyr Tyr Asp His Val Ala Val Leu Leu Cys Leu
            180                 185                 190

Val Val Phe Phe Leu Ala Met Leu Val Leu Met Ala Val Leu Tyr Val
        195                 200                 205

His Met Leu Ala Arg Ala Cys Gln His Ala Gln Gly Ile Ala Arg Leu
    210                 215                 220

His Lys Arg Gln Arg Pro Val His Gln Gly Phe Gly Leu Lys Gly Ala
225                 230                 235                 240

Val Thr Leu Thr Ile Leu Leu Gly Ile Phe Phe Leu Cys Trp Gly Pro
                245                 250                 255

Phe Phe Leu His Leu Thr Leu Ile Val Leu Cys Pro Glu His Pro Thr
            260                 265                 270
```

```
Cys Gly Cys Ile Phe Lys Asn Phe Asn Leu Phe Leu Ala Leu Ile Ile
            275                 280                 285

Cys Asn Ala Ile Ile Asp Pro Leu Ile Tyr Ala Phe His Ser Gln Glu
            290                 295                 300

Leu Arg Arg Thr Leu Lys Glu Val Leu Thr Cys Ser Trp
305                 310                 315

(2) INFORMATION FOR SEQ ID NO:3:

(i) SEQUENCE CHARACTERISTICS:
        (A) LENGTH: 1015 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: CDS
        (B) LOCATION: 79..969

(xi) SEQUENCE DESCRIPTION: SEQ ID NO:3:
```

```
AGGATCCTGA AGAATCAATC AAGTTTTCCG TGAAGTCAAG TCCAAGTAAC ATCCCCGCCT      60

TAACCACAAG CAGGAGAA ATG AAG CAC ATT ATC AAC TCG TAT GAA AAC ATC       111
                    Met Lys His Ile Ile Asn Ser Tyr Glu Asn Ile
                     1               5                       10

AAC AAC ACA GCA AGA AAT AAT TCC GAC TGT CCT CGT GTG GTT TTG CCG       159
Asn Asn Thr Ala Arg Asn Asn Ser Asp Cys Pro Arg Val Val Leu Pro
             15                  20                  25

GAG GAG ATA TTT TTC ACA ATT TCC ATT GTT GGA GTT TTG GAG AAT CTG       207
Glu Glu Ile Phe Phe Thr Ile Ser Ile Val Gly Val Leu Glu Asn Leu
         30                  35                  40

ATC GTC CTG CTG GCT GTG TTC AAG AAT AAG AAT CTC CAG GCA CCC ATG       255
Ile Val Leu Leu Ala Val Phe Lys Asn Lys Asn Leu Gln Ala Pro Met
     45                  50                  55

TAC TTT TTC ATC TGT AGC TTG GCC ATA TCT GAT ATG CTG GGC AGC CTA       303
Tyr Phe Phe Ile Cys Ser Leu Ala Ile Ser Asp Met Leu Gly Ser Leu
 60                  65                  70                  75

TAT AAG ATC TTG GAA AAT ATC CTG ATC ATA TTG AGA AAC ATG GGC TAT       351
Tyr Lys Ile Leu Glu Asn Ile Leu Ile Ile Leu Arg Asn Met Gly Tyr
                 80                  85                  90

CTC AAG CCA CGT GGC AGT TTT GAA ACC ACA GCC GAT GAC ATC ATC GAC       399
Leu Lys Pro Arg Gly Ser Phe Glu Thr Thr Ala Asp Asp Ile Ile Asp
             95                 100                 105

TCC CTG TTT GTC CTC TCC CTG CTT GGC TCC ATC TTC AGC CTG TCT GTG       447
Ser Leu Phe Val Leu Ser Leu Leu Gly Ser Ile Phe Ser Leu Ser Val
        110                 115                 120

ATT GCT GCG GAC CGC TAC ATC ACC ATC TTC CAC GCA CTG CGG TAC CAC       495
Ile Ala Ala Asp Arg Tyr Ile Thr Ile Phe His Ala Leu Arg Tyr His
    125                 130                 135

AGC ATC GTG ACC ATG CGC CGC ACT GTG GTG GTG CTT ACG GTC ATC TGG       543
Ser Ile Val Thr Met Arg Arg Thr Val Val Val Leu Thr Val Ile Trp
140                 145                 150                 155

ACG TTC TGC ACG GGG ACT GGC ATC ACC ATG GTG ATC TTC TCC CAT CAT       591
Thr Phe Cys Thr Gly Thr Gly Ile Thr Met Val Ile Phe Ser His His
                160                 165                 170
```

```
GTG CCC ACA GTG ATC ACC TTC ACG TCG CTG TTC CCG CTG ATG CTG GTC      639
Val Pro Thr Val Ile Thr Phe Thr Ser Leu Phe Pro Leu Met Leu Val
            175                 180                 185

TTC ATC CTG TGC CTC TAT GTG CAC ATG TTC CTG CTG GCT CGA TCC CAC      687
Phe Ile Leu Cys Leu Tyr Val His Met Phe Leu Leu Ala Arg Ser His
        190                 195                 200

ACC AGG AAG ATC TCC ACC CTC CCC AGA GCC AAC ATG AAA GGG GCC ATC      735
Thr Arg Lys Ile Ser Thr Leu Pro Arg Ala Asn Met Lys Gly Ala Ile
    205                 210                 215

ACA CTG ACC ATC CTG CTC GGG GTC TTC ATC TTC TGC TGG GCC CCC TTT      783
Thr Leu Thr Ile Leu Leu Gly Val Phe Ile Phe Cys Trp Ala Pro Phe
220                 225                 230                 235

GTG CTT CAT GTC CTC TTG ATG ACA TTC TGC CCA AGT AAC CCC TAC TGC      831
Val Leu His Val Leu Leu Met Thr Phe Cys Pro Ser Asn Pro Tyr Cys
                240                 245                 250

GCC TGC TAC ATG TCT CTC TTC CAG GTG AAC GGC ATG TTG ATC ATG TGC      879
Ala Cys Tyr Met Ser Leu Phe Gln Val Asn Gly Met Leu Ile Met Cys
            255                 260                 265

AAT GCC GTC ATT GAC CCC TTC ATA TAT GCC TTC CGG AGC CCA GAG CTC      927
Asn Ala Val Ile Asp Pro Phe Ile Tyr Ala Phe Arg Ser Pro Glu Leu
        270                 275                 280

AGG GAC GCA TTC AAA AAG ATG ATC TTC TGC AGC AGG TAC TGG               969
Arg Asp Ala Phe Lys Lys Met Ile Phe Cys Ser Arg Tyr Trp
    285                 290                 295

TAGAATGGCT GATCCCTGGT TTTAGAATCC ATGGGAATAA CGTTGC                   1015

(2) INFORMATION FOR SEQ ID NO:4:

(i) SEQUENCE CHARACTERISTICS:
        (A) LENGTH: 297 amino acids
        (B) TYPE: amino acid
        (D) TOPOLOGY: linear (ii) MOLECULE TYPE: protein (xi) SEQUENCE DESCRIPTION: SEQ ID NO:4:

Met Lys His Ile Ile Asn Ser Tyr Glu Asn Ile Asn Asn Thr Ala Arg
  1               5                  10                  15

Asn Asn Ser Asp Cys Pro Arg Val Val Leu Pro Glu Glu Ile Phe Phe
                20                  25                  30

Thr Ile Ser Ile Val Gly Val Leu Glu Asn Leu Ile Val Leu Leu Ala
            35                  40                  45

Val Phe Lys Asn Lys Asn Leu Gln Ala Pro Met Tyr Phe Phe Ile Cys
        50                  55                  60

Ser Leu Ala Ile Ser Asp Met Leu Gly Ser Leu Tyr Lys Ile Leu Glu
 65                  70                  75                  80

Asn Ile Leu Ile Ile Leu Arg Asn Met Gly Tyr Leu Lys Pro Arg Gly
                85                  90                  95

Ser Phe Glu Thr Thr Ala Asp Asp Ile Ile Asp Ser Leu Phe Val Leu
               100                 105                 110

Ser Leu Leu Gly Ser Ile Phe Ser Leu Ser Val Ile Ala Ala Asp Arg
            115                 120                 125

Tyr Ile Thr Ile Phe His Ala Leu Arg Tyr His Ser Ile Val Thr Met
        130                 135                 140

Arg Arg Thr Val Val Val Leu Thr Val Ile Trp Thr Phe Cys Thr Gly
145                 150                 155                 160

Thr Gly Ile Thr Met Val Ile Phe Ser His His Val Pro Thr Val Ile
                165                 170                 175
```

```
Thr Phe Thr Ser Leu Phe Pro Leu Met Leu Val Phe Ile Leu Cys Leu
            180                 185                 190

Tyr Val His Met Phe Leu Leu Ala Arg Ser His Thr Arg Lys Ile Ser
            195                 200                 205

Thr Leu Pro Arg Ala Asn Met Lys Gly Ala Ile Thr Leu Thr Ile Leu
            210                 215                 220

Leu Gly Val Phe Ile Phe Cys Trp Ala Pro Phe Val Leu His Val Leu
225                 230                 235                 240

Leu Met Thr Phe Cys Pro Ser Asn Pro Tyr Cys Ala Cys Tyr Met Ser
                245                 250                 255

Leu Phe Gln Val Asn Gly Met Leu Ile Met Cys Asn Ala Val Ile Asp
            260                 265                 270

Pro Phe Ile Tyr Ala Phe Arg Ser Pro Glu Leu Arg Asp Ala Phe Lys
            275                 280                 285

Lys Met Ile Phe Cys Ser Arg Tyr Trp
            290                 295

(2) INFORMATION FOR SEQ ID NO:5:

(i) SEQUENCE CHARACTERISTICS:
        (A) LENGTH: 1080 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Homo sapiens (ix) FEATURE:
        (A) NAME/KEY: CDS
        (B) LOCATION: 1..1080

(xi) SEQUENCE DESCRIPTION: SEQ ID NO:5:

ATG AGC ATC CAA AAG AAG TAT CTG GAG GGA GAT TTT GTC TTT CCT GTG        48
Met Ser Ile Gln Lys Lys Tyr Leu Glu Gly Asp Phe Val Phe Pro Val
 1               5                  10                  15

AGC AGC AGC AGC TTC CTA CGG ACC CTG CTG GAG CCC CAG CTC GGA TCA        96
Ser Ser Ser Ser Phe Leu Arg Thr Leu Leu Glu Pro Gln Leu Gly Ser
                20                  25                  30

GCC CTT CTG ACA GCA ATG AAT GCT TCG TGC TGC CTG CCC TCT GTT CAG       144
Ala Leu Leu Thr Ala Met Asn Ala Ser Cys Cys Leu Pro Ser Val Gln
            35                  40                  45

CCA ACA CTG CCT AAT GGC TCG GAG CAC CTC CAA GCC CCT TTC TTC AGC       192
Pro Thr Leu Pro Asn Gly Ser Glu His Leu Gln Ala Pro Phe Phe Ser
 50                 55                  60

AAC CAG AGC AGC AGC GCC TTC TGT GAG CAG GTC TTC ATC AAG CCC GAG       240
Asn Gln Ser Ser Ser Ala Phe Cys Glu Gln Val Phe Ile Lys Pro Glu
 65                 70                  75                  80

ATT TTC CTG TCT CTG GGC ATC GTC AGT CTG CTG GAA AAC ATC CTG GTT       288
Ile Phe Leu Ser Leu Gly Ile Val Ser Leu Leu Glu Asn Ile Leu Val
                85                  90                  95

ATC CTG GCC GTG GTC AGG AAC GGC AAC CTG CAC TCC CCG ATG TAC TTC       336
Ile Leu Ala Val Val Arg Asn Gly Asn Leu His Ser Pro Met Tyr Phe
                100                 105                 110

TTT CTC TGC AGC CTG GCG GTG GCC GAC ATG CTG GTA AGT GTG TCC AAT       384
Phe Leu Cys Ser Leu Ala Val Ala Asp Met Leu Val Ser Val Ser Asn
            115                 120                 125
```

```
GCC CTG GAG ACC ATC ATG ATC GCC ATC GTC CAC AGC GAC TAC CTG ACC      432
Ala Leu Glu Thr Ile Met Ile Ala Ile Val His Ser Asp Tyr Leu Thr
    130                 135                 140

TTC GAG GAC CAG TTT ATC CAG CAC ATG GAC AAC ATC TTC GAC TCC ATG      480
Phe Glu Asp Gln Phe Ile Gln His Met Asp Asn Ile Phe Asp Ser Met
145                 150                 155                 160

ATC TGC ATC TCC CTG GTG GCC TCC ATC TGC AAC CTC CTG GCC ATC GCC      528
Ile Cys Ile Ser Leu Val Ala Ser Ile Cys Asn Leu Leu Ala Ile Ala
                165                 170                 175

GTC GAC AGG TAC GTC ACC ATC TTT TAC GCG CTC CGC TAC CAC AGC ATC      576
Val Asp Arg Tyr Val Thr Ile Phe Tyr Ala Leu Arg Tyr His Ser Ile
            180                 185                 190

ATG ACC GTG AGG AAG GCC CTC ACC TTG ATC GTG GCC ATC TGG GTC TGC      624
Met Thr Val Arg Lys Ala Leu Thr Leu Ile Val Ala Ile Trp Val Cys
        195                 200                 205

TGC GGC GTC TGT GGC GTG GTG TTC ATC GTC TAC TCG GAG AGC AAA ATG      672
Cys Gly Val Cys Gly Val Val Phe Ile Val Tyr Ser Glu Ser Lys Met
    210                 215                 220

GTC ATT GTG TGC CTC ATC ACC ATG TTC TTC GCC ATG ATG CTC CTC ATG      720
Val Ile Val Cys Leu Ile Thr Met Phe Phe Ala Met Met Leu Leu Met
225                 230                 235                 240

GGC ACC CTC TAC GTG CAC ATG TTC CTC TTT GCG CGG CTG CAC GTC AAG      768
Gly Thr Leu Tyr Val His Met Phe Leu Phe Ala Arg Leu His Val Lys
                245                 250                 255

CGC ATA GCA GCA CTG CCA CCT GCC GAC GGG GTG GCC CCA CAG CAA CAC      816
Arg Ile Ala Ala Leu Pro Pro Ala Asp Gly Val Ala Pro Gln Gln His
            260                 265                 270

TCA TGC ATG AAG GGG GCA GTC ACC ATC ACC ATT CTC CTG GGC GTG TTC      864
Ser Cys Met Lys Gly Ala Val Thr Ile Thr Ile Leu Leu Gly Val Phe
        275                 280                 285

ATC TTC TGC TGG GCC CCC TTC TTC CTC CAC CTG GTC CTC ATC ATC ACC      912
Ile Phe Cys Trp Ala Pro Phe Phe Leu His Leu Val Leu Ile Ile Thr
    290                 295                 300

TGC CCC ACC AAC CCC TAC TGC ATC TGC TAC ACT GCC CAC TTC AAC ACC      960
Cys Pro Thr Asn Pro Tyr Cys Ile Cys Tyr Thr Ala His Phe Asn Thr
305                 310                 315                 320

TAC CTG GTC CTC ATC ATG TGC AAC TCC GTC ATC GAC CCA CTC ATC TAC     1008
Tyr Leu Val Leu Ile Met Cys Asn Ser Val Ile Asp Pro Leu Ile Tyr
                325                 330                 335

GCT TTC CGG AGC CTG GAA TTG CGC AAC ACC TTT AGG GAG ATT CTC TGT     1056
Ala Phe Arg Ser Leu Glu Leu Arg Asn Thr Phe Arg Glu Ile Leu Cys
            340                 345                 350

GGC TGC AAC GGC ATG AAC TTG GGA                                     1080
Gly Cys Asn Gly Met Asn Leu Gly
        355                 360
```

(2) INFORMATION FOR SEQ ID NO:6:

(i) SEQUENCE CHARACTERISTICS:
        (A) LENGTH: 360 amino acids
        (B) TYPE: amino acid
        (D) TOPOLOGY: linear (ii) MOLECULE TYPE: protein (xi) SEQUENCE DESCRIPTION: SEQ ID NO:6:

```
Met Ser Ile Gln Lys Lys Tyr Leu Glu Gly Asp Phe Val Phe Pro Val
1               5                   10                  15

Ser Ser Ser Ser Phe Leu Arg Thr Leu Leu Glu Pro Gln Leu Gly Ser
            20                  25                  30
```

```
Ala Leu Leu Thr Ala Met Asn Ala Ser Cys Cys Leu Pro Ser Val Gln
            35                  40                  45

Pro Thr Leu Pro Asn Gly Ser Glu His Leu Gln Ala Pro Phe Phe Ser
 50                  55                  60

Asn Gln Ser Ser Ser Ala Phe Cys Glu Gln Val Phe Ile Lys Pro Glu
 65                  70                  75                  80

Ile Phe Leu Ser Leu Gly Ile Val Ser Leu Leu Glu Asn Ile Leu Val
                 85                  90                  95

Ile Leu Ala Val Val Arg Asn Gly Asn Leu His Ser Pro Met Tyr Phe
                100                 105                 110

Phe Leu Cys Ser Leu Ala Val Ala Asp Met Leu Val Ser Val Ser Asn
            115                 120                 125

Ala Leu Glu Thr Ile Met Ile Ala Ile Val His Ser Asp Tyr Leu Thr
            130                 135                 140

Phe Glu Asp Gln Phe Ile Gln His Met Asp Asn Ile Phe Asp Ser Met
145                 150                 155                 160

Ile Cys Ile Ser Leu Val Ala Ser Ile Cys Asn Leu Leu Ala Ile Ala
                165                 170                 175

Val Asp Arg Tyr Val Thr Ile Phe Tyr Ala Leu Arg Tyr His Ser Ile
                180                 185                 190

Met Thr Val Arg Lys Ala Leu Thr Leu Ile Val Ala Ile Trp Val Cys
            195                 200                 205

Cys Gly Val Cys Gly Val Val Phe Ile Val Tyr Ser Glu Ser Lys Met
210                 215                 220

Val Ile Val Cys Leu Ile Thr Met Phe Phe Ala Met Met Leu Leu Met
225                 230                 235                 240

Gly Thr Leu Tyr Val His Met Phe Leu Phe Ala Arg Leu His Val Lys
                245                 250                 255

Arg Ile Ala Ala Leu Pro Pro Ala Asp Gly Val Ala Pro Gln Gln His
            260                 265                 270

Ser Cys Met Lys Gly Ala Val Thr Ile Thr Ile Leu Leu Gly Val Phe
            275                 280                 285

Ile Phe Cys Trp Ala Pro Phe Phe Leu His Leu Val Leu Ile Ile Thr
            290                 295                 300

Cys Pro Thr Asn Pro Tyr Cys Ile Cys Tyr Thr Ala His Phe Asn Thr
305                 310                 315                 320

Tyr Leu Val Leu Ile Met Cys Asn Ser Val Ile Asp Pro Leu Ile Tyr
                325                 330                 335

Ala Phe Arg Ser Leu Glu Leu Arg Asn Thr Phe Arg Glu Ile Leu Cys
            340                 345                 350

Gly Cys Asn Gly Met Asn Leu Gly
            355                 360

(2) INFORMATION FOR SEQ ID NO:7:

(i) SEQUENCE CHARACTERISTICS:
        (A) LENGTH: 996 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
```

(A) ORGANISM: homo sapiens (ix) FEATURE:
    (A) NAME/KEY: CDS
    (B) LOCATION: 1..996

(xi) SEQUENCE DESCRIPTION: SEQ ID NO:7:

```
ATG GTG AAC TCC ACC CAC CGT GGG ATG CAC ACT TCT CTG CAC CTC TGG      48
Met Val Asn Ser Thr His Arg Gly Met His Thr Ser Leu His Leu Trp
 1               5                  10                  15

AAC CGC AGC AGT TAC AGA CTG CAC AGC AAT GCC AGT GAG TCC CTT GGA      96
Asn Arg Ser Ser Tyr Arg Leu His Ser Asn Ala Ser Glu Ser Leu Gly
                20                  25                  30

AAA GGC TAC TCT GAT GGA GGG TGC TAC GAG CAA CTT TTT GTC TCT CCT     144
Lys Gly Tyr Ser Asp Gly Gly Cys Tyr Glu Gln Leu Phe Val Ser Pro
            35                  40                  45

GAG GTG TTT GTG ACT CTG GGT GTC ATC AGC TTG TTG GAG AAT ATC TTA     192
Glu Val Phe Val Thr Leu Gly Val Ile Ser Leu Leu Glu Asn Ile Leu
        50                  55                  60

GTG ATT GTG GCA ATA GCC AAG AAC AAG AAT CTG CAT TCA CCC ATG TAC     240
Val Ile Val Ala Ile Ala Lys Asn Lys Asn Leu His Ser Pro Met Tyr
 65                  70                  75                  80

TTT TTC ATC TGC AGC TTG GCT GTG GCT GAT ATG CTG GTG AGC GTT TCA     288
Phe Phe Ile Cys Ser Leu Ala Val Ala Asp Met Leu Val Ser Val Ser
                85                  90                  95

AAT GGA TCA GAA ACC ATT ATC ATC ACC CTA TTA AAC AGT ACA GAT ACG     336
Asn Gly Ser Glu Thr Ile Ile Ile Thr Leu Leu Asn Ser Thr Asp Thr
               100                 105                 110

GAT GCA CAG AGT TTC ACA GTG AAT ATT GAT AAT GTC ATT GAC TCG GTG     384
Asp Ala Gln Ser Phe Thr Val Asn Ile Asp Asn Val Ile Asp Ser Val
           115                 120                 125

ATC TGT AGC TCC TTG CTT GCA TCC ATT TGC AGC CTG CTT TCA ATT GCA     432
Ile Cys Ser Ser Leu Leu Ala Ser Ile Cys Ser Leu Leu Ser Ile Ala
       130                 135                 140

GTG GAC AGG TAC TTT ACT ATC TTC TAT GCT CTC CAG TAC CAT AAC ATT     480
Val Asp Arg Tyr Phe Thr Ile Phe Tyr Ala Leu Gln Tyr His Asn Ile
145                 150                 155                 160

ATG ACA GTT AAG CGG GTT GGG ATC ATC ATA AGT TGT ATC TGG GCA GCT     528
Met Thr Val Lys Arg Val Gly Ile Ile Ile Ser Cys Ile Trp Ala Ala
                165                 170                 175

TGC ACG GTT TCA GGC ATT TTG TTC ATC ATT TAC TCA GAT AGT AGT GCT     576
Cys Thr Val Ser Gly Ile Leu Phe Ile Ile Tyr Ser Asp Ser Ser Ala
            180                 185                 190

GTC ATC ATC TGC CTC ATC ACC ATG TTC TTC ACC ATG CTG GCT CTC ATG     624
Val Ile Ile Cys Leu Ile Thr Met Phe Phe Thr Met Leu Ala Leu Met
        195                 200                 205

GCT TCT CTC TAT GTC CAC ATG TTC CTG ATG GCC AGG CTT CAC ATT AAG     672
Ala Ser Leu Tyr Val His Met Phe Leu Met Ala Arg Leu His Ile Lys
    210                 215                 220

AGG ATT GCT GTC CTC CCC GGC ACT GGT GCC ATC CGC CAA GGT GCC AAT     720
Arg Ile Ala Val Leu Pro Gly Thr Gly Ala Ile Arg Gln Gly Ala Asn
225                 230                 235                 240

ATG AAG GGA GCG ATT ACC TTG ACC ATC CTG ATT GGC GTC TTT GTT GTC     768
Met Lys Gly Ala Ile Thr Leu Thr Ile Leu Ile Gly Val Phe Val Val
                245                 250                 255

TGC TGG GCC CCA TTC TTC CTC CAC TTA ATA TTC TAC ATC TCT TGT CCT     816
Cys Trp Ala Pro Phe Phe Leu His Leu Ile Phe Tyr Ile Ser Cys Pro
            260                 265                 270

CAG AAT CCA TAT TGT GTG TGC TTC ATG TCT CAC TTT AAC TTG TAT CTC     864
Gln Asn Pro Tyr Cys Val Cys Phe Met Ser His Phe Asn Leu Tyr Leu
        275                 280                 285
```

```
ATA CTG ATC ATG TGT AAT TCA ATC ATC GAT CCT CTG ATT TAT GCA CTC    912
Ile Leu Ile Met Cys Asn Ser Ile Ile Asp Pro Leu Ile Tyr Ala Leu
    290                 295                 300

CGG AGT CAA GAA CTG AGG AAA ACC TTC AAA GAG ATC ATC TGT TGC TAT    960
Arg Ser Gln Glu Leu Arg Lys Thr Phe Lys Glu Ile Ile Cys Cys Tyr
305                 310                 315                 320

CCC CTG GGA GGC CTT TGT GAC TTG TCT AGC AGA TAT                    996
Pro Leu Gly Gly Leu Cys Asp Leu Ser Ser Arg Tyr
                325                 330
```

(2) INFORMATION FOR SEQ ID NO:8:

(i) SEQUENCE CHARACTERISTICS:
        (A) LENGTH: 332 amino acids
        (B) TYPE: amino acid
        (D) TOPOLOGY: linear (ii) MOLECULE TYPE: protein (xi) SEQUENCE DESCRIPTION: SEQ ID NO:8:

```
Met Val Asn Ser Thr His Arg Gly Met His Thr Ser Leu His Leu Trp
 1               5                  10                  15

Asn Arg Ser Ser Tyr Arg Leu His Ser Asn Ala Ser Glu Ser Leu Gly
                20                  25                  30

Lys Gly Tyr Ser Asp Gly Gly Cys Tyr Glu Gln Leu Phe Val Ser Pro
            35                  40                  45

Glu Val Phe Val Thr Leu Gly Val Ile Ser Leu Leu Glu Asn Ile Leu
        50                  55                  60

Val Ile Val Ala Ile Ala Lys Asn Lys Asn Leu His Ser Pro Met Tyr
65                  70                  75                  80

Phe Phe Ile Cys Ser Leu Ala Val Ala Asp Met Leu Val Ser Val Ser
                85                  90                  95

Asn Gly Ser Glu Thr Ile Ile Ile Thr Leu Leu Asn Ser Thr Asp Thr
                100                 105                 110

Asp Ala Gln Ser Phe Thr Val Asn Ile Asp Asn Val Ile Asp Ser Val
            115                 120                 125

Ile Cys Ser Ser Leu Leu Ala Ser Ile Cys Ser Leu Leu Ser Ile Ala
130                 135                 140

Val Asp Arg Tyr Phe Thr Ile Phe Tyr Ala Leu Gln Tyr His Asn Ile
145                 150                 155                 160

Met Thr Val Lys Arg Val Gly Ile Ile Ile Ser Cys Ile Trp Ala Ala
                165                 170                 175

Cys Thr Val Ser Gly Ile Leu Phe Ile Ile Tyr Ser Asp Ser Ser Ala
            180                 185                 190

Val Ile Ile Cys Leu Ile Thr Met Phe Phe Thr Met Leu Ala Leu Met
        195                 200                 205

Ala Ser Leu Tyr Val His Met Phe Leu Met Ala Arg Leu His Ile Lys
    210                 215                 220

Arg Ile Ala Val Leu Pro Gly Thr Gly Ala Ile Arg Gln Gly Ala Asn
225                 230                 235                 240

Met Lys Gly Ala Ile Thr Leu Thr Ile Leu Ile Gly Val Phe Val Val
                245                 250                 255

Cys Trp Ala Pro Phe Phe Leu His Leu Ile Phe Tyr Ile Ser Cys Pro
            260                 265                 270

Gln Asn Pro Tyr Cys Val Cys Phe Met Ser His Phe Asn Leu Tyr Leu
        275                 280                 285
```

```
Ile Leu Ile Met Cys Asn Ser Ile Ile Asp Pro Leu Ile Tyr Ala Leu
        290                 295                 300

Arg Ser Gln Glu Leu Arg Lys Thr Phe Lys Glu Ile Ile Cys Cys Tyr
305                 310                 315                 320

Pro Leu Gly Gly Leu Cys Asp Leu Ser Ser Arg Tyr
                325                 330
```

(2) INFORMATION FOR SEQ ID NO:9:

(i) SEQUENCE CHARACTERISTICS:
        (A) LENGTH: 975 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Mouse (ix) FEATURE:
        (A) NAME/KEY: CDS
        (B) LOCATION: 1..975

(xi) SEQUENCE DESCRIPTION: SEQ ID NO:9:

```
ATG AAC TCC TCC TCC ACC CTG ACT GTA TTG AAT CTT ACC CTG AAC GCC    48
Met Asn Ser Ser Ser Thr Leu Thr Val Leu Asn Leu Thr Leu Asn Ala
  1               5                  10                  15

TCA GAG GAT GGC ATT TTA GGA TCA AAT GTC AAG AAC AAG TCT TTG GCC    96
Ser Glu Asp Gly Ile Leu Gly Ser Asn Val Lys Asn Lys Ser Leu Ala
             20                  25                  30

TGT GAA GAA ATG GGC ATT GCC GTG GAG GTG TTC CTG ACC CTG GGT CTC   144
Cys Glu Glu Met Gly Ile Ala Val Glu Val Phe Leu Thr Leu Gly Leu
         35                  40                  45

GTC AGC CTC TTA GAG AAC ATC CTG GTC ATT GGG GCC ATA GTA AAG AAC   192
Val Ser Leu Leu Glu Asn Ile Leu Val Ile Gly Ala Ile Val Lys Asn
     50                  55                  60

AAA AAC CTG CAC TCA CCC ATG TAC TTC TAT GTG GGC AGC TTA GCC GTG   240
Lys Asn Leu His Ser Pro Met Tyr Phe Tyr Val Gly Ser Leu Ala Val
 65                  70                  75                  80

GCC GAC ATG CTG GTG AGC ATG TCC AAT GCC TGG GAG ACT GTC ACC ATA   288
Ala Asp Met Leu Val Ser Met Ser Asn Ala Trp Glu Thr Val Thr Ile
                 85                  90                  95

TAC TTG CTA AAT AAT AAA CAC CTG GTG ATA GCC GAC ACC TTT GTG CGA   336
Tyr Leu Leu Asn Asn Lys His Leu Val Ile Ala Asp Thr Phe Val Arg
            100                 105                 110

CAC ATC GAC AAC GTG TTC GAC TCC ATG ATC TGC ATC TCT GTG GTG GCC   384
His Ile Asp Asn Val Phe Asp Ser Met Ile Cys Ile Ser Val Val Ala
        115                 120                 125

TCG ATG TGC AGT TTG CTG GCC ATT GCG GTG GAC AGG TAC ATC ACC ATC   432
Ser Met Cys Ser Leu Leu Ala Ile Ala Val Asp Arg Tyr Ile Thr Ile
    130                 135                 140

TTC TAT GCC TTG CGC TAC CAC CAC ATC ATG ACC GCG AGG CGC TCG GGG   480
Phe Tyr Ala Leu Arg Tyr His His Ile Met Thr Ala Arg Arg Ser Gly
145                 150                 155                 160

GTG ATC ATC GCC TGC ATC TGG ACC TTC TGC ATA AGC TGC GGC ATT GTT   528
Val Ile Ile Ala Cys Ile Trp Thr Phe Cys Ile Ser Cys Gly Ile Val
                165                 170                 175
```

```
TTC ATC ATC TAC TAT GAG TCC AAG TAT GTG ATC ATT TGC CTC ATC TCC        576
Phe Ile Ile Tyr Tyr Glu Ser Lys Tyr Val Ile Ile Cys Leu Ile Ser
            180                 185                 190

ATG TTC TTC ACC ATG CTG TTC TTC ATG GTG TCT CTG TAT ATA CAC ATG        624
Met Phe Phe Thr Met Leu Phe Phe Met Val Ser Leu Tyr Ile His Met
        195                 200                 205

TTC CTC CTG GCC CGG AAC CAT GTC AAG CGG ATA GCA GCT TCC CCC AGA        672
Phe Leu Leu Ala Arg Asn His Val Lys Arg Ile Ala Ala Ser Pro Arg
    210                 215                 220

TAC AAC TCC GTG AGG CAA AGG ACC AGC ATG AAG GGG GCT ATT ACC CTC        720
Tyr Asn Ser Val Arg Gln Arg Thr Ser Met Lys Gly Ala Ile Thr Leu
225                 230                 235                 240

ACC ATG CTA CTG GGG ATT TTC ATT GTC TGC TGG TCT CCC TTC TTT CTT        768
Thr Met Leu Leu Gly Ile Phe Ile Val Cys Trp Ser Pro Phe Phe Leu
                245                 250                 255

CAC CTT ATC TTA ATG ATC TCC TGC CCT CAG AAC GTC TAC TGC TCT TGC        816
His Leu Ile Leu Met Ile Ser Cys Pro Gln Asn Val Tyr Cys Ser Cys
            260                 265                 270

TTT ATG TCT TAC TTC AAC ATG TAC CTT ATA CTC ATC ATG TGC AAC TCC        864
Phe Met Ser Tyr Phe Asn Met Tyr Leu Ile Leu Ile Met Cys Asn Ser
        275                 280                 285

GTG ATC GAT CCT CTC ATC TAC GCC CTC CGC AGC CAA GAG ATG CGG AGG        912
Val Ile Asp Pro Leu Ile Tyr Ala Leu Arg Ser Gln Glu Met Arg Arg
    290                 295                 300

ACC TTT AAG GAG ATC GTC TGT TGT CAC GGA TTC CGG CGA CCT TGT AGG        960
Thr Phe Lys Glu Ile Val Cys Cys His Gly Phe Arg Arg Pro Cys Arg
305                 310                 315                 320

CTC CTT GGC GGG TAT                                                    975
Leu Leu Gly Gly Tyr
                325

(2) INFORMATION FOR SEQ ID NO:10:

(i) SEQUENCE CHARACTERISTICS:
        (A) LENGTH: 325 amino acids
        (B) TYPE: amino acid
        (D) TOPOLOGY: linear (ii) MOLECULE TYPE: protein (xi) SEQUENCE DESCRIPTION: SEQ ID NO:10:

Met Asn Ser Ser Thr Leu Thr Val Leu Asn Leu Thr Leu Asn Ala
 1               5                  10                  15

Ser Glu Asp Gly Ile Leu Gly Ser Asn Val Lys Asn Lys Ser Leu Ala
                20                  25                  30

Cys Glu Glu Met Gly Ile Ala Val Glu Val Phe Leu Thr Leu Gly Leu
            35                  40                  45

Val Ser Leu Leu Glu Asn Ile Leu Val Ile Gly Ala Ile Val Lys Asn
        50                  55                  60

Lys Asn Leu His Ser Pro Met Tyr Phe Tyr Val Gly Ser Leu Ala Val
65                  70                  75                  80

Ala Asp Met Leu Val Ser Met Ser Asn Ala Trp Glu Thr Val Thr Ile
                85                  90                  95

Tyr Leu Leu Asn Asn Lys His Leu Val Ile Ala Asp Thr Phe Val Arg
                100                 105                 110

His Ile Asp Asn Val Phe Asp Ser Met Ile Cys Ile Ser Val Val Ala
            115                 120                 125

Ser Met Cys Ser Leu Leu Ala Ile Ala Val Asp Arg Tyr Ile Thr Ile
        130                 135                 140
```

```
Phe Tyr Ala Leu Arg Tyr His His Ile Met Thr Ala Arg Arg Ser Gly
145                 150                 155                 160

Val Ile Ile Ala Cys Ile Trp Thr Phe Cys Ile Ser Cys Gly Ile Val
            165                 170                 175

Phe Ile Ile Tyr Tyr Glu Ser Lys Tyr Val Ile Ile Cys Leu Ile Ser
            180                 185                 190

Met Phe Phe Thr Met Leu Phe Phe Met Val Ser Leu Tyr Ile His Met
        195                 200                 205

Phe Leu Leu Ala Arg Asn His Val Lys Arg Ile Ala Ala Ser Pro Arg
        210                 215                 220

Tyr Asn Ser Val Arg Gln Arg Thr Ser Met Lys Gly Ala Ile Thr Leu
225                 230                 235                 240

Thr Met Leu Leu Gly Ile Phe Ile Val Cys Trp Ser Pro Phe Phe Leu
                245                 250                 255

His Leu Ile Leu Met Ile Ser Cys Pro Gln Asn Val Tyr Cys Ser Cys
                260                 265                 270

Phe Met Ser Tyr Phe Asn Met Tyr Leu Ile Leu Ile Met Cys Asn Ser
            275                 280                 285

Val Ile Asp Pro Leu Ile Tyr Ala Leu Arg Ser Gln Glu Met Arg Arg
290                 295                 300

Thr Phe Lys Glu Ile Val Cys Cys His Gly Phe Arg Arg Pro Cys Arg
305                 310                 315                 320

Leu Leu Gly Gly Tyr
                325

(2) INFORMATION FOR SEQ ID NO:11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (oligo)

(xi) SEQUENCE DESCRIPTION: SEQ ID NO:11:

TACGCAGCTG CCGCTACCAC AGCATC                                        26

(2) INFORMATION FOR SEQ ID NO:12:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (oligo)

(xi) SEQUENCE DESCRIPTION: SEQ ID NO:12:

GAAGAGCAGT ATGATGAAGG TGGGTCAGAT                                    30

(2) INFORMATION FOR SEQ ID NO:13:

(i) SEQUENCE CHARACTERISTICS:
        (A) LENGTH: 14 amino acids
        (B) TYPE: amino acid
        (D) TOPOLOGY: linear (ii) MOLECULE TYPE: protein (xi) SEQUENCE DESCRIPTION: SEQ ID NO:13:
```

```
Ala Ser Tyr Ser Met Glu His Phe Arg Trp Gly Lys Pro Val
 1               5                  10
```

(2) INFORMATION FOR SEQ ID NO:14:

(i) SEQUENCE CHARACTERISTICS:
        (A) LENGTH: 22 amino acids
        (B) TYPE: amino acid
        (D) TOPOLOGY: linear (ii) MOLECULE TYPE: protein (xi) SEQUENCE DESCRIPTION: SEQ ID NO:14:

```
Ala Glu Lys Lys Asp Glu Gly Pro Tyr Arg Met Glu His Phe Arg Trp
 1               5                  10                  15
Gly Ser Pro Pro Lys Asp
             20
```

(2) INFORMATION FOR SEQ ID NO:15:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:15:

```
Tyr Val Met Gly His Phe Arg Trp Asp Arg Phe Gly
 1               5                  10
```

(2) INFORMATION FOR SEQ ID NO:16:

(i) SEQUENCE CHARACTERISTICS:
        (A) LENGTH: 10 amino acids
        (B) TYPE: amino acid
        (D) TOPOLOGY: linear (ii) MOLECULE TYPE: protein (xi) SEQUENCE DESCRIPTION: SEQ ID NO:16:

```
Ser Tyr Ser Met Glu His Phe Arg Trp Gly
 1               5                  10
```

(2) INFORMATION FOR SEQ ID NO:17:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:17:

```
Met Glu His Phe Arg Trp Gly
 1               5
```

(2) INFORMATION FOR SEQ ID NO:18:

(i) SEQUENCE CHARACTERISTICS:
        (A) LENGTH: 13 amino acids
        (B) TYPE: amino acid
        (D) TOPOLOGY: linear (ii) MOLECULE TYPE: protein (xi) SEQUENCE DESCRIPTION: SEQ ID NO:18:

```
Ser Tyr Ser Met Glu His Phe Arg Trp Gly Lys Pro Val
 1               5                   10
```

(2) INFORMATION FOR SEQ ID NO:19:

(i) SEQUENCE CHARACTERISTICS:
        (A) LENGTH:  10 amino acids
        (B) TYPE: amino acid
        (D) TOPOLOGY: linear (ii) MOLECULE TYPE: protein (xi) SEQUENCE DESCRIPTION: SEQ ID NO:19:

```
Met Glu His Phe Arg Trp Gly Lys Pro Val
 1               5                   10
```

(2) INFORMATION FOR SEQ ID NO:20:

(i) SEQUENCE CHARACTERISTICS:
        (A) LENGTH:  12 amino acids
        (B) TYPE: amino acid
        (D) TOPOLOGY: linear (ii) MOLECULE TYPE: protein (xi) SEQUENCE DESCRIPTION: SEQ ID NO:20:

```
Tyr Val Met Gly His Phe Arg Trp Asp Arg Pro Gly
 1               5                   10
```

(2) INFORMATION FOR SEQ ID NO:21:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:21:

```
Phe Val Met Gly His Phe Arg Trp Asp Arg Phe Gly
 1               5                   10
```

(2) INFORMATION FOR SEQ ID NO:22:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:22:

```
Thr Val Met Gly His Phe Arg Trp Asp Arg Phe Gly
 1               5                   10
```

(2) INFORMATION FOR SEQ ID NO:23:

(i) SEQUENCE CHARACTERISTICS:
        (A) LENGTH: 12 amino acids
        (B) TYPE: amino acid
        (D) TOPOLOGY: linear (ii) MOLECULE TYPE: protein (xi) SEQUENCE DESCRIPTION: SEQ ID NO:23:

```
Tyr Val Met Gly His Phe Arg Trp Asp Arg Pro Gly
 1               5                   10
```